United States Patent
Nirogi et al.

(10) Patent No.: US 9,957,257 B2
(45) Date of Patent: May 1, 2018

(54) AMIDE COMPOUNDS AS 5-HT4 RECEPTOR AGONISTS

(71) Applicant: SUVEN LIFE SCIENCES LIMITED, Hyderabad, Andhra Pradesh (IN)

(72) Inventors: Ramakrishna Nirogi, Hyderabad (IN); Anil Karbhari Shinde, Hyderabad (IN); Abdul Rasheed Mohammed, Hyderabad (IN); Sangram Keshari Saraf, Hyderabad (IN); Narsimha Bogaraju, Hyderabad (IN); Ramkumar Subramanian, Hyderabad (IN); Pradeep Jayarajan, Hyderabad (IN); Gopinadh Bhyrapuneni, Hyderabad (IN); Venkateswarlu Jasti, Hyderabad (IN)

(73) Assignee: SUVEN LIFE SCIENCES LIMITED, Hyderabad (IN)

( * ) Notice: Subject to any disclaimer, the term of this patent is extended or adjusted under 35 U.S.C. 154(b) by 0 days. days.

(21) Appl. No.: 15/549,663

(22) PCT Filed: Jan. 7, 2016

(86) PCT No.: PCT/IN2016/000008
§ 371 (c)(1),
(2) Date: Aug. 9, 2017

(87) PCT Pub. No.: WO2016/128990
PCT Pub. Date: Aug. 18, 2016

(65) Prior Publication Data
US 2018/0051011 A1    Feb. 22, 2018

(30) Foreign Application Priority Data

Feb. 13, 2015 (IN) .............................. 709/CHE/2015

(51) Int. Cl.
*C07D 405/12* (2006.01)
*C07D 405/14* (2006.01)

(52) U.S. Cl.
CPC ......... *C07D 405/12* (2013.01); *C07D 405/14* (2013.01)

(58) Field of Classification Search
CPC .......................... C07D 405/12; C07D 405/14
USPC .......................................................... 514/320
See application file for complete search history.

(56) References Cited

FOREIGN PATENT DOCUMENTS

| WO | 2005/092882 | 10/2005 |
|---|---|---|
| WO | 2007/048643 | 5/2007 |
| WO | 2007/068739 | 6/2007 |
| WO | 2011/099305 | 8/2011 |
| WO | 2013/042135 | 3/2013 |
| WO | 2015/092804 | 6/2015 |

OTHER PUBLICATIONS

Lo et al., "SSP-002392, a new 5-HT4 receptor agonist, dose-dependently reverses scopolamine-induced learning and memory impairments in C57B1/6 mice" Neuropharmacology 85:178-189 (2014).
European Patent Office, "International Search Report" issued in PCT/IN2016/000008 dated May 9, 2016.
European Patent Office, "Written Opinion of the International Searching Authority" issued in PCT/IN2016/000008 dated May 9, 2016.
European Patent Office, "Written Opinion of the International Preliminary Examining Authority" issued in PCT/IN2016/000008 dated Feb. 2, 2017.
European Patent Office, "International Preliminary Report on Patentability" issued in PCT/IN2016/000008 dated May 22, 2017, and related correspondence.
Brown et al., "Drug-Induced Long QT Syndrome: Is HERG the Root of All Evil" Pharmaceutical News 7:15-20 (2000).
Brown et al., "Drugs, hERG, and sudden death" Cell Calcium 35:543-547 (2004).

*Primary Examiner* — Kristin A Vajda
(74) *Attorney, Agent, or Firm* — IpHorgan Ltd.

(57) ABSTRACT

The present invention relates to compounds of formula (I), including their stereoisomers and pharmaceutically acceptable salts. This invention also relates to methods of making such compounds and pharmaceutical compositions comprising such compounds. The compounds of this invention are useful in the treatment of various disorders that are related to 5-hydroxytryptamine 4 (5-HT$_4$) receptor.

9 Claims, 3 Drawing Sheets

AMIDE COMPOUNDS AS 5-HT4 RECEPTOR AGONISTS

CROSS REFERENCE TO RELATED APPLICATIONS

This application is a national stage completion application of PCT Application No. PCT/IN2016/000008, filed Jan. 7, 2016, and claims the benefit of India Application No. 709/CHE/2015, filed Feb. 13, 2015. Each of these applications is incorporated by reference herein in its entirety.

FIELD OF INVENTION

The present invention relates to compounds of formula (I), or their stereoisomers and pharmaceutically acceptable salts thereof as 5-hydroxytryptamine 4 (5-HT$_4$) receptor agonists. The present invention also describes method of making such compounds and pharmaceutical compositions comprising such compounds.

BACKGROUND OF THE INVENTION

The 5-HT$_4$ receptor is one of the seven subtypes of 5-hydroxytryptamine (5-HT) receptors. It is a 7-transmembrane domain protein coupled to a G-protein positively linked to the activation of adenylate cyclase (Molecular Pharmacology, 1990, 37, 408-411). 5-HT$_4$ receptor agonists are found to have potential utility in the treatment of disorders such as Alzheimer's disease (AD), schizopherenia, depression, attention deficit hyperactivity disorder, Huntington's disease, Parkinson's disease and several other psychiatric disorders (Current Topics in Medicinal Chemistry, 2010, 10, 527-553). 5-HT$_4$ receptor agonists are known to improve memory in different behavioral experiments in rodents (Naunyn-Schmiedeberg's Archives of Pharmacology, 2003, 367: 621-628). 5-HT$_4$ receptors also play a key role in the regulation of synaptic plasticity and the determination of particular properties of stored synaptic information (Cerebral Cortex, 2005, 15, 1037-1043). Autoradiographic studies using the 5-HT$_4$ receptor antagonists [$^{125}$I] SB207710 and [$^3$H]GR113808 in rat, mouse, guinea pig or post-mortem human brain showed that the 5-HT$_4$ receptor is present at a high density in the limbic system including the hippocampus and frontal cortex (Neuropharmacology 1994, 33, 527-541; European Neuropsychopharmacology, 2003, 13, 228-234) suggesting a role of 5-HT$_4$ receptor in memory and cognition.

No drugs are in the market that specifically targets the cellular mechanisms of Alzheimer's disease (AD), namely the generation of the neurotoxic amyloid β-protein (Aβ) from the amyloid precursor protein (APP). AD is a progressive neurodegenerative disorder characterized by the appearance of senile plaques mainly composed of amyloid β-protein (Aβ) and the development of neurofibrillary tangles in patient's brains (Journal of Neuropathology & Experimental Neurology, 1997, 56, 321-339). AD patients also have cognitive deficits, impaired long-term potentiation (LTP), learning and memory deficits (Neuron, 2004, 44, 181-193) and a consistent deficit in cholinergic neurotransmission.

Patent publications WO2005049608, WO2006090224, WO2011099305, WO2011101774, WO2007048643, WO2007068739, WO2007096352, US20080207690 and US20080269211 disclosed some 5-HT$_4$ receptor compounds. While several 5-HT$_4$ receptor agonists/partial agonists have been disclosed in the literature, no compound, either agonist or partial agonist targeting 5-HT$_4$ receptor is launched in the market until now for the treatment of dementia related disorders. Therefore, there is a need and scope to discover new 5-HT$_4$ receptor agonists/partial agonists with novel chemical structures for treatment of disorders that are affected by the 5-HT$_4$ receptor.

SUMMARY OF THE INVENTION

In one aspect, the present invention relates to 5-HT$_4$ receptor agonists of compound of formula (I),

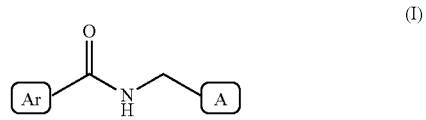

or their stereoisomers and pharmaceutically acceptable salts thereof;
wherein,

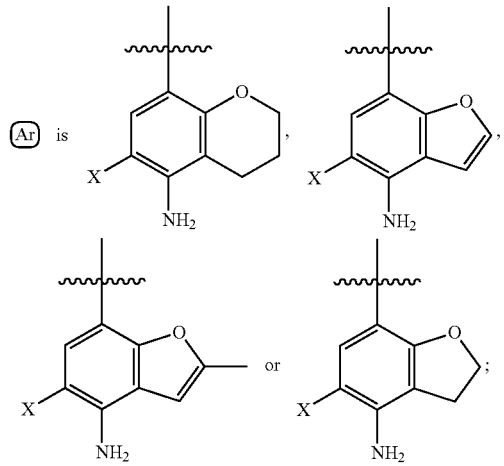

X is halogen or hydrogen;

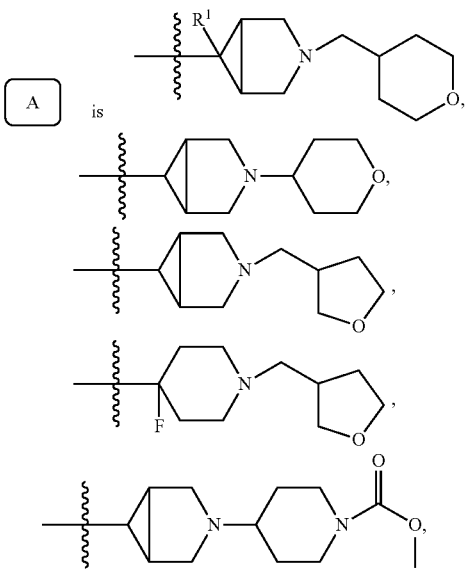

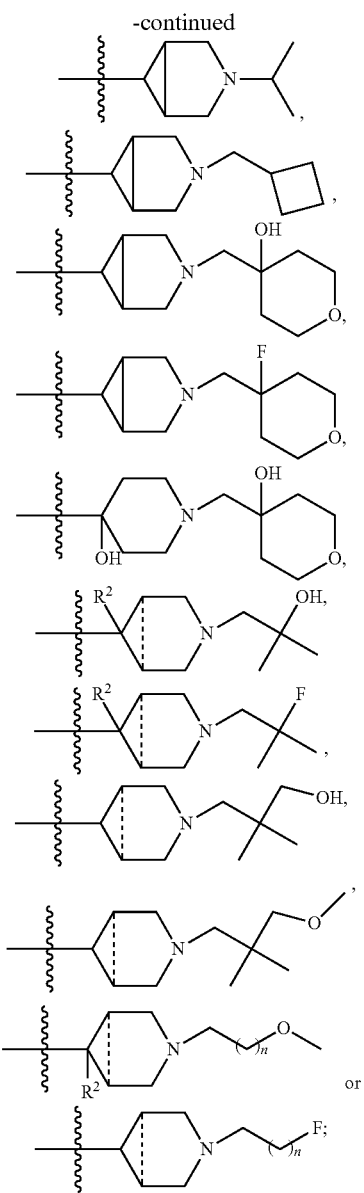

"⌇⌇⌇⌇" is point of attachment;
"--------" is a bond or no bond;
R₁ is hydrogen, fluroine or hydroxyl;
R₂ at each occurrence is hydrogen or fluorine;
"n" is 1 or 2.

In another aspect, the present invention relates to the processes for preparing the compounds of formula (I), or their stereoisomers and pharmaceutically acceptable salts thereof.

In yet another aspect, the present invention relates to pharmaceutical composition containing a therapeutically effective amount of at least one compound of formula (I), or their stereoisomers and pharmaceutically acceptable salts thereof and pharmaceutically acceptable excipients or carriers.

In yet another aspect, the present invention relates to compounds of formula (I), or their stereoisomers and pharmaceutically acceptable salts thereof, for use as 5-HT₄ receptor agonists.

In yet another aspect, the present invention relates to compounds of formula (I), or their stereoisomers and phar- maceutically acceptable salts thereof, for use in the treatment of various disorders selected from AD, schizophrenia, attention deficit hyperactivity disorder, Huntington's disease, Parkinson's disease or psychiatric disorders.

In still another aspect, the present invention relates to a method for the treatment of disorder related to 5-HT₄ receptor, comprising administering to a patient in need thereof, a therapeutically effective amount of a compound of formula (I), or their stereoisomers and pharmaceutically acceptable salts thereof.

In yet another aspect, the present invention relates to use of the compound of formula (I), or their stereoisomers and pharmaceutically acceptable salts thereof, for the manufacture of a medicament for the treatment of disorders related to 5-HT₄ receptor.

Representative compounds of the present invention include those specified below. The present invention should not be construed to be limited to them.

5-Amino-6-chloro-N-{[3-(tetrahydro-2H-pyran-4-ylmethyl)-3-azabicyclo[3.1.0]hex-6-yl]methyl}chroman-8-carboxamide hydrochloride;
5-Amino-6-chloro-N-{[3-(tetrahydro-2H-pyran-4-ylmethyl)-3-azabicyclo[3.1.0]hex-6-yl]methyl}chroman-8-carboxamide hemifumarate;
5-Amino-6-chloro-N-{[3-(tetrahydro-2H-pyran-4-ylmethyl)-3-azabicyclo[3.1.0]hex-6-yl]methyl}chroman-8-carboxamide L(+)-tartarate;
5-Amino-6-chloro-N-{[3-(tetrahydro-2H-pyran-4-ylmethyl)-3-azabicyclo[3.1.0]hex-6-yl]methyl}chroman-8-carboxamide;
5-Amino-6-chloro-N-{[3-(tetrahydro-2H-pyran-4-yl)-3-azabicyclo[3.1.0]hex-6-yl]methyl}chroman-8-carboxamide;
5-Amino-6-chloro-N-{[3-(tetrahydro-2H-pyran-4-yl)-3-azabicyclo[3.1.0]hex-6-yl]methyl}chroman-8-carboxamide L(+)-tartarate;
5-Amino-N-{[3-(tetrahydro-2H-pyran-4-ylmethyl)-3-azabicyclo[3.1.0]hex-6-yl]methyl}chroman-8-carboxamide L(+)-tartarate;
5-Amino-N-{[3-(tetrahydro-2H-pyran-4-ylmethyl)-3-azabicyclo[3.1.0]hex-6-yl]methyl}chroman-8-carboxamide;
(R,S) 5-Amino-6-chloro-N-{[3-(tetrahydro-3-furanylmethyl)-3-azabicyclo[3.1.0]hex-6-yl]methyl}chroman-8-carboxamide;
(R,S) 5-Amino-6-chloro-N-{[3-(tetrahydro-3-furanylmethyl)-3-azabicyclo[3.1.0]hex-6-yl]methyl}chroman-8-carboxamide L(+)-tartarate;
5-Amino-6-chloro-N-{[4-fluoro-1-(tetrahydro-3-furanylmethyl)-4-piperidinyl]methyl}chroman-8-carboxamide;
5-Amino-6-bromo-N-{[3-(tetrahydro-2H-pyran-4-ylmethyl)-3-azabicyclo[3.1.0]hex-6-yl]methyl}chroman-8-carboxamide;
5-Amino-6-bromo-N-{[3-(tetrahydro-2H-pyran-4-ylmethyl)-3-azabicyclo[3.1.0]hex-6-yl]methyl}chroman-8-carboxamide L(+)-tartarate;
4-Amino-5-chloro-N-{[3-(tetrahydro-2H-pyran-4-ylmethyl)-3-azabicyclo[3.1.0]hex-6-yl]methyl}benzofuran-7-carboxamide;
4-Amino-5-chloro-N-{[3-(tetrahydro-2H-pyran-4-ylmethyl)-3-azabicyclo[3.1.0]hex-6-yl]methyl}benzofuran-7-carboxamide hydrochloride;
4-Amino-5-chloro-N-{[3-(tetrahydro-2H-pyran-4-yl)-3-azabicyclo[3.1.0]hex-6-yl]methyl}benzofuran-7-carboxamide;
4-Amino-5-chloro-N-{[3-(tetrahydro-2H-pyran-4-yl)-3-azabicyclo[3.1.0]hex-6-yl]methyl}benzofuran-7-carboxamide oxalate;

4-Amino-5-chloro-N-{[3-(1-methoxycarbonylpiperidine-4-yl)-3-azabicyclo[3.1.0]hex-6-yl]methyl}benzofuran-7-carboxamide;

4-Amino-5-chloro-N-{[3-(1-methoxycarbonylpiperidine-4-yl)-3-azabicyclo[3.1.0]hex-6-yl]methyl}benzofuran-7-carboxamide oxalate;

4-Amino-5-chloro-2-methyl-N-{[3-(tetrahydro-2H-pyran-4-ylmethyl)-3-azabicyclo[3.1.0]hex-6-yl]methyl}benzofuran-7-carboxamide;

4-Amino-5-chloro-2-methyl-N-{[3-(tetrahydro-2H-pyran-4-ylmethyl)-3-azabicyclo[3.1.0]hex-6-yl]methyl}benzofuran-7-carboxamide hydrochloride;

4-Amino-5-chloro-N-[(3-isopropyl-3-azabicyclo[3.1.0]hex-6-yl)methyl]-2,3-dihydrobenzofuran-7-carboxamide;

4-Amino-5-chloro-N-[(3-isopropyl-3-azabicyclo[3.1.0]hex-6-yl)methyl]-2,3-dihydrobenzofuran-7-carboxamide oxalate;

4-Amino-5-chloro-N-{[3-(cyclobutylmethyl)-3-azabicyclo[3.1.0]hex-6-yl]methyl}-2,3-dihydrobenzofuran-7-carboxamide;

4-Amino-5-chloro-N-{[3-(cyclobutylmethyl)-3-azabicyclo[3.1.0]hex-6-yl]methyl}-2,3-dihydrobenzofuran-7-carboxamide oxalate;

4-Amino-5-chloro-N-{[3-(1-methoxycarbonylpiperidine-4-yl)-3-azabicyclo[3.1.0]hex-6-yl]methyl}-2,3-dihydrobenzofuran-7-carboxamide;

4-Amino-5-chloro-N-{[3-(1-methoxycarbonylpiperidine-4-yl)-3-azabicyclo[3.1.0]hex-6-yl]methyl}-2,3-dihydrobenzofuran-7-carboxamide L(+)-tartarate;

4-Amino-5-chloro-N-{[3-(tetrahydropyran-4-ylmethyl)-3-azabicyclo[3.1.0]hex-6-yl]methyl}-2,3-dihydrobenzofuran-7-carboxamide;

4-Amino-5-chloro-N-{[3-(tetrahydropyran-4-ylmethyl)-3-azabicyclo[3.1.0]hex-6-yl]methyl}-2,3-dihydrobenzofuran-7-carboxamide L(+)-tartarate;

4-Amino-5-chloro-N-{[3-(tetrahydropyran-4-yl)-3-azabicyclo[3.1.0]hex-6-yl]methyl}-2,3-dihydrobenzofuran-7-carboxamide;

4-Amino-5-chloro-N-{[3-(tetrahydropyran-4-yl)-3-azabicyclo[3.1.0]hex-6-yl]methyl}-2,3-dihydrobenzofuran-7-carboxamide oxalate;

4-Amino-5-bromo-N-{[3-(tetrahydropyran-4-yl)-3-azabicyclo[3.1.0]hex-6-yl]methyl}-2,3-dihydrobenzofuran-7-carboxamide;

4-Amino-5-bromo-N-{[3-(tetrahydropyran-4-yl)-3-azabicyclo[3.1.0]hex-6-yl]methyl}-2,3-dihydrobenzofuran-7-carboxamide oxalate;

5-Amino-6-chloro-N-{[3-(4-hydroxytetrahydro-2H-pyran-4-ylmethyl)-3-azabicyclo[3.1.0]hex-6-yl]methyl}chroman-8-carboxamide;

5-Amino-6-chloro-N-{[3-(4-hydroxytetrahydro-2H-pyran-4-ylmethyl)-3-azabicyclo[3.1.0]hex-6-yl]methyl}chroman-8-carboxamide L(+)-tartarate;

4-Amino-5-chloro-N-{[3-(4-hydroxytetrahydro-2H-pyran-4-ylmethyl)-3-azabicyclo[3.1.0]hex-6-yl]methyl}benzofuran-7-carboxamide;

4-Amino-5-chloro-N-{[3-(4-hydroxytetrahydro-2H-pyran-4-ylmethyl)-3-azabicyclo[3.1.0]hex-6-yl]methyl}benzofuran-7-carboxamide oxalate;

4-Amino-5-chloro-N-{[1-(4-hydroxytetrahydro-2H-pyran-4-ylmethyl)-4-hydroxy-4-piperidinyl]methyl}benzofuran-7-carboxamide;

4-Amino-5-chloro-N-{[1-(4-hydroxytetrahydro-2H-pyran-4-ylmethyl)-4-hydroxy-4-piperidinyl]methyl}benzofuran-7-carboxamide L(+)-tartarate;

4-Amino-5-chloro-N-{[3-(4-hydroxytetrahydropyran-4-yl-methyl)-3-azabicyclo[3.1.0]hex-6-yl]methyl}-2,3-dihydrobenzofuran-7-carboxamide;

4-Amino-5-chloro-N-{[3-(4-hydroxytetrahydropyran-4-yl-methyl)-3-azabicyclo[3.1.0]hex-6-yl]methyl}-2,3-dihydrobenzofuran-7-carboxamide oxalate;

5-Amino-6-chloro-N-{[3-(4-fluorotetrahydro-2H-pyran-4-ylmethyl)-3-azabicyclo[3.1.0]hex-6-yl]methyl}chroman-8-carboxamide;

5-Amino-6-chloro-N-{[3-(4-fluorotetrahydro-2H-pyran-4-ylmethyl)-3-azabicyclo[3.1.0]hex-6-yl]methyl}chroman-8-carboxamide L(+)-tartarate;

5-Amino-6-chloro-N-{[3-(2-hydroxy-2-methyl propyl)-3-azabicyclo[3.1.0]hex-6-yl]methyl}chroman-8-carboxamide;

5-Amino-6-chloro-N-{[3-(2-hydroxy-2-methyl propyl)-3-azabicyclo[3.1.0]hex-6-yl]methyl}chroman-8-carboxamide L(+)-tartarate;

4-Amino-5-chloro-N-{[4-fluoro-1-(2-hydroxy-2-methyl propyl)-4-piperidinyl]methyl}benzofuran-7-carboxamide;

4-Amino-5-chloro-N-{[4-fluoro-1-(2-hydroxy-2-methyl propyl)-4-piperidinyl]methyl}benzofuran-7-carboxamide hydrochloride;

5-Amino-6-chloro-N-{[1-(2-hydroxy-2-methyl propyl)-4-piperidinyl]methyl}chroman-8-carboxamide;

5-Amino-6-chloro-N-{[1-(2-hydroxy-2-methyl propyl)-4-piperidinyl]methyl}chroman-8-carboxamide L(+)-tartarate;

4-Amino-5-chloro-N-{[3-(2-hydroxy-2-methylpropyl)-3-azabicyclo[3.1.0]hex-6-yl]methyl}-2,3-dihydrobenzofuran-7-carboxamide;

4-Amino-5-chloro-N-{[3-(2-hydroxy-2-methylpropyl)-3-azabicyclo[3.1.0]hex-6-yl]methyl}-2,3-dihydrobenzofuran-7-carboxamide oxalate;

5-Amino-6-chloro-N-{[4-fluoro-1-(2-hydroxy-2-methyl propyl)-4-piperidinyl]methyl}chroman-8-carboxamide;

5-Amino-6-chloro-N-{[4-fluoro-1-(2-hydroxy-2-methyl propyl)-4-piperidinyl]methyl}chroman-8-carboxamide L(+)-tartarate;

5-Amino-6-bromo-N-{[1-(2-hydroxy-2-methyl propyl)-4-piperidinyl]methyl}chroman-8-carboxamide;

5-Amino-6-bromo-N-{[1-(2-hydroxy-2-methyl propyl)-4-piperidinyl]methyl}chroman-8-carboxamide L(+)-tartarate;

5-Amino-6-bromo-N-{[4-fluoro-1-(2-hydroxy-2-methyl propyl)-4-piperidinyl]methyl}chroman-8-carboxamide;

5-Amino-6-bromo-N-{[4-fluoro-1-(2-hydroxy-2-methyl propyl)-4-piperidinyl]methyl}chroman-8-carboxamide L(+)-tartarate;

4-Amino-5-chloro-N-{[1-(2-hydroxy-2-methyl propyl)-4-piperidinyl]methyl}benzofuran-7-carboxamide;

4-Amino-5-chloro-N-{[1-(2-hydroxy-2-methyl propyl)-4-piperidinyl]methyl}benzofuran-7-carboxamide L(+)-tartarate;

4-Amino-5-chloro-N-{[4-fluoro-1-(2-hydroxy-2-methyl propyl)-4-piperidinyl]methyl}benzofuran-7-carboxamide L(+)-tartarate;

4-Amino-5-chloro-N-{[3-(2-hydroxy-2-methyl propyl)-3-azabicyclo[3.1.0]hex-6-yl]methyl}benzofuran-7-carboxamide;

4-Amino-5-chloro-N-{[3-(2-hydroxy-2-methyl propyl)-3-azabicyclo[3.1.0]hex-6-yl]methyl}benzofuran-7-carboxamide L(+)-tartarate;

4-Amino-5-chloro-2-methyl-N-{[1-(2-hydroxy-2-methyl propyl)-4-piperidinyl]methyl}benzofuran-7-carboxamide;

4-Amino-5-chloro-2-methyl-N-{[1-(2-hydroxy-2-methyl propyl)-4-piperidinyl]methyl}benzofuran-7-carboxamide L(+)-tartarate;
4-Amino-5-chloro-2-methyl-N-{[4-fluoro-1-(2-hydroxy-2-methyl propyl)-4-piperidinyl]methyl}benzofuran-7-carboxamide;
4-Amino-5-chloro-2-methyl-N-{[4-fluoro-1-(2-hydroxy-2-methyl propyl)-4-piperidinyl]methyl}benzofuran-7-carboxamide L(+)-tartarate;
4-Amino-5-chloro-2-methyl-N-{[3-(2-hydroxy-2-methyl propyl)-3-azabicyclo[3.1.0]hex-6-yl]methyl}benzofuran-7-carboxamide;
5-Amino-6-chloro-N-{[1-(2-fluoro-2-methyl propyl)-4-piperidinyl]methyl}chroman-8-carboxamide;
5-Amino-6-chloro-N-{[1-(2-fluoro-2-methyl propyl)-4-fluoro-4-piperidinyl]methyl}chroman-8-carboxamide;
5-Amino-6-chloro-N-{[1-(2-fluoro-2-methyl propyl)-4-fluoro-4-piperidinyl]methyl}chroman-8-carboxamide L(+)-tartarate;
5-Amino-6-chloro-N-{[3-(3-hydroxy-2,2-dimethyl propyl)-3-azabicyclo[3.1.0]hex-6-yl]methyl}chroman-8-carboxamide;
5-Amino-6-chloro-N-{[3-(3-hydroxy-2,2-dimethyl propyl)-3-azabicyclo[3.1.0]hex-6-yl]methyl}chroman-8-carboxamide L(+)-tartarate;
4-Amino-5-chloro-2-methyl-N-{[1-(3-hydroxy-2,2-dimethyl propyl)-4-piperidinyl]methyl}benzofuran-7-carboxamide;
5-Amino-6-chloro-N-{[3-(3-methoxy-2,2-dimethyl propyl)-3-azabicyclo[3.1.0]hex-6-yl]methyl}chroman-8-carboxamide;
5-Amino-6-chloro-N-{[4-fluoro-1-(3-methoxy propyl)-4-piperidinyl]methyl}chroman-8-carboxamide;
4-Amino-5-chloro-N-{[3-(3-methoxypropyl)-3-azabicyclo[3.1.0]hex-6-yl]methyl}-2,3-dihydrobenzofuran-7-carboxamide;
4-Amino-5-chloro-N-{[3-(3-methoxypropyl)-3-azabicyclo[3.1.0]hex-6-yl]methyl}-2,3-dihydrobenzofuran-7-carboxamide oxalate;
4-Amino-5-chloro-N-{[3-(3-methoxy propyl)-3-azabicyclo[3.1.0]hex-6-yl]methyl}benzofuran-7-carboxamide;
4-Amino-5-chloro-N-{[3-(3-methoxy propyl)-3-azabicyclo[3.1.0]hex-6-yl]methyl}benzofuran-7-carboxamide hydrochloride;
4-Amino-5-chloro-2-methyl-N-{[3-(3-methoxy propyl)-3-azabicyclo[3.1.0]hex-6-yl]methyl}benzofuran-7-carboxamide;
4-Amino-5-chloro-2-methyl-N-{[3-(3-methoxy propyl)-3-azabicyclo[3.1.0]hex-6-yl]methyl}benzofuran-7-carboxamide hydrochloride;
4-Amino-5-bromo-N-{[3-(3-methoxypropyl)-3-azabicyclo[3.1.0]hex-6-yl]methyl}-2,3-dihydrobenzofuran-7-carboxamide oxalate; and
5-Amino-6-chloro-N-{[1-(2-fluoro ethyl)-4-piperidinyl] methyl}chroman-8-carboxamide.

DETAILED DESCRIPTION OF THE INVENTION

Figure 1:
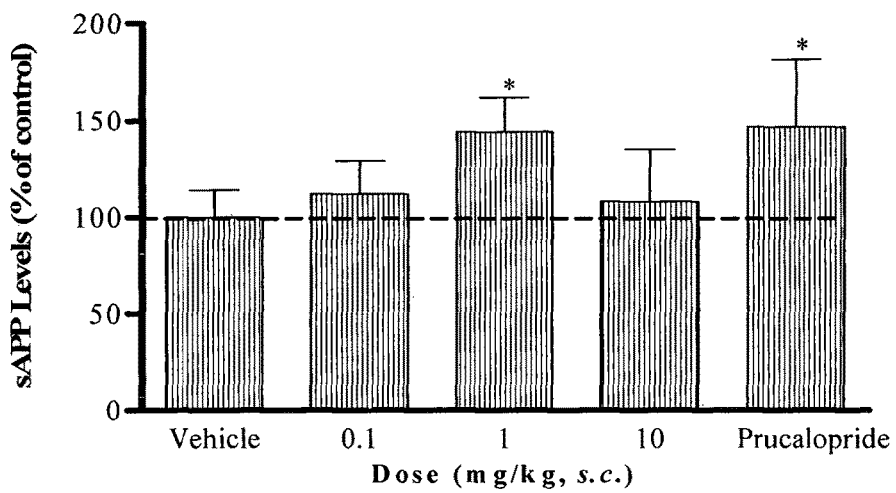
FIG. 1: Effect of test compound on mice brain cortical sAPPα levels

Unless otherwise stated, the following terms used in the specification and claims have the meanings given below:
The term "halogen" means fluorine, chlorine, bromine or iodine.
The term "agonist" means full agonist or partial agonist.
The phrase "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.
Commercial reagents were used without further purification. RT is defined as an ambient temperature range, typically from about 25° C. to about 35° C. Unless otherwise stated, all mass spectra were obtained using ESI conditions. $^1$H-NMR spectra were recorded at 400 MHz on a Bruker instrument. Deuterated chloroform, methanol or dimethylsulfoxide was used as solvent. TMS was used as internal reference standard. Chemical shift values are expressed in parts per million (δ) values. The following abbreviations are used for the multiplicity of the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.

EMBODIMENTS

The compounds of formula (I) may involve below mentioned embodiments. It is to be understood that the embodiments below are illustrative of the present invention and are not intended to limit the claims to the specific embodiment's exemplied.
According to one embodiment, there is provided a compound of formula (Ia):

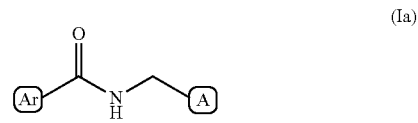

(Ia)

or their stereoisomers and pharmaceutically acceptable salts thereof,
wherein,

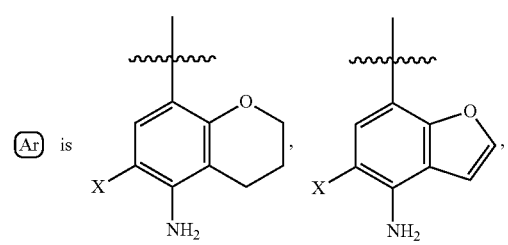

-continued

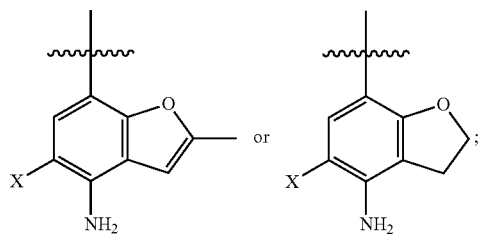 or

X is chlorine, bromine or hydrogen;

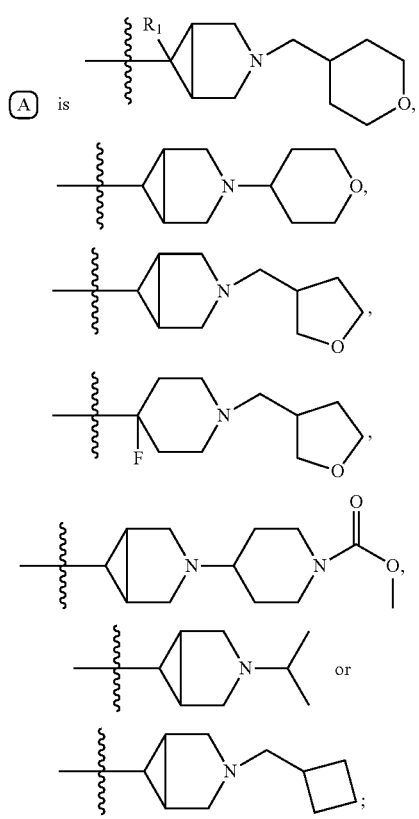

"⁀⁀⁀" is point of attachment;
R₁ is hydrogen, fluorine or hydroxyl.

According to another embodiment, there is provided a compound of the formula (Ib-1), derived from compound of formula (I):

(Ib-1)

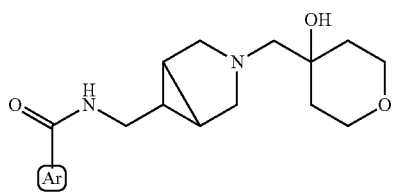

or their stereoisomers and pharmaceutically acceptable salts thereof, wherein,

Ⓐr is 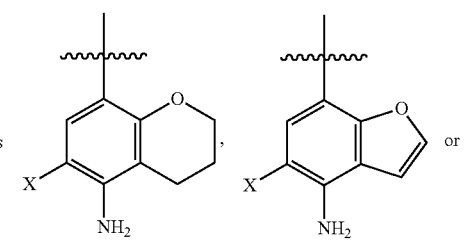 or

"⁀⁀⁀" is point of attachment;
X is chlorine.

According to another embodiment, there is provided a compound of the formula (Ib-2), derived from compound of formula (I):

(Ib-2)

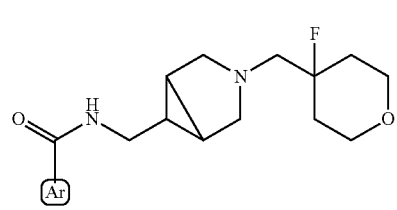

or their stereoisomers and pharmaceutically acceptable salts thereof, wherein,

Ⓐr is 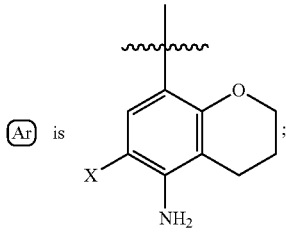

"⁀⁀⁀" is point of attachment;
X is chlorine.

According to another embodiment, there is provided a compound of the formula (Ic-1), derived from compound of formula (I):

(Ic-1)

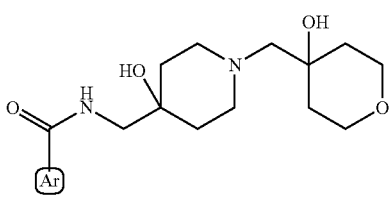

or their stereoisomers and pharmaceutically acceptable salts thereof,
wherein,

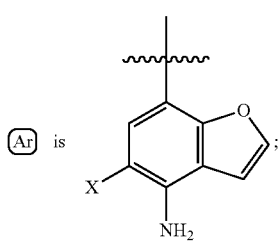 is

"∿∿∿" is point of attachment;
X is chlorine.

According to another embodiment, there is provided a compound of the formula (Id-1), derived from compound of formula (I):

(Id-1)

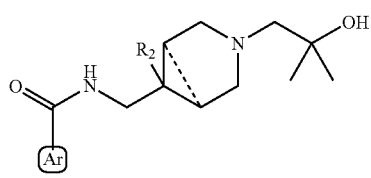

or their stereoisomers and pharmaceutically acceptable salts thereof,
wherein,
"--------" is a bond or no bond;

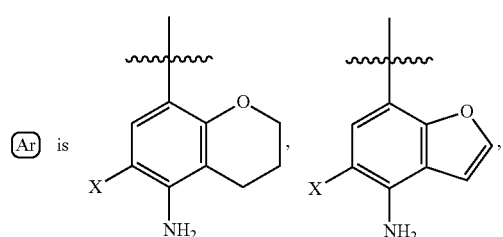 is

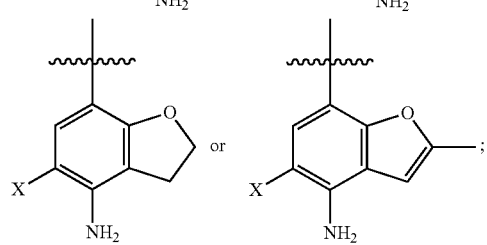

"∿∿∿" is point of attachment;
X is chlorine or bromine;
$R_2$ is hydrogen or fluorine.

According to another embodiment, there is provided a compound of the formula (Id-2), derived from compound of formula (I):

(Id-2)

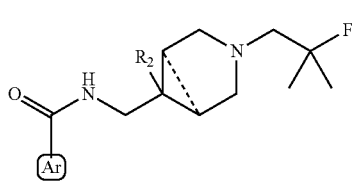

or their stereoisomers and pharmaceutically acceptable salts thereof,
wherein,
"--------" is a bond or no bond;

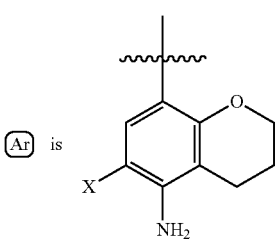 is

"∿∿∿" is point of attachment;
X is chlorine;
$R_2$ is hydrogen or fluorine.

According to another embodiment, there is provided a compound of the formula (Ie-1), derived from compound of formula (I):

(Ie-1)

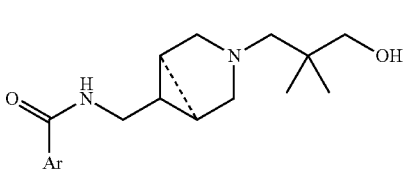

or their stereoisomers and pharmaceutically acceptable salts thereof,
wherein,
"--------" is bond or no bond;

Ar is

-continued

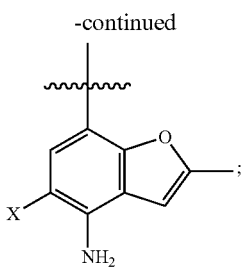

"∿∿∿" is point of attachment;
X is chlorine.

According to another embodiment, there is provided a compound of the formula (Ie-2), derived from compound of formula (I):

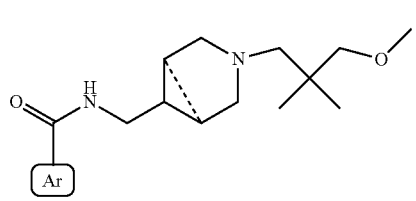

(Ie-2)

or their stereoisomers and pharmaceutically acceptable salts thereof,

"--------" is a bond or no bond;

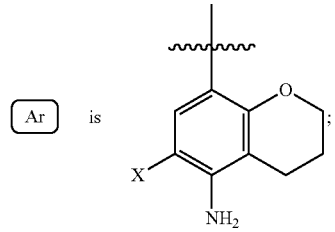

"∿∿∿" is point of attachment;
X is chlorine.

According to another embodiment, there is provided a compound of the formula (If-1), derived from compound of formula (I):

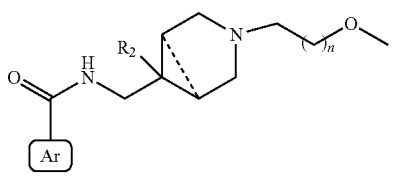

(If-1)

or their stereoisomers and pharmaceutically acceptable salts thereof, wherein,

"--------" is a bond or no bond;

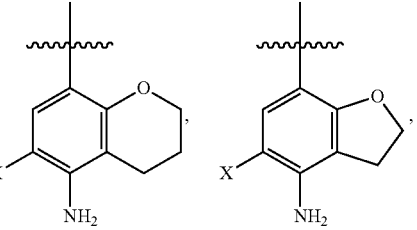

Ar is

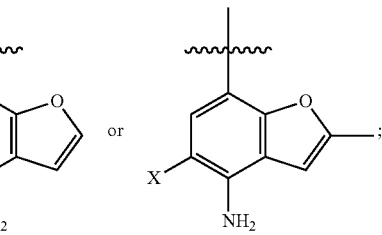

"∿∿∿" is point of attachment;
X is chlorine or bromine;
$R_2$ is hydrogen or fluorine.
"n" is 1 or 2.

According to another embodiment, there is provided a compound of the formula (If-2), derived from compound of formula (I):

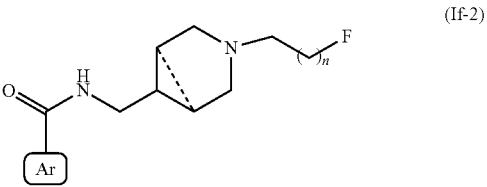

(If-2)

or their stereoisomers and pharmaceutically acceptable salts thereof,
wherein,

"--------" is a bond or no bond;

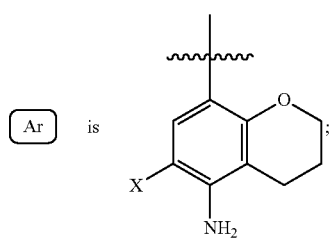

"∿∿∿" is point of attachment;
X is chlorine;
"n" is 1 or 2.

According to another embodiment, there is provided compound of formula (I), wherein:

Ar is

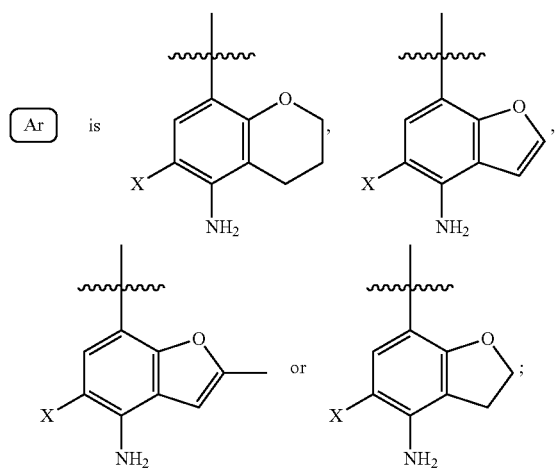

X is chlorine, bromine or hydrogen;

A is

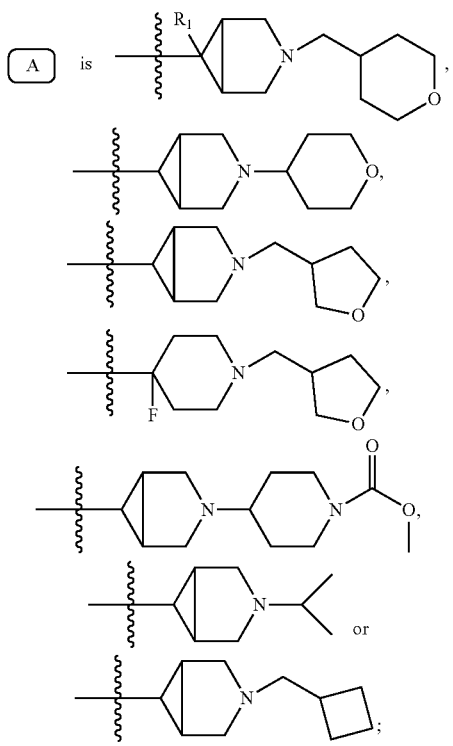

"⌇⌇⌇" is point of attachment;
$R_1$ is hydrogen.

According to another embodiment, there is provided compound of formula (I), wherein: $R_1$ is hydrogen.

Pharmaceutical Compositions

In order to use the compounds of formula (I), or their stereoisomers and pharmaceutically acceptable salts thereof in therapy, they will normally be formulated into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipient is carrier or diluent. Thus, the active compounds of the invention may be formulated for oral dosing. Such pharmaceutical compositions and processes for preparing same are well known in the art (The Science and Practice of Pharmacy, D. B. Troy, 21$^{st}$ Edition, Williams & Wilkins, 2006).

The dose of the active compounds can vary depending on factors such as age and weight of patient, nature and severity of the disease to be treated and such other factors. Therefore, any reference regarding pharmacologically effective amount of the compounds of general formula (I), stereoisomers thereof and pharmaceutically acceptable salts thereof refers to the aforementioned factors.

Methods of Preparation

The compounds of formula (I) can be prepared by using Schemes I to VI as shown below:

Scheme I:

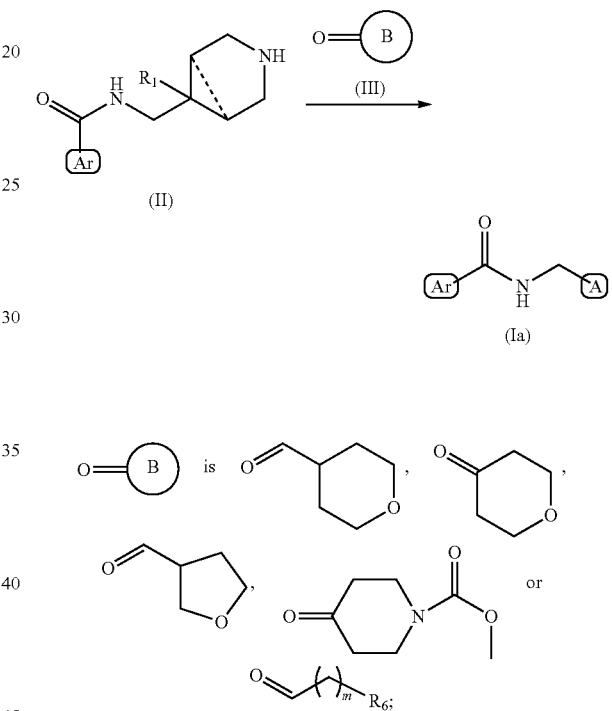

$R_1$ is hydrogen or fluorine;
m is 0 or 1;
"--------" is a bond or no bond;
$R_6$ is isopropyl or cyclobutyl.

In above Scheme I, all remaining symbols are as defined above.

The compounds of formula (Ia) are prepared according to Scheme I.

The compound of formula (II) is coupled with compound of formula (III) by reductive amination to form compound of formula (Ia). The reaction may be carried out in the presence of a reducing agent such as sodium triacetoxyborohydride, sodium bis(2-methoxyethoxy)aluminumhydride, sodium hydrosulfite, sodium borohydride, sodium cyanoborohydride, sodium dithionite or like and preferably by using sodium triacetoxyborohydride.

This reaction is preferably carried out in a solvent such as methanol, dichloroethane, dichloromethane, tetrahydrofuran, toluene, diethyl ether and the like or a mixture thereof and preferably by using dichloroethane or dichloromethane: The reaction is carried out at room temperature (RT). The duration of the reaction may range from 10 to 14 hours, preferably for the period of 11 to 13 hours.

The compounds of formula (II) may be prepared by using similar methods mentioned in the preparations 7, 8, 9, 11, 12, 15, 16 and 19.

The compounds of formula's (II) and (III) may be commercially available or can be prepared by conventional methods or by modification, using known process.

Scheme II:

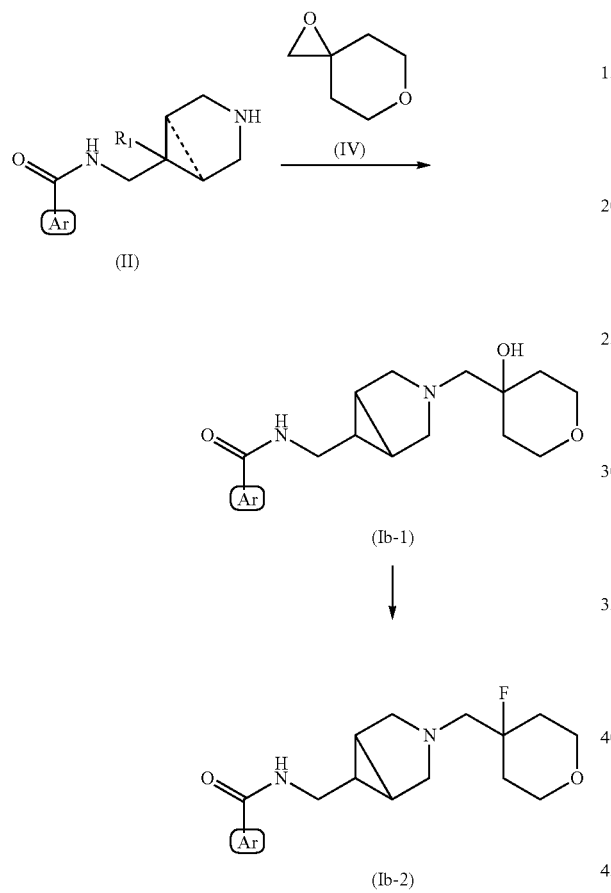

$R_1$ is hydrogen;

"--------" is a bond.

In Scheme II, Ar is as defined above.

The compounds of formula (Ib-1) and (Ib-2) are prepared according to Scheme II. The compound of formula (II) is coupled with compound (IV) to form compound of formula (Ib-1). This reaction is carried out in a solvent such as methanol, tetrahydrofuran, toluene, dimethylformamide, dimethyl sulfoxide, diethyl ether and the like or a mixture thereof and preferably by using methanol. The reaction may be carried out in the presence of a base such as triethylamine, potassium carbonate, diisopropylethylamine, pyridine and the like or a mixture thereof and preferably by using triethylamine. The reaction temperature may range from 70° C. to 86° C. based on the choice of solvent and preferably at a temperature in the range from 74° C. to 82° C. The duration of the reaction may range from 10 to 14 hours, preferably for the period of 11 to 13 hours.

The compound of formula (Ib-1) is converted to the compound of formula (Ib-2) in presence of diethylamino-sulfur trifluoride. This reaction is carried out in a solvent such as methanol, dichloroethane, dichloromethane, tetrahydrofuran, toluene, diethyl ether and the like or a mixture thereof and preferably by using dichloromethane. The reaction is carried out at RT. The duration of the reaction may range from 10 to 14 hours, preferably for the period of 11 to 13 hours.

The compounds of formula (II) may be prepared by using preparation 8, 12 and 19.

The compounds of formula's (II) and (IV) may be commercially available or can be prepared by conventional methods or by modification, using known process.

Scheme III:

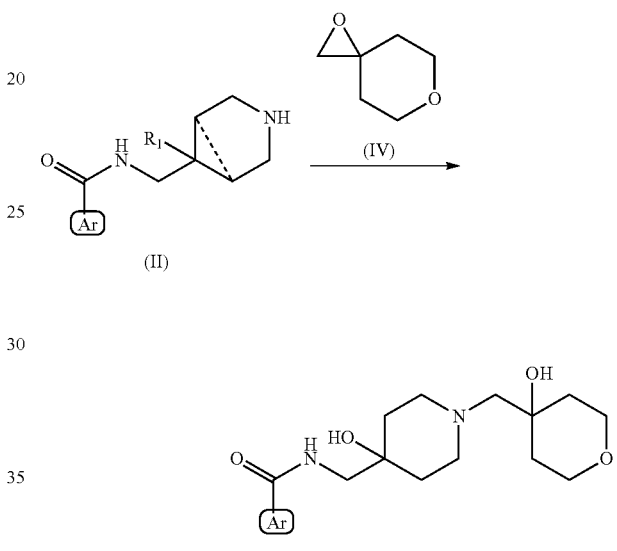

$R_1$ is hydroxy;

"--------" is no bond.

In Scheme III, Ar is as defined above.

The compounds of formula (Ic-1) are prepared according to Scheme III.

The compound of formula (II) is coupled with compound (IV) to form compound of formula (Ic-1). This reaction is carried out in a solvent such as methanol, tetrahydrofuran, toluene, dimethylformamide, dimethyl sulfoxide, diethyl ether and the like or a mixture thereof and preferably by using methanol. The reaction may be carried out in the presence of a base such as triethylamine, potassium carbonate, diisopropylethylamine, pyridine and the like or a mixture thereof and preferably by using triethylamine. The reaction temperature may range from 70° C. to 86° C. based on the choice of solvent and preferably at a temperature in the range from 74° C. to 82° C. The duration of the reaction may range from 10 to 14 hours, preferably for the period of 11 to 13 hours.

The compounds of formula (II) may be prepared by using preparation 14.

The compounds of formula's (II) and (IV) may be commercially available or can be prepared by conventional methods or by modification, using known process.

Scheme IV:

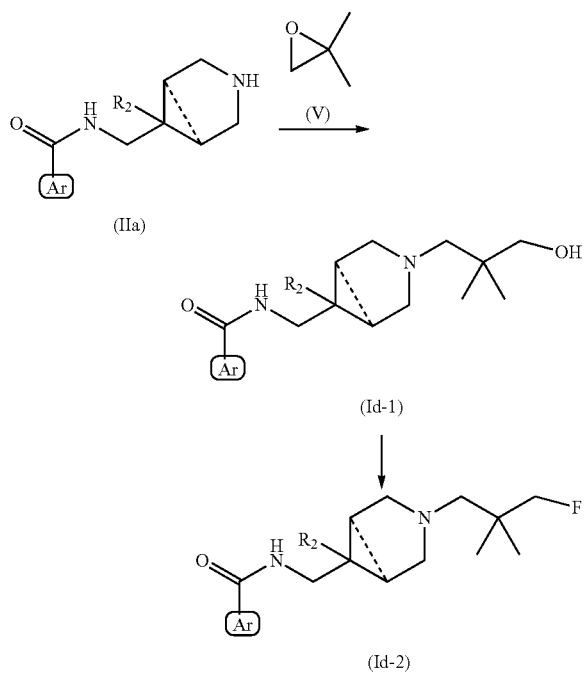

$R_2$ is hydrogen or fluorine;
In Scheme IV, all symbols are as defined above.

the like or a mixture thereof and preferably by using methanol. The reaction may be carried out in the presence of a base such as triethylamine, potassium carbonate, diisopropylethylamine, pyridine and the like or a mixture thereof and preferably by using triethylamine. The reaction temperature may range from 65° C. to 85° C. based on the choice of solvent and preferably at a temperature in the range from 70° C. to 80° C. The reaction is carried out at RT. The duration of the reaction may range from 10 to 14 hours, preferably for the period of 11 to 13 hours.

The compound of formula (Id-1) is fluorinated to form compound of formula (Id-2) in presence of diethylaminosulfur trifluoride. This reaction is carried out in a solvent such as methanol, dichloroethane, dichloromethane, tetrahydrofuran, toluene, diethyl ether and the like or a mixture thereof and preferably by using dichloromethane. The reaction is carried out at RT. The duration of the reaction may range from 10 to 14 hours, preferably for the period of 11 to 13 hours.

The compounds of formula (IIa) may be prepared by using similar methods used for the preparation 7, 8, 9, 11, 12, 13, 15, 16, 17 and 19.

The compounds of formula's (IIa) and (V) may be commercially available or can be prepared by conventional methods or by modification, using known process.

Scheme V:

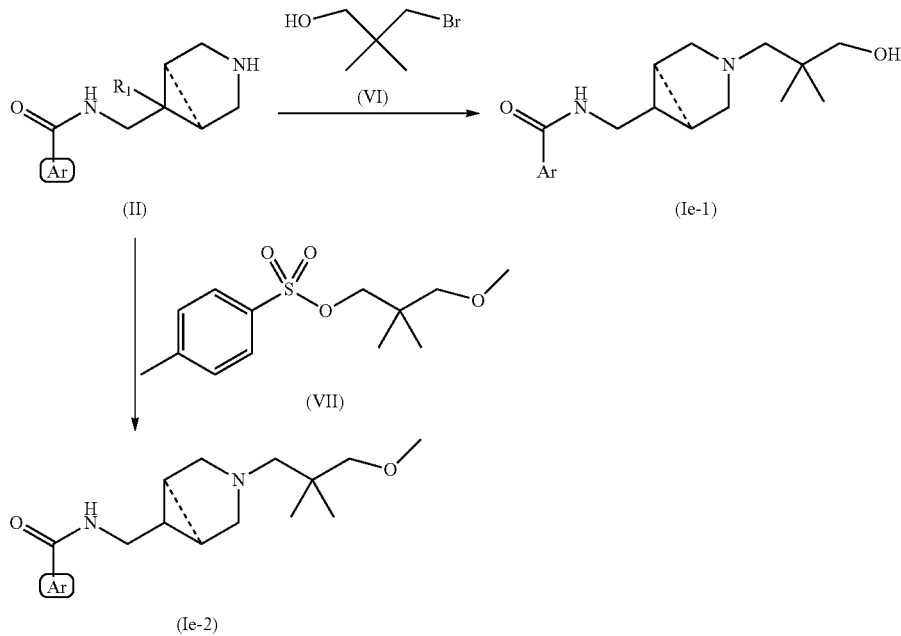

The compounds of formula (Id-1) and (Id-2) are prepared according to Scheme IV.

The compound of formula (IIa) is coupled with compound (V) to form compound of formula (Id-1). This reaction is carried out in a solvent such as methanol, dichloroethane, dichloromethane, tetrahydrofuran, toluene, diethyl ether and $R_1$ is hydrogen.
In Scheme V, all symbols are as defined above.

The compounds of formula (Ie-1) and (Ie-2) are prepared according to Scheme V. The compound of formula (II) is coupled with compound (VI) to form compound of formula (Ie-1). This reaction is carried out in a solvent such as acetonitrile, methanol, tetrahydrofuran, toluene, diethyl ether and the like or a mixture thereof and preferably by using acetonitrile. The reaction may be carried out in the presence of a base such as sodium hydroxide, potassium hydroxide, sodium carbonate, potassium carbonate and the like or a mixture thereof and preferably by using, potassium carbonate. The reaction temperature may range from 75° C. to 95° C. based on the choice of solvent and preferably at a temperature in the range from 80° C. to 90° C. The duration of the reaction may range from 10 to 14 hours, preferably for the period of 11 to 13 hours.

The compound of formula (II) is coupled with compound (VII) in presence of cesium carbonate and potassium iodide to form compound of formula (Ie-2). This reaction is carried out in a solvent such as dimethylformamide, methanol, dichloroethane, dichloromethane, tetrahydrofuran, toluene, diethyl ether and the like or a mixture thereof and preferably by using dimethylformamide. The reaction temperature may range from 110° C. to 130° C. based on the choice of solvent and preferably at a temperature in the range of 115° C. to 125° C. The duration of the reaction may range from 23 to 25 hours, preferably for the period of 24 hours.

The compounds of formula (II) may be prepared by using preparation 7, 8, 15 and 16.

The compound (VII) may be prepared by using preparation 20.

The compounds of formula (II) and compounds of (VI) and (VII) may be commercially available or can be prepared by conventional methods or by modification, using known process.

diethyl ether and the like or a mixture thereof and preferably by using acetonitrile. The reaction may be carried out in the presence of a base such as potassium bicarbonate, sodium triacetoxyborohydride, triethylamine, potassium carbonate, diisopropylethylamine, pyridine and the like or a mixture thereof and preferably by using potassium carbonate. The reaction temperature may range from 75° C. to 95° C. based on the choice of solvent and preferably at a temperature in the range from 82° C. to 88° C. The duration of the reaction may range from 4 to 8 hours, preferably for the period of 5 to 7 hours.

The compound of formula (IIa) is coupled with compound of formula (IX) to form compound of formula (X). This reaction is carried out in a solvent such as acetonitrile, methanol, dichloroethane, dichloromethane, tetrahydrofuran, toluene, dimethylformamide, dimethyl sulfoxide, diethyl ether and the like or a mixture thereof and preferably by using acetonitrile. The reaction may be carried out in the presence of a base such as potassium bicarbonate, triethylamine, potassium carbonate, diisopropylethylamine, pyridine and the like or a mixture thereof and preferably by using potassium bicarbonate. The reaction temperature may range from 75° C. to 95° C. based on the choice of solvent and preferably at a temperature in the range from 82° C. to 88° C. The duration of the reaction may range from 10 to 14 hours, preferably for the period of 11 to 13 hours.

The compound of formula (X) is fluorinated to form compound of formula (If-2) in presence of diethylaminosulfur trifluoride. This reaction is carried out in a solvent Scheme VI:

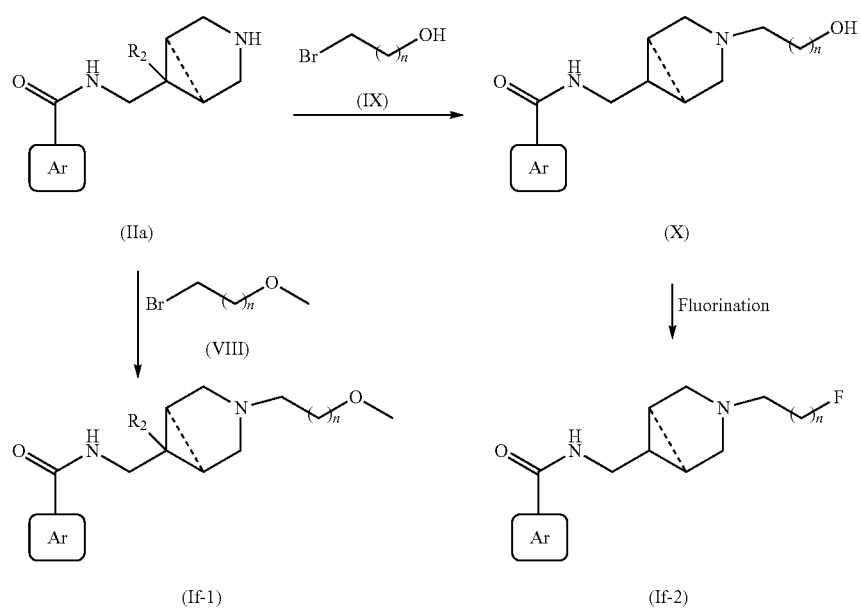

$R_2$ is hydrogen or fluorine.

In Scheme VI, all symbols are as defined above. The compounds of formula (If-1) and (If-2) are prepared according to Scheme VI.

The compound of formula (IIa) is coupled with compound of formula (VIII) to form compound of formula (If-1). This reaction is carried out in a solvent such as acetonitrile methanol, dichloroethane, dichloromethane, tetrahydrofuran, toluene, dimethylformamide, dimethyl sulfoxide, such as methanol, dichloroethane, dichloromethane, tetrahydrofuran, toluene, dimethylformamide, dimethyl sulfoxide, diethyl ether and the like or a mixture thereof and preferably by using dichloromethane. The reaction is carried out at RT. The duration of the reaction may range from 10 to 14 hours, preferably for the period of 11 to 13 hours.

The compounds of formula (IIa) may be prepared by using preparation 7, 8, 9, 11, 12, 15, 16 and 19.

The compounds of formula's (IIa), (VIII) and (IX) may be commercially available or can be prepared by conventional methods or by modification, using known process If necessary, pharmaceutically acceptable salts for compounds of formula (I) may be prepared conventionally by reaction with the appropriate acid or acid derivative.

Suitable pharmaceutically acceptable salts will be apparent to those skilled in the art and include those described in Journal of Pharmaceutical Science, 1977, 66, 1-19. The salts are formed with inorganic acids e. g. hydrochloric, hydrobromic, sulfuric, nitric & phosphoric acid or organic acids e.g., succinic, maleic, acetic, fumaric, citric, malic, tartaric, benzoic, p-toluic, p-toluenesulfonic, benzenesulfonic acid, methanesulfonic or naphthalenesulfonic acid. The most preferred salts of compounds of formula (I) are tartarates, fumarates, oxalates and hydrochlorides.

Certain compounds of formula (I) are capable of existing in stereoisomeric forms (e. g. diastereomers and enantiomers) and the invention extends to each of these stereoisomeric forms and to mixtures thereof including racemates. The different stereoisomeric forms may be separated from one another by the usual methods or any given isomer may be obtained by stereospecific or asymmetric synthesis. The invention also extends to tautomeric forms and mixtures thereof.

The stereoisomers as a rule are generally obtained as racemates that can be separated into the optically active isomers in a manner known per se. In the case of the compounds of general formula (I) having an asymmetric carbon atom the present invention relates to the D-form, the L-form and D,L-mixtures and in the case of compound of general formula (I) containing a number of asymmetric carbon atoms, the diastereomeric forms and the invention extends to each of these stereo isomeric forms and to mixtures thereof including racemates. Those compounds of general formula (I) which have an asymmetric carbon and as a rule are obtained as racemates can be separated one from the other by the usual methods, or any given isomer may be obtained by stereo specific or asymmetric synthesis. However, it is also possible to employ an optically active compound from the start, a correspondingly optically active enantiomeric or diastereomeric compound then being obtained as the final compound.

The stereoisomers of compounds of general formula (I) may be prepared by one or more ways presented below:
i) One or more of the reagents may be used in their optically active form.
ii) Optically pure catalyst or chiral ligands along with metal catalyst may be employed in the reduction process. The metal catalyst may be Rhodium, Ruthenium, Indium and the like. The chiral ligands may preferably be chiral phosphines (Principles of Asymmetric synthesis, J. E. Baldwin Ed., Tetrahedron series, 14, 311-316).
iii) The mixture of stereoisomers may be resolved by conventional methods such as forming diastereomeric salts with chiral acids or chiral amines or chiral amino alcohols, chiral amino acids. The resulting mixture of diastereomers may then be separated by methods such as fractional crystallization, chromatography and the like, which is followed by an additional step of isolating the optically active product by hydrolyzing the derivative (Jacques et. al., "Enantiomers, Racemates and Resolution", Wiley Interscience, 1981).
iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like. In the case of the compounds of general formula (I) containing geometric isomerism the present invention relates to all of these geometric isomers.

EXAMPLES

The compounds of the present invention were prepared according to the following experimental procedures, using appropriate materials and conditions.

Preparation 1: Preparation of
5-Amino-6-chloro-chroman-8-carboxylic Acid

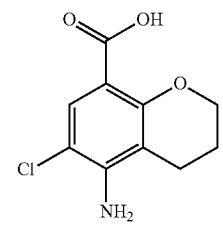 [SMILES: Nc1c(Cl)cc(C(=O)O)c2c1CCCO2]

Step (i): Preparation of Methyl 4-amino-2-hydroxy benzoate

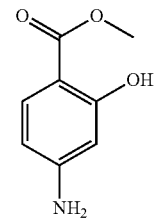

Sulfuric acid (H$_2$SO$_4$) (200 mL) was added drop wise to a stirred solution of 4-amino-2-hydroxy benzoic acid (100 grams, 0.653 mole) in methanol (MeOH) (1500 mL) at 0° C. Then reaction mass was slowly heated with stirring to 80° C. and stirred for 6 hours at the same temperature, while monitoring the progress of the reaction by thin layer chromatography (TLC). The reaction mass was cooled to room temperature (RT) and MeOH was evaporated. The residue was dissolved in water and the pH was adjusted to ~7 by using sodium hydroxide (NaOH) solution. The solid obtained was filtered. The solid mass was dissolved in dichloromethane (DCM) (2000 mL) and washed with brine solution (500 mL). The organic phase was dried over sodium sulfate (Na$_2$SO$_4$) and concentrated under vacuum to obtain the title compound.

Weight: 98.3 grams (Yield: 90%).

$^1$H-NMR (δ ppm): 3.76 (3H, s), 5.97-5.98 (1H, d, J=1.88 Hz), 6.08-6.12 (3H, m), 7.42-7.44 (1H, d, J=8.72 Hz), 10.75 (1H, s);

Mass (m/z): 168.1 (M+H)$^+$.

Step (ii): Preparation of Methyl 4-acetylamino-2-hydroxy benzoate

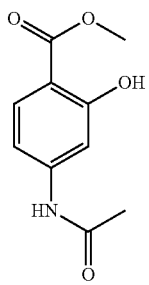

Acetic anhydride (Ac$_2$O) (66.50 mL, 0.704 mole) was added drop wise to a stirred solution of methyl 4-amino-2-hydroxy benzoate (98 grams, 0.586 mole, obtained in the above step) in DCM (980 mL) at 0° C. Then reaction mass was slowly brought to 10° C. and stirred for 4 hours at the same temperature, while monitoring the progress of the reaction by TLC. Reaction mass was poured into chilled water (1000 mL) and stirred for 30 minutes. The solid obtained was filtered and dissolved in ethyl acetate (EtOAc) (1000 mL). The organic phase was washed with brine solution (500 mL), dried over Na$_2$SO$_4$ and concentrated under vacuum to obtain the title compound.

Weight: 88.8 grams (Yield: 72.4%).

$^1$H-NMR (δ ppm): 2.03 (3H, s), 3.82 (3H, s), 7.00-7.03 (1H, dd, J=8.68, 1.60 Hz), 7.33-7.34 (1H, d, J=1.72 Hz), 7.66-7.68 (1H, d, J=8.72 Hz), 10.18 (1H, bs), 10.57 (1H, s);

Mass (m/z): 210.2 (M+H)$^+$.

Step (iii): Preparation of Methyl 4-acetylamino-5-chloro-2-hydroxy benzoate

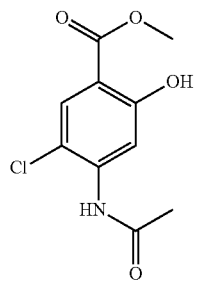 [SMILES: COC(=O)c1cc(Cl)c(NC(C)=O)cc1O]

N-Chlorosuccinimide (NCS) (69 grams, 0.509 mole) was added to a stirred solution of methyl 4-acetylamino-2-hydroxy benzoate (88.8 grams, 0.424 mole, obtained in the above step) in 1,2-dichloroethane (2 L) at RT. Reaction mass was slowly heated to 80° C. and stirred further for 4 hours at the same temperature, while monitoring the progress of the reaction by TLC. The mass was cooled to RT and 1,2-dichloroethane was evaporated. The residue was diluted with water (1 L) and the solid obtained was filtered. The solid obtained was dissolved in DCM (2 L) and washed with brine solution (500 mL). The organic phase was dried over Na$_2$SO$_4$ and concentrated under vacuum to obtain the title compound.

Weight: 97 grams (Yield: 93.9%).

$^1$H-NMR (δ ppm): 2.15 (3H, s), 3.84 (3H, s), 7.72 (1H, s), 7.76 (1H, s), 9.48 (1H, bs), 10.49 (1H, s);

Mass (m/z): 244.1 (M+H)$^+$, 246.0 (M+H)$^+$.

Step (iv): Preparation of Methyl 4-acetylamino-5-chloro-2-(propargyloxy) benzoate

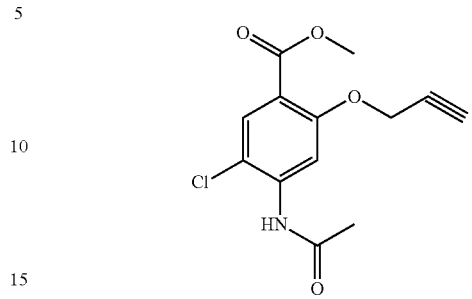

Propargyl bromide (53.57 mL, 0.479 mole) was added to a stirred solution of methyl 4-acetylamino-5-chloro-2-hydroxy benzoate (97 grams, 0.399 mole, obtained in the above step) and potassium carbonate (K$_2$CO$_3$) (110.17 grams, 0.798 mole) in dimethylformamide (DMF) (1 L) at 0° C. Then reaction mass was slowly allowed to rise to RT and stirred further for 28 hours at the same temperature, while monitoring the progress of the reaction by TLC. The mass was poured into chilled water (10 L) and stirred for 1 hour at RT. The resulting solid was filtered, washed with n-hexane (3×500 mL) and dissolved in EtOAc (3 L). The organic phase was washed with brine solution (500 mL), dried over Na$_2$SO$_4$ and concentrated under vacuum to obtain the title compound.

Weight: 99.6 grams (Yield: 88.64%).

$^1$H-NMR (δ ppm): 2.15 (3H, s), 3.62 (1H, s), 3.77 (3H, s), 4.81-4.82 (2H, d), 7.75 (1H, s), 7.90 (1H, s), 9.60 (1H, s);

Mass (m/z): 282.0 (M+H)$^+$, 284.1 (M+H)$^+$.

Step (v): Preparation of methyl 5-Acetylamino-6-chloro-2H-chromene-8-carboxylate

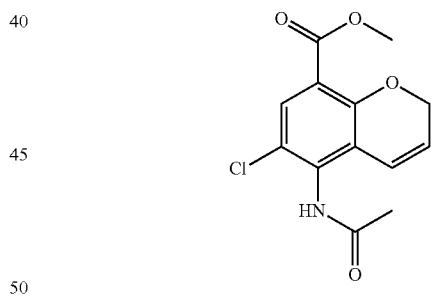

A stirred solution of methyl 4-acetylamino-5-chloro-2-propargyloxy benzoate (99 grams, 0.509 mole, obtained in the above step) in dowtherm (495 mL) was heated at 240° C. for 4 hours. The progress of the reaction was monitored by TLC. Reaction mass was cooled to 60° C. and poured into n-hexane (3.5 L) slowly and stirred for 1 hour. The solid obtained was filtered, dissolved in DCM (2 L) and washed with brine solution (500 mL). The organic phase was dried over Na$_2$SO$_4$ and concentrated under vacuum to obtain crude residue, which was further purified by flash chromatography using EtOAc:n-hexane (60:40) to afford the title compound.

Weight: 38.0 grams (Yield: 38.3%).

$^1$H-NMR (δ ppm): 2.06 (3H, s), 3.77 (3H, s), 4.82-484 (2H, m), 6.01-6.06 (1H, m), 6.40-6.43 (1H, m), 7.57 (1H, s), 9.77 (1H, s);

Mass (m/z): 282.0 (M+H)$^+$, 284.0 (M+H)$^+$.

Step (vi): Preparation of methyl 5-Acetylamino-6-chloro-2H-chroman-8-carboxylate

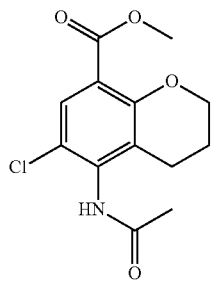 [SMILES: COC(=O)c1cc(Cl)c(NC(C)=O)c2c1OCCC2]

Hydrogen gas was passed into a stirred solution of methyl 5-acetylamino-6-chloro-2H-chromene-8-carboxylate (38 grams, 0.134 mole, obtained in the above step) and palladium hydroxide (19 grams, 50% w/w) in ethanol (540 mL) over a period of 4 hours, while monitoring the progress of the reaction by TLC. The reaction mass was filtered through celite bed and the filtrate was concentrated under vacuum to afford the title compound.

Weight: 34.7 grams (Yield: 90.69%).

$^1$H-NMR (δ ppm): 1.85-1.88 (2H, m), 2.06 (3H, s), 2.56-2.61 (2H, m), 3.76 (3H, s), 4.13-4.15 (2H, m), 7.54 (1H, s), 9.65 (1H, s);

Mass (m/z): 284.1 (M+H)$^+$, 286.1 (M+H)$^+$.

Step (vii): Preparation of 5-Amino-6-chloro chroman-8-carboxylic acid

Methyl 5-acetylamino-6-chloro-2H-chroman-8-carboxylate (34.7 grams, 0.122 mole, obtained in the above step) was added to a 1.7 N NaOH solution (861 mL) at RT and stirred for 8 hours, while monitoring the progress of the reaction by TLC. The mass was cooled to 0° C. and acidified with 5N Hydrochloric acid to pH ~3. The solid obtained was filtered, dissolved in tetrahydrofuran (THF): EtOAc (20:80, 1 L) and washed with brine solution (200 mL). The organic phase was dried over Na$_2$SO$_4$ and concentrated under vacuum to obtain the title compound.

Weight: 25 grams (Yield: 89.79%).

$^1$H-NMR (δ ppm): 1.88-1.97 (2H, m), 2.49-2.52 (2H, m), 4.07-4.10 (2H, m), 5.75 (2H, bs), 7.47 (1H, s), 11.75 (1H, bs);

Mass (m/z): 228.1 (M+H)$^+$, 230.0 (M+H)$^+$.

Preparation 2: Preparation of 4-Amino-5-chloro benzofuran-7-carboxylic Acid

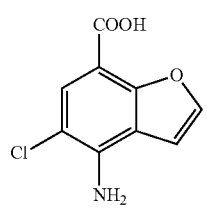 [SMILES: Nc1c(Cl)cc(C(=O)O)c2occc12]

Step (i): Preparation of Methyl 4-acetylamino-5-chloro-2-hydroxy-3-iodo benzoate

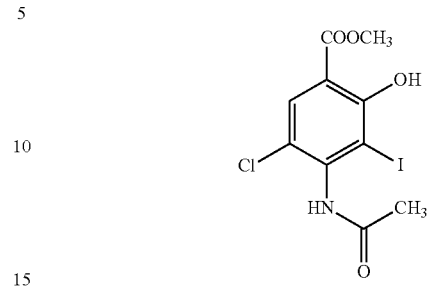

Benzyltrimethylammonium dichloroiodate (17.33 grams, 0.0498 mole) was added pinchwise to a stirred solution of methyl 4-acetylamino-5-chloro-2-hydroxy benzoate (12.13 grams, 0.0498 mole, obtained in the above step (iii) of preparation 1) and sodium bicarbonate (NaHCO$_3$) (10.46 grams, 0.124 mole) in a mixture of DCM and MeOH (120 mL:50 mL) at RT. The reaction mass was stirred for 18 hours and the solvent was evaporated under vacuum. The residue was poured into chilled water (500 mL) and stirred for 1 hour. The solid obtained was dissolved in chloroform (500 mL) and washed with sodium metabisulphite solution (3×250 mL). The organic phase was dried over Na$_2$SO$_4$ and concentrated under vacuum to obtain the title compound.

Weight: 15.8 grams (Yield: 85.8%).

$^1$H-NMR (δ ppm): 2.05 (3H, s), 3.92 (3H, s), 7.78 (1H, s), 9.98 (1H, s), 11.29 (1H, bs);

Mass (m/z): 370.1 (M+H)$^+$, 372.0 (M+H)$^+$.

Step (ii): Preparation of Methyl 4-acetylamino-5-chloro-2-trimethylsilanyl benzofuran-7-carboxylate

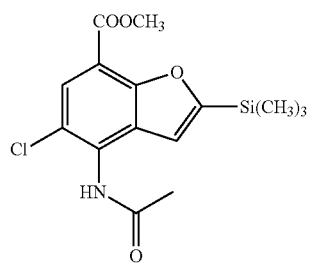

A solution of methyl 4-acetylamino-5-chloro-2-hydroxy-3-iodo benzoate (15.8 grams, 0.0427 mole, obtained in the above step), trimethylsilylacetylene, copper(I) iodide and trans-Bis(triphenylphosphine)palladium(II) chloride in triethylamine (TEA) and 1,4-dioxane (10 mL:80 mL) were stirred for 6 hours at 70° C. Reaction mass was slowly cooled to RT and solvent was concentrated under vacuum, the resulting slurry was treated with a solution of 1,1,3,3-tetramethyl guanidine (10.09 grams, 0.0876 mole) in toluene (100 mL). The reaction mass was refluxed for 3 hours, cooled to RT and diluted with chloroform (400 mL). The undissolved inorganic solids were separated by filteration. The filterate was washed with water (250 mL). The organic phase was dried over Na$_2$SO$_4$ and concentrated under vacuum to obtain the crude residue, which was further purified by flash chromatography using EtOAc:n-hexane (20:80) to afford the title compound.

Weight: 4.0 grams (Yield: 69%).

$^1$H-NMR (δ ppm): 0.34 (9H, s), 2.14 (3H, s), 3.91 (3H, s), 7.06 (1H, s), 7.85 (1H, s), 10.12 (1H, s);

Mass (m/z): 340.3 (M+H)$^+$, 342.2 (M+H)$^+$.

Step (iii): Preparation of 4-Amino-5-chloro benzofuran-7-carboxylic Acid

Potassium hydroxide (2.3 grams, 0.029 mole) was added pinchwise to the stirred solution of methyl 4-acetylamino-5-chloro-2-trimethylsilanyl benzofuran-7-carboxylate (4.0 grams, 0.011 mole, obtained in the above step) in a mixture of water and 1,4 dioxane (20 mL:20 mL). The reaction mass was stirred for 18 hours at 70° C., cooled to RT, diluted with water (100 mL) and washed with EtOAc (2×50 mL). The aqueous layer was acidified with 5N HCl (pH≈4), the solid obtained was filtered and dried under high vacuum to afford the title compound.

Weight: 1.65 grams (Yield: 66.7%).

$^1$H-NMR (δ ppm): 6.63 (2H, bs), 7.21-7.22 (1H, d, J=2.07 Hz), 7.63 (1H, s), 7.88-7.89 (1H, d, J=2.00 Hz);

Mass (m/z): 210.2 (M–H+), 212.3 (M–H+).

Preparation 3: Preparation of 4-Amino-5-chloro-2-methyl benzofuran-7-carboxylic Acid

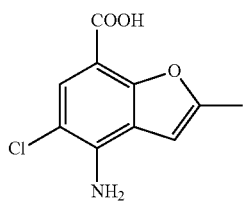

Step (i): Preparation of Methyl 4-acetylamino-5-chloro-2-methyl benzofuran-7-carboxylate

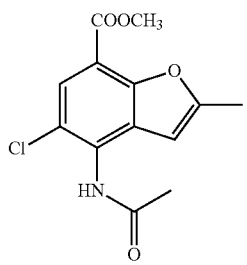 [SMILES: COC(=O)c1cc(Cl)c(NC(C)=O)c2cc(C)oc12]

A solution of methyl 4-acetylamino-5-chloro-2-propargyloxy benzoate (14.83 grams, 0.052 mole) in N-methylpyrrolidine was stirred for 5 hours at reflux temperature, while monitoring the progress of the reaction by TLC. The mass was cooled to RT and poured in chilled water (150 mL). The solution pH was adjusted to ~9.5 using 6N NaOH and the product was extracted with DCM (3×100 mL). The combined organic phase was washed with water (100 mL), brine solution (100 mL) and dried over Na$_2$SO$_4$. The organic phase was concentrated under vacuum to obtain a crude residue, which was further purified by flash chromatography using MeOH: EtOAc (10:90) to afford the title compound.

Weight: 11.77 grams (Yield: 79.36%).

$^1$H-NMR (δ ppm): 2.30 (3H, s), 2.51 (3H, s), 3.98 (3H, s), 6.45 (1H, s), 7.48 (1H, bs), 7.90 (1H, s);

Mass (m/z): 282.0 (M+H)$^+$, 284.0 (M+H)$^+$.

Step (ii): Preparation of 4-Amino-5-chloro-2-methyl benzofuran-7-carboxylic Acid Potassium hydroxide (3.2 grams, 0.057 moles) was added pinchwise to a stirred solution of methyl 4-acetylamino-5-chloro-2-methyl benzofuran-7-carboxylate (4.0 grams, 0.014 mole, obtained in the above step) in a mixture of water and 1,4-dioxane (15 mL:15 mL) and the reaction mass was heated to 85° C. for a period of 18 hours, while monitoring the progress of the reaction by TLC. The reaction mass was diluted with water (50 mL) and washed with EtOAc (2×25 mL). The aqueous phase was acidified with 5N HCl (pH≈4) and the obtained solids were filtered and dried under high vacuum to afford the title compound.

Weight: 2.93 grams (Yield: 91.56%).

$^1$H-NMR (δ ppm): 2.38 (3H, s), 6.43 (2H, bs), 6.77 (1H, s), 7.52 (1H, s), 12.43 (1H, bs);

Mass (m/z): 226.2 (M+H)$^+$, 228.0 (M+H)$^+$.

Preparation 4: Preparation of tert-butyl 6-aminomethyl-3-azabicyclo[3.1.0]hexane-3-carboxylate

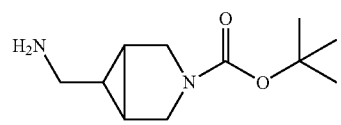

Step (i): Preparation of (3-Azabicyclo[3.1.0]hex-6-yl) methanol

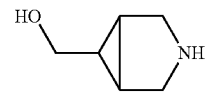

Hydrogen gas was passed into a stirred solution of (3-benzyl-3-azabicyclo[3.1.0]hex-6-yl)methanol (15.50 grams, 0.076 mole) and palladium hydroxide (7.75 grams, 50% w/w) in MeOH (150 mL) over a period of 6 hours, while monitoring the progress of the reaction by TLC. The reaction mass was filtered through celite bed and the filtrate was concentrated under vacuum to afford the title compound.

Weight: 8.20 grams (Yield: 69%).

$^1$H-NMR (δ ppm): 0.89-0.96 (1H, m), 1.35-1.42 (2H, m), 2.05-2.07 (2H, m), 2.85-2.88 (2H, m), 2.98-3.01 (2H, m), 3.50-3.52 (1H, m), 3.94-3.96 (1H, m);

Mass (m/z): 114.3 (M+H)$^+$.

Step (ii): Preparation of tert-butyl 6-hydroxymethyl-3-azabicyclo[3.1.0]hexane-3-carboxylate

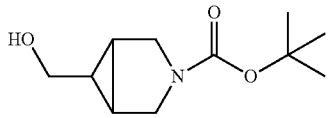

Di-tert-butyl dicarbonate (16.96 grams, 0.077 mole) was added to a solution of (3-aza bicyclo[3.1.0]hex-6-yl) methanol (8.00 grams, 0.07 mole, obtained in the above step) and TEA (11.40 grams, 0.112 mole) in DCM (150 mL) at 10° C. The reaction mass was stirred for 2 hours at 10° C., while monitoring the progress of the reaction by TLC. The reaction mass was washed with chilled water (50 mL), brine solution (50 mL) and dried over Na$_2$SO$_4$. The organic phase was concentrated under vacuum to obtain a crude residue, which was further purified by flash chromatography using EtOAc: n-hexane (50:50) to afford the title compound.

Weight: 7.84 grams (Yield: 52%).

$^1$H-NMR (δ ppm): 0.92-0.97 (1H, m), 1.33-1.36 (1H, m), 1.43 (9H, s), 1.55-1.60 (2H, m), 3.32-3.37 (2H, m), 3.43-3.48 (1H, m), 3.53-3.58 (2H, m), 3.61-3.64 (1H, m);

Mass (m/z): 214.2 (M+H)$^+$.

Step (iii): Preparation of tert-butyl 6-methanesulfonyloxymethyl-3-azabicyclo[3.1.0]hexane-3-carboxylate

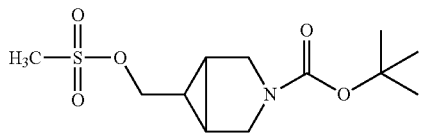 [SMILES: CC(C)(C)OC(=O)N1CC2C(COS(C)(=O)=O)C2C1]

A solution of methanesulfonyl chloride (4.42 grams, 0.038 mole) in DCM (25 mL) was added to a solution of tert-butyl 6-hydroxymethyl-3-azabicyclo[3.1.0]hexane-3-carboxylate (7.80 grams, 0.036 mole, obtained in the above step) and TEA (5.58 grams, 0.055 mole) in DCM (100 mL) at 0° C. The reaction mass was stirred overnight at RT, while monitoring the progress of the reaction by TLC. The reaction mass was washed with chilled water (50 mL), brine solution (50 mL) and dried over Na$_2$SO$_4$. The organic phase was concentrated under vacuum to afford the title compound.

Weight: 9.30 grams (Yield: 87%).

$^1$H-NMR (δ ppm): 1.11-1.15 (1H, m), 1.40-1.42 (1H, m), 1.45 (9H, s), 3.05 (3H, s), 3.17-3.19 (1H, m), 3.37-3.41 (2H, m), 3.58-3.68 (2H, m), 4.09-4.18 (2H, m);

Step (iv): Preparation of tert-butyl 6-Azidomethyl-3-azabicyclo[3.1.0]hexane-3-carboxylate

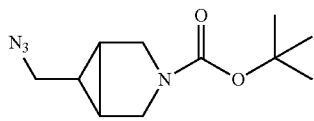 [SMILES: CC(C)(C)OC(=O)N1CC2C(CN=[N+]=[N-])C2C1]

Sodium azide (7.30 grams, 0.112 mole) was added to a solution of tert-butyl 6-methanesulfonyloxymethyl-3-azabicyclo[3.1.0]hexane-3-carboxylate (9.30 grams, 0.039 mole, obtained in the above step) and potassium carbonate (11.00 grams, 0.079 mole) in DMF (100 mL) at 10° C. Then the reaction mass was stirred over night at RT, and poured onto chilled water (200 mL). The product was extracted with EtOAc (3×150 mL) and the combined organic phase was washed with chilled water (150 mL), brine solution (150 mL) and dried over Na$_2$SO$_4$. The organic phase was concentrated under vacuum to afford the title compound.

Weight: 7 grams (Yield: 90%).

$^1$H-NMR (δ ppm): 0.97-1.00 (1H, m), 1.45 (9H, s), 1.50-1.53 (2H, m), 3.10-3.15 (1H, m), 3.22-3.27 (1H, m), 3.35-3.39 (2H, m), 3.57-3.67 (2H, m);

Step (v): Preparation of tert-butyl 6-aminomethyl-3-azabicyclo[3.1.0]hexane-3-carboxylate A solution of tert-butyl 6-azidomethyl-3-azabicyclo [3.1.0]hexane-3-carboxylate (1.50 grams, 0.006 mole, obtained in the above step) in THF (30 mL) and water (3 mL) mixture was treated with triphenylphosphine (2.1 grams, 0.008 mole). The reaction mass was stirred for 36 hours at RT and concentrated under vacuum to obtain a crude residue, which was further purified by flash chromatography using TEA:MeOH:DCM (2:8:90) to afford the title compound.

Weight: 1.20 grams (Yield: 90%).

$^1$H-NMR (δ ppm): 0.66-0.70 (1H, m), 0.95-0.99 (1H, t), 1.17-1.19 (1H, m), 1.33 (9H, s), 1.53-1.55 (2H, m), 2.67-2.69 (2H, m), 3.36-3.41 (2H, m), 7.73 (2H, bs);

Mass (m/z): 213.3 (M+H)$^+$.

Preparation 5: Preparation of tert-Butyl 4-aminomethyl-4-fluoro piperidine-1-carboxylate

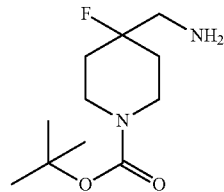 [SMILES: CC(C)(C)OC(=O)N1CCC(F)(CN)CC1]

Step (i): Preparation of tert-Butyl 1-oxa-6-aza spiro[2.5]octane-6-carboxylate

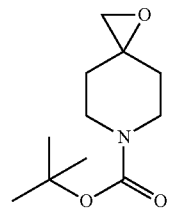

Trimethylsulfoxonium iodide (13.3 grams, 0.06 mole) was added to a stirred solution of sodium hydride (60% dispersion in oil, 3.0 grams, 0.126 mole) in THF (150 mL) at 10° C. Reaction mass temperature was slowly raised to RT and stirred further for 2 hours at the same temperature. Reaction mass was then cooled to 10° C. and added N-Boc piperidine-4-one (10 grams, 0.05 mole) solution in THF (50 mL) at the same temperature. Then reaction mass temperature was slowly raised to RT and stirred for 3 hours at same temperature and quenched onto chilled water (300 mL) and the compound was extracted with DCM (3×150 mL). The combined organic phase was washed with water (100 mL), brine solution (100 mL) and dried over $Na_2SO_4$. The organic phase was concentrated under vacuum to obtain the crude residue, which was further purified by flash chromatography using EtOAc:n-hexane (15:85) to afford the title compound.

Weight: 7.1 grams (Yield: 66%).

$^1$H-NMR (δ ppm): 1.47 (9H, s), 1.59-1.62 (2H, m), 1.76-1.83 (2H, m), 2.69 (2H, s), 3.39-3.45 (2H, m), 3.70-3.73 (2H, m); Mass (m/z): 214.3 $(M+H)^+$.

Step (ii): Preparation of tert-butyl 4-[(N,N-dibenzylamino)methyl]-4-hydroxy piperidine-1-carboxylate

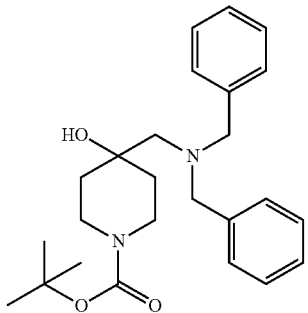 [SMILES: CC(C)(C)OC(=O)N1CCC(O)(CN(Cc2ccccc2)Cc2ccccc2)CC1]

Dibenzylamine (7.98 grams, 0.04 mole) was added to a stirred solution of tert-butyl 1-oxa-6-aza spiro[2.5]octane-6-carboxylate (7.86 grams, 0.036 mole, obtained in the above step) and TEA (11.19 grams, 0.118 mole) in MeOH (100 mL) at RT. Reaction mass temperature was slowly raised to 75° C. and stirred further for 38 hours at same temperature. After completion of the reaction, the reaction mass was concentrated under vacuum to obtain the crude residue, which was further purified by flash chromatography using EtOAc:n-hexane (15:85) to afford the title compound.

Weight: 7.1 grams (Yield: 46%).

$^1$H-NMR (δ ppm): 1.43 (9H, s), 1.89-1.94 (2H, m), 2.14-2.19 (1H, m), 2.55-2.60 (2H, m), 2.92 (1H, s), 3.03-3.09 (2H, m), 3.43-3.45 (1H, m), 3.64-3.67 (4H, m), 3.69-3.84 (2H, m), 7.16-7.35 (10H, m); Mass (m/z): 411.3 $(M+H)^+$ Step (iii): Preparation of tert-Butyl 4-[(N,N-dibenzylamino) methyl]-4-fluoro piperidine-1-carboxylate

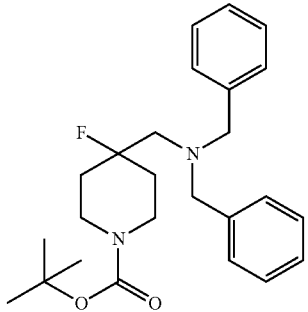 [SMILES: CC(C)(C)OC(=O)N1CCC(F)(CN(Cc2ccccc2)Cc2ccccc2)CC1]

Diethylaminosulfur trifluoride (DAST) (3.3 grams, 0.02 mole) was added to a stirred solution of tert-butyl 4-[(N,N-dibenzylamino) methyl]-4-hydroxy piperidine-1-carboxylate (7 grams, 0.017 mole, obtained in the above step) in DCM (70 mL) at −40° C. Then reaction mass temperature was slowly rised to RT and stirred over night at the same temperature. Reaction mass was quenched in chilled water (100 mL). The pH of the mass was adjusted to ~9.5 using aqueous ammonia and the compound was extracted with DCM (3×50 mL). The combined organic phase was washed with water (75 mL), brine solution (75 mL) and dried over $Na_2SO_4$. The organic phase was concentrated under vacuum to obtain the crude residue, which was further purified by flash chromatography using EtOAc:n-hexane (5:95) to afford the title compound.

Weight: 4.35 grams (Yield: 61%).

$^1$H-NMR (δ ppm): 1.45 (9H, s), 1.89-1.94 (2H, m), 2.14-2.19 (1H, m), 2.55-2.60 (2H, m), 3.03-3.09 (2H, m), 3.43-3.45 (1H, m), 3.64-3.67 (4H, m), 3.69-3.84 (2H, m), 7.16-7.35 (10H, m);

Mass (m/z): 413.3 $(M+H)^+$.

Step (iv): Preparation of tert-butyl 4-aminomethyl-4-fluoro piperidine-1-carboxylate Hydrogen gas was passed into a stirred solution of tert-butyl 4-[(N,N-dibenzylamino) methyl]-4-fluoro piperidine-1-carboxylate (1.37 grams, 3.28 mmole, obtained in the above step) and palladium hydroxide (1.37 grams, 50% w/w) in MeOH (30 mL) over a period of 8 hours. The progress of the reaction was monitored by TLC. After completion of the reaction, the reaction mass was filtered through celite bed and the filtrate was concentrated on rotavacuum to afford the title compound.

Weight: 0.66 grams (Yield: 85%).

$^1$H-NMR (δ ppm): 1.38 (9H, s), 1.44-1.71 (6H, m), 2.60-2.64 (2H, m), 2.95-3.04 (2H, m), 3.73-3.76 (2H, m);

Mass (m/z): 233.2 $(M+H)^+$.

Preparation 6: Preparation of t-Butyl 4-aminomethyl-4-hydroxy piperidine-1-carboxylate

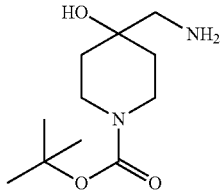 [SMILES: CC(C)(C)OC(=O)N1CCC(O)(CN)CC1]

tert-Butyl 1-oxa-6-azaspiro[2.5]octane-6-carboxylate (0.5 grams, 2.34 mmole, obtained in the step (i) of preparation 5) was added to methanolic ammonia solution (20 mL, 14.83% w/v) at RT. Then reaction mass was stirred for 40 hours at RT in a closed vessel. The reaction mass was concentrated under vacuum to obtain the title compound.

Weight: 0.41 gram (Yield: 76%).

$^1$H-NMR (δ ppm): 1.35-1.69 (16H, m), 2.61-2.69 (2H, m), 3.10-3.20 (2H, m), 3.81-3.90 (2H, m);

Mass (m/z): 231.3 $(M+H)^+$.

Preparation 7: Preparation of 5-Amino-6-chloro-N-(4-piperidinylmethyl)chroman-8-carboxamide

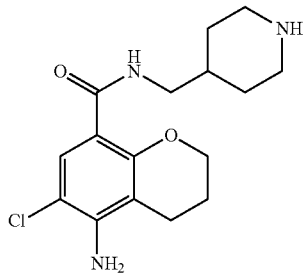 [SMILES: Nc1c(Cl)cc(C(=O)NCC2CCNCC2)c2c1CCCO2]

Step (i): Preparation of 5-Amino-6-chloro-N-{[1-(t-butoxycarbonyl)-4-piperidinyl] methyl} chroman-8-carboxamide

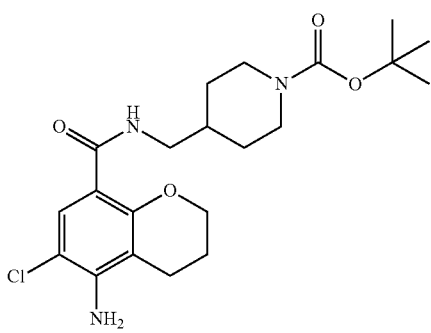 [SMILES: CC(C)(C)OC(=O)N1CCC(CNC(=O)c2cc(Cl)c(N)c3c2OCCC3)CC1]

A solution of 5-amino-6-chloro-chroman-8-carboxylic acid (0.40 gram, 1.758 mmole, obtained in the preparation 1) and carbonyldiimidazole (CDI) (0.427 gram, 2.637 mmole) in DCM (15 mL) was stirred for 2 hours at RT and a solution of tert-butyl 4-aminomethyl piperidine-1-carboxylate (0.45 gram, 2.109 mmole) in DCM (10 mL) was added. The reaction mass was stirred overnight (12 hours) at RT under nitrogen atmosphere and washed with chilled water (20 mL), brine solution (20 mL) and dried over $Na_2SO_4$. The organic phase was concentrated under vacuum to obtain the crude residue, which was further purified by flash chromatography using EtOAc:n-hexane (80:20) to afford the title compound.

Weight: 0.595 gram (Yield: 79.9%).

$^1$H-NMR (δ ppm): 1.21-1.29 (4H, m), 1.34 (9H, s), 1.51-1.70 (3H, m), 1.86-1.95 (2H, m), 2.41-2.46 (2H, m), 3.09-3.12 (2H, m), 3.86-3.92 (2H, m), 4.15-4.17 (2H, m), 5.55 (2H, bs), 7.53 (1H, s), 7.91-7.94 (1H, t); Mass (m/z): 424.2 (M+H)$^+$, 426.3 (M+H)$^+$.

Step (ii): Preparation of 5-Amino-6-chloro-N-(4-piperidinylmethyl)chroman-8-carboxamide Ethanolic hydrogen chloride (23% w/w, 0.508 gram, 13.93 mmole) was added to a solution of 5-amino-6-chloro-N-{[1-(t-butoxycarbonyl)-4-piperidinyl] methyl} chroman-8-carboxamide (0.59 gram, 1.393 mmole, obtained in the above step) in DCM (20 mL) at 10° C. The reaction mass was stirred overnight at RT. The reaction mass was concentrated and the slurry obtained was dissolved in chilled water (15 mL). The pH was adjusted to ~9.5 using aqueous ammonia solution and the product was extracted with DCM (3×100 mL). The combined organic phase was washed with water (10 mL), brine solution (10 mL), dried over $Na_2SO_4$ and concentrated under vacuum to afford the title compound.

Weight: 0.425 gram (Yield: 95%).

$^1$H-NMR (δ ppm): 1.20-1.30 (4H, m), 1.55-1.62 (3H, m), 1.91-1.98 (2H, m), 2.41-2.46 (3H, m), 2.91-2.99 (2H, m), 3.08-3.11 (2H, m), 4.15-4.17 (2H, m), 5.55 (2H, bs), 7.54 (1H, s), 7.90-7.93 (1H, t); Mass (m/z): 324.2 (M+H)$^+$, 326.3 (M+H)$^+$.

Preparation 8: Preparation of 5-Amino-6-chloro-N-{[3-azabicyclo[3.1.0]hex-6-yl] methyl}chroman-8-carboxamide

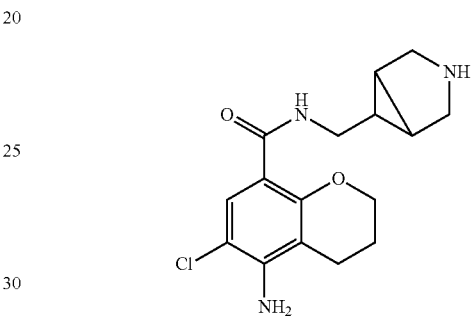

Step (i): Preparation of 5-Amino-6-chloro-N-{[3-(tert-butoxycarbonyl)-3-azabicyclo [3.1.0]hex-6-yl] methyl} chroman-8-carboxamide

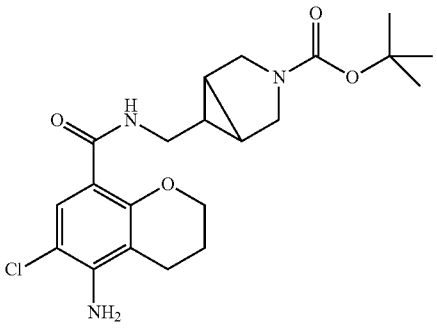 [SMILES: CC(C)(C)OC(=O)N1CC2C(CNC(=O)c3cc(Cl)c(N)c4c3OCCC4)C2C1]

A solution of 5-amino-6-chloro chroman-8-carboxylic acid (2.80 grams, 0.012 mole, obtained in the preparation 1) and CDI (2.79 grams, 0.017 mole) in DCM (280 mL) was stirred for 2 hours at RT. A solution of tert-butyl 6-aminomethyl-3-azabicyclo[3.1.0]hexane-3-carboxylate (3.13 grams, 0.013 mole, obtained in the preparation 4) in DCM (30 mL) was added at RT. The reaction mass was stirred overnight (12 hours) at RT. The reaction mass was washed with chilled water (50 mL), brine solution (50 mL), dried over $Na_2SO_4$ and the organic phase was concentrated under vacuum to obtain the crude residue, which was further purified by flash chromatography using EtOAc:n-hexane (30:70) to afford the title compound.

Weight: 3.68 grams (Yield: 71.04%).

¹H-NMR (δ ppm): 1.34 (9H, s), 1.43-1.55 (2H, m), 1.94-1.97 (2H, m), 2.44-2.49 (3H, m), 3.14-3.38 (6H, m), 4.18-4.21 (2H, m), 5.59 (2H, bs), 7.57 (1H, s), 8.02-8.05 (1H, t);

Mass (m/z): 422.2 (M+H)⁺, 424.2 (M+H)⁺.

Step (ii): Preparation of 5-Amino-6-chloro-N-{[3-azabicyclo[3.1.0]hex-6-yl]methyl}chroman-8-carboxamide Ethanolic hydrogen chloride (37% w/w, 3.18 gram, 87.12 mmole) was added to a stirred solution of 5-amino-6-chloro-N-{[3-(tert-butoxycarbonyl)-3-azabicyclo[3.1.0]hex-6-yl]methyl} chroman-8-carboxamide (3.68 grams, 8.73 mmole, obtained in the above step) in DCM (35 mL) at 10° C. The reaction mass was stirred overnight at RT. The reaction mass was concentrated and the slurry obtained was dissolved in water (45 mL), pH adjusted to ~9.5 using aqueous ammonia solution and extracted with DCM (3×25 mL). The combined organic phase was washed with water (25 mL), brine solution (25 mL) and dried over Na₂SO₄. The organic phase was concentrated under vacuum to afford the title compound.

Weight: 2.7 gram (Yield: 96.42%).

¹H-NMR (δ ppm): 1.22-1.30 (3H, m), 1.94-1.98 (2H, m), 2.43-2.79 (6H, m), 3.12-3.15 (2H, m), 3.30-3.35 (1H, m), 4.18-4.21 (2H, m), 5.60 (2H, bs), 7.59 (1H, s), 7.95-7.98 (1H, t); Mass (m/z): 322.3 (M+H)⁺, 324.3 (M+H)⁺.

Preparation 9: Preparation of 5-Amino-6-chloro-N-[(4-fluoro-4-piperidinyl) methyl] chroman-8-carboxamide

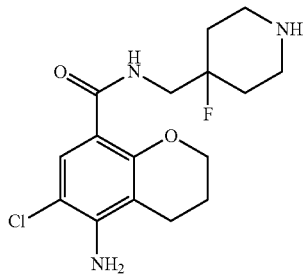

Step (i): Preparation of 5-Amino-6-chloro-N-{[4-fluoro-1-(tert-butoxycarbonyl)-4-piperidinyl]methyl} chroman-8-carboxamide

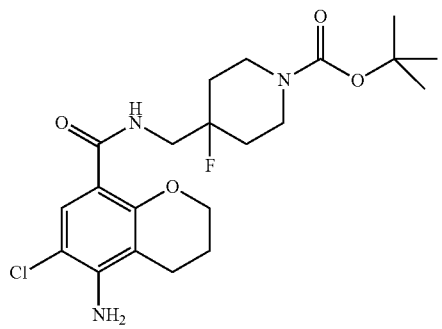 [SMILES: CC(C)(C)OC(=O)N1CCC(F)(CNC(=O)c2cc(Cl)c(N)c3c2OCCC3)CC1]

A solution of 5-amino-6-chloro-chroman-8-carboxylic acid (2 grams, 87.91 mmole, obtained in the preparation 1) and CDI (2.13 grams, 13.18 mmole) in DCM (100 mL) was stirred for 2 hours at RT. Then added a solution of tert-butyl 4-aminomethyl-4-fluoro piperidine-1-carboxylate (2.44 grams, 10.51 mmole, obtained in the preparation 5) in DCM (20 mL). The reaction mass was stirred overnight (12 hours) at RT under nitrogen atmosphere. After completion of the reaction, the reaction mass was washed with chilled water (50 mL), brine solution (50 mL) and dried over Na₂SO₄. The organic phase was concentrated on rotavacuum to obtain the crude residue, which was further purified by flash chromatography using EtOAc:n-hexane (30:70) to afford the title compound.

Weight: 0.73 grams (Yield: 47.16%).

¹H-NMR (δ ppm): 1.35 (9H, s), 1.49-1.66 (4H, m), 1.91-1.95 (2H, m), 2.42-2.46 (2H, m), 2.95-2.97 (2H, m), 3.46-3.53 (2H, m), 3.70-3.73 (2H, m), 4.16-4.18 (2H, m), 5.62 (2H, bs), 7.56 (1H, s), 7.99-8.02 (1H, t);

Mass (m/z): 442.3 (M+H)⁺, 444.2 (M+H)⁺.

Step (ii): Preparation of 5-Amino-6-chloro-N-[(4-fluoro-4-piperidinyl) methyl] chroman-8-carboxamide Ethanolic hydrogen chloride (20% w/w, 1.51 grams, 414.5 mmole) was added to a solution of 5-amino-6-chloro-N-{[4-fluoro-1-(t-butoxycarbonyl)-4-piperidinyl] methyl} chroman-8-carboxamide (1.83 grams, 41.44 mmole, obtained in the above step) in DCM (30 mL) at 10° C. The reaction mass was stirred overnight at RT, while monitoring the progress of the reaction by TLC. The reaction mass was concentrated and the slurry obtained was dissolved in chilled water (35 mL). The pH was adjusted to ~9.5 using aqueous ammonia solution and the product was extracted with DCM (3×20 mL). The combined organic phase was washed with water (20 mL), brine solution (20 mL) and dried over Na₂SO₄. The organic phase was concentrated under vacuum to afford the title compound.

Weight: 1.40 grams (Yield: 99%).

¹H-NMR (δ ppm): 1.56-1.70 (4H, m), 1.94-1.97 (2H, m), 2.42-2.49 (3H, m), 2.65-2.73 (4H, m), 3.45-3.53 (2H, m), 4.19-4.21 (2H, m), 5.64 (2H, bs), 7.61 (1H, s), 7.98-8.01 (1H, t);

Mass (m/z): 342.3 (M+H)⁺, 344.2 (M+H)⁺.

Preparation 10: Preparation of 5-Amino-6-chloro-N-[(4-hydroxy-4-piperidinyl) methyl] chroman-8-carboxamide

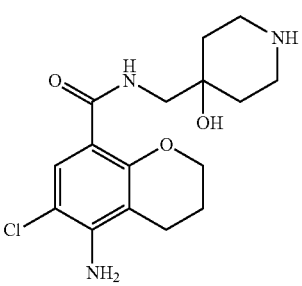 [SMILES: Nc1c(Cl)cc(C(=O)NCC2(O)CCNCC2)c2c1CCCO2]

Step (i): Preparation of 5-Amino-6-chloro-N-{[4-hydroxy-1-(tert-butoxycarbonyl)-4-piperidinyl]methyl} chroman-8-carboxamide

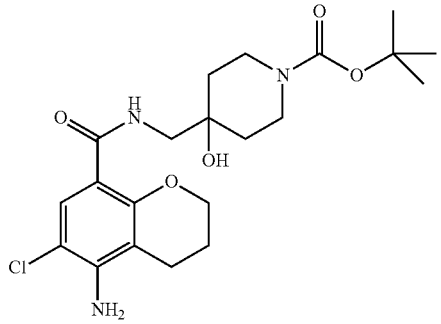 [SMILES: CC(C)(C)OC(=O)N1CCC(O)(CNC(=O)c2cc(Cl)c(N)c3c2OCCC3)CC1]

A solution of 5-amino-6-chloro chroman-8-carboxylic acid (0.200 grams, 0.878 mmole, obtained in the preparation 1) and carbonyldiimidazole (CDI) (0.170 grams, 1.054 mmole) in DCM (6 mL) was stirred for 2 hours at RT. Then a solution of tert-butyl 4-aminomethyl-4-hydroxy piperidine-1-carboxylate (0.222 grams, 0.967 mmole) in DCM (4 mL) was added. Reaction mass was stirred overnight at RT under nitrogen atmosphere. The reaction mass was washed with chilled water (10 mL), brine solution (10 mL) and dried over anhydrous sodium sulfate. The organic phase was concentrated on rotavacuum to obtain the crude residue, which was further purified by flash chromatography using EtOAc:n-hexane (30:70) to afford the title compound.

Weight: 0.266 grams (Yield: 69%).

$^1$H-NMR (δ ppm): 1.24-1.32 (4H, m), 1.36 (9H, s), 1.54-1.70 (2H, m), 1.87-1.95 (2H, m), 2.41-2.46 (2H, m), 3.09-3.13 (2H, m), 3.34-3.36 (2H, d), 3.86-3.94 (2H, m), 4.80 (1H, s), 5.56 (2H, bs), 7.54 (1H, s), 7.92-7.94 (1H, t);

Mass (m/z): 440.1 (M+H)$^+$, 442.3 (M+H)$^+$.

Step (ii): Preparation of 5-Amino-6-chloro-N-[(4-hydroxy-4-piperidinyl) methyl] chroman-8-carboxamide Ethanolic hydrogen chloride (30% w/w, 0.110 gram, 3.026 mmole) was added to a solution of 5-amino-6-chloro-N-{[4-hydroxy-1-(t-butoxycarbonyl)-4-piperidinyl]methyl}chroman-8-carboxamide (0.266 gram, 0.605 mmole, obtained in the above step) in DCM (10 mL) at 10° C. and the reaction mass was stirred for 2 hours at RT. The reaction mass was concentrated and the slurry obtained, was dissolved in chilled water (15 mL). The pH was adjusted to ~9.5 using aqueous ammonia and the product was extracted with dichloromethane (3×10 mL). The combined organic phase was washed with water (10 mL), brine solution (10 mL) and dried over sodium sulfate. The organic phase was concentrated under vacuum to afford the title compound.

Weight: 0.178 grams (Yield: 87%).

$^1$H-NMR (δ ppm): 1.26-1.34 (4H, m), 1.57-1.69 (2H, m), 1.90-1.99 (2H, m), 2.45-2.52 (2H, m), 3.08-3.11 (3H, m), 3.38-3.41 (2H, d), 3.88-3.98 (2H, m), 4.75 (1H, s), 5.65 (2H, bs), 7.58 (1H, s), 7.95-7.97 (1H, t);

Mass (m/z): 340.1 (M+H)$^+$, 342.4 (M+H)$^+$.

Preparation 11: Preparation of 4-Amino-5-chloro-N-(4-piperidinylmethyl) benzofuran-7-carboxamide

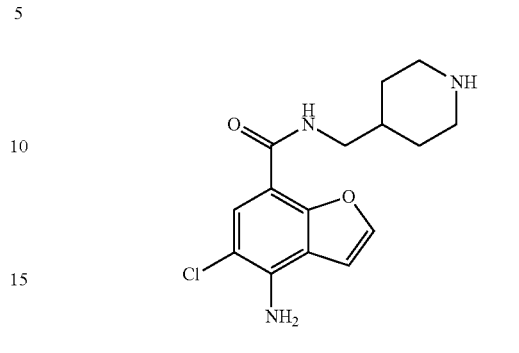

Step (i): Preparation of 4-Amino-5-chloro-N-[1-(t-butoxycarbonyl)-4-piperidinylmethyl] benzofuran-7-carboxamide

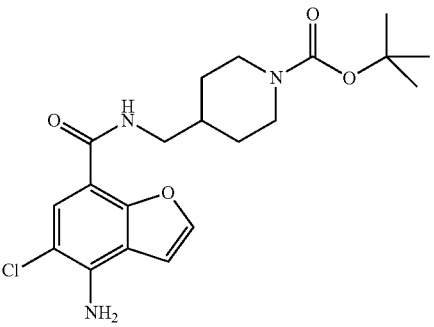 [SMILES: CC(C)(C)OC(=O)N1CCC(CNC(=O)c2cc(Cl)c(N)c3ccoc23)CC1]

A solution of 4-amino-5-chlorobenzofuran-7-carboxylic acid (0.50 gram, 2.362 mmole, obtained from preparation 2) and CDI (0.421 gram, 2.599 mmole) in DCM (3 mL) was stirred for 2 hours at RT. A solution of tert-butyl 4-aminomethyl piperidine-1-carboxylate (0.658 gram, 3.071 mmole) in DCM (2 mL) was added. The reaction mass was stirred overnight (12 hours) at RT under nitrogen atmosphere. After completion of the reaction, the reaction mass was washed with chilled water (20 mL), brine solution (20 mL) and dried over Na$_2$SO$_4$. The organic phase was concentrated on rotavacuum to obtain the crude residue, which was further purified by flash chromatography using EtOAc:n-hexane (50:50) to afford the title compound.

Weight: 0.611 gram (Yield: 64.3%).

$^1$H-NMR (δ ppm): 0.98-1.07 (2H, m), 1.37 (9H, s), 1.63-1.66 (2H, m), 1.71-1.75 (1H, m), 2.66-2.78 (2H, m), 3.18-3.21 (2H, m), 3.90-3.93 (2H, m), 6.41 (2H, bs), 7.24-7.25 (1H, d, J=1.96 Hz), 7.58 (1H, s), 7.79-7.82 (1H, t), 7.91 (1H, d, J=2.00 Hz);

Mass (m/z): 408.1 (M+H)$^+$, 410.1 (M+H)$^+$.

Step (ii): Preparation of 4-Amino-4-chloro-N-(4-piperidinylmethyl)benzofuran-7-carboxamide Ethanolic hydrogen chloride (23% w/w, 0.273 gram, 7.49 mmole) was added to a solution of 4-amino-5-chloro-N-[1-(t-butoxycarbonyl)-4-piperidinylmethyl]benzofuran-7-carboxamide (0.611 gram, 1.498 mmole, obtained in the above step) in DCM (20 mL) at 10° C. The reaction mass was stirred overnight at RT, concentrated and the slurry was dissolved in chilled water (15 mL). The pH was adjusted to ~9.5 using aqueous ammonia and the product was extracted with DCM (3×100 mL). The combined organic phase was washed with water (10 mL), brine solution (10 mL) and dried over $Na_2SO_4$. The organic phase was concentrated under vacuum to afford the title compound.

Weight: 0.415 gram (Yield: 90%).

$^1$H-NMR (δ ppm): 1.02-1.13 (2H, m), 1.60-1.66 (3H, m), 2.42-2.48 (2H, m), 2.86-2.96 (3H, m), 3.16-3.19 (2H, m), 6.41 (2H, bs), 7.25 (1H, d, J=1.77 Hz), 7.58 (1H, s), 7.74-7.77 (1H, t), 7.92 (1H, d, J=1.64 Hz);

Mass (m/z): 308.4 (M+H)$^+$, 310.0 (M+H)$^+$.

Preparation 12: Preparation of 4-Amino-5-chloro-N-{[3-azabicyclo[3.1.0]hex-6-yl]methyl}benzofuran-7-carboxamide

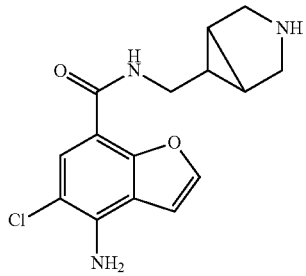 [SMILES: Nc1c(Cl)cc(C(=O)NCC2C3CNCC32)c2occc12]

Step (i): Preparation of 4-Amino-5-chloro-N-{[3-(tert-butoxycarbonyl)-3-azabicyclo [3.1.0]hex-6-yl]methyl}benzofuran-7-carboxamide

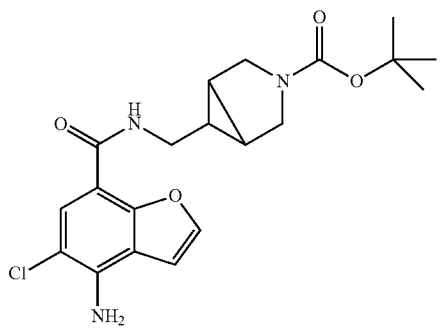 [SMILES: CC(C)(C)OC(=O)N1CC2C(CNC(=O)c3cc(Cl)c(N)c4ccoc34)C2C1]

A solution of 4-amino-5-chloro benzofuran-7-carboxylic acid (0.095 grams, 0.448 mmole, obtained in the preparation 2) and CDI (0.080 grams, 0.493 mmole) in dry THF (3 mL) was stirred for 1 hour at RT. Then a solution of tert-butyl 6-aminomethyl-3-aza bicyclo[3.1.0]hexane-3-carboxylate (0.095 grams, 0.448 mmole, obtained in the preparation 4) in dry THF (2 mL) was added at RT. The reaction mass was stirred overnight (12 hours) at RT under nitrogen atmosphere. After completion of the reaction (TLC), the reaction mass was concentrated and diluted with EtOAc (50 mL), washed with chilled water (15 mL), brine solution (15 mL) and dried over $Na_2SO_4$. The organic phase was concentrated on rotavacuum to obtain the crude residue, which was further purified by flash chromatography using EtOAc:n-hexane (30:70) to afford the title compound.

Weight: 0.131 grams (Yield: 72%).

$^1$H-NMR (δ ppm): 0.77-0.81 (1H, m), 1.18-1.19 (2H, m), 1.32 (9H, s), 3.18-3.21 (2H, m), 3.35-3.38 (2H, m), 6.40 (2H, bs), 7.22-7.23 (1H, d, J=2.10 Hz), 7.57 (1H, s), 7.85-7.88 (1H, t), 7.89-7.90 (1H, d, J=2.12 Hz);

Mass (m/z): 406.3 (M+H)$^+$, 408.3 (M+H)$^+$.

Step (ii): Preparation of 4-Amino-5-chloro-N-{[3-azabicyclo[3.1.0]hex-6-yl]methyl}benzofuran-7-carboxamide Ethanolic hydrogen chloride (23% w/w, 0.053 gram, 1.462 mmole) was added to a stirred solution of 4-amino-5-chloro-N-{[3-(tert-butoxycarbonyl)-3-azabicyclo[3.1.0] hex-6-yl]methyl} benzofuran-7-carboxamide (0.118 gram, 0.292 mmole, obtained in the above step) in ethanol (5 mL) at 10° C. The reaction mass was stirred overnight at RT. The reaction mass was concentrated and the slurry obtained was dissolved in water (1.5 mL). The pH was adjusted to ~9.5 using aqueous NH$_3$ solution and the product was extracted with DCM (3×10 mL). The combined organic phase was washed with water (10 mL) and brine solution (10 mL) and dried over $Na_2SO_4$. The organic phase was concentrated under vacuum to afford the title compound.

Weight: 0.075 gram (Yield: 84%).

$^1$H-NMR (δ ppm): 0.98-1.03 (1H, m), 1.27-1.29 (2H, m), 1.46-1.49 (1H, m), 2.91-2.94 (2H, m), 3.03-3.06 (2H, m), 3.47-3.51 (2H, m), 6.42 (2H, bs), 7.25-7.26 (1H, d, J=2.10 Hz), 7.59 (1H, s), 7.86-8.88 (1H, t), 7.91-7.92 (1H, d, J=2.12 Hz);

Mass (m/z): 306.2 (M+H)$^+$, 308.4 (M+H)$^+$.

Preparation 13: Preparation of 4-Amino-5-chloro-N-(4-fluoro-4-piperidinyl methyl)benzofuran-7-carboxamide

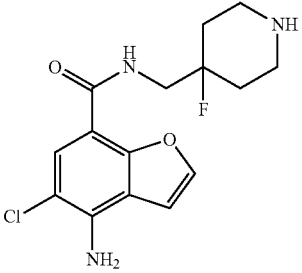 [SMILES: Nc1c(Cl)cc(C(=O)NCC2(F)CCNCC2)c2occc12]

Step (i): Preparation of 4-Amino-5-chloro-N-[4-fluoro-1-(tert-butoxycarbonyl)-4-piperidinyl methyl benzofuran-7-carboxamide

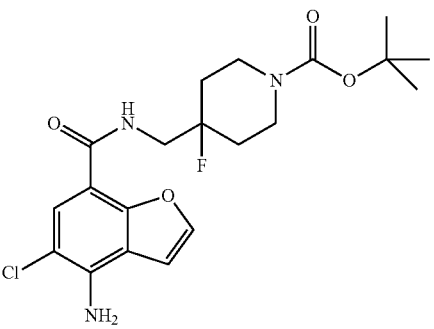 [SMILES: CC(C)(C)OC(=O)N1CCC(F)(CNC(=O)c2cc(Cl)c(N)c3ccoc23)CC1]

To a solution of 4-amino-5-chloro benzofuran-7-carboxylic acid (18.3 grams, 0.0866 mole, obtained in the preparation 2) in DMF (350 ml) was added CDI (17.8 grams, 0.109 mole) at RT and stirred for 8 hours. TLC showed absence of acid. A solution of tert-butyl 4-aminomethyl-4-fluoro piperidine-1-carboxylate (24.5 grams, 0.105 mole, obtained in the preparation 5) in DMF (50 mL) was added drop wise to the reaction mass. The reaction mass was stirred further for 18 hours at RT under nitrogen atmosphere and poured over 1800 mL ice cold water with stirring and stirred further for 40 minutes. The solid obtained was filtered and dried under vacuum to obtain crude compound (41.2 grams), which was further purified by flash chromatography using EtOAc:n-hexane (45:55) to afford the title compound.

Weight: 29.8 grams (Yield: 81%).

$^1$H-NMR ($\delta$ ppm): 1.37 (9H, s), 1.53-1.77 (4H, m), 2.99 (2H, bs), 3.55-3.62 (2H, dd), 3.73-3.77 (2H, d), 6.49 (2H, s), 7.26 (1H, d), 7.62 (1H, s), 7.80-7.83 (1H, t), 7.94 (1H, d);

Mass (m/z): 426.3 (M+H)$^+$, 428.3 (M+H)$^+$.

Step (ii): Preparation of 4-Amino-5-chloro-N-(4-fluoro-4-piperidinyl methyl)benzofuran-7-carboxamide Ethanolic hydrogen chloride (23% w/w, 0.541 mole) was added to a solution of 4-amino-5-chloro-N-[4-fluoro-1-(t-butoxycarbonyl)-4-piperidinylmethyl]benzofuran-7-carboxamide (28.8 grams, 0.0676 mole, obtained in the above step) in DCM (600 mL) at 10° C. The clear solution was stirred further for 18 hours at RT under nitrogen atmosphere while monitoring the progress of the reaction by TLC. The mass was concentrated to which 400 mL ice cold water was added and is basified to pH ~11 with aqueous ammonia at 10° C. and the product was extracted with DCM (3×250 mL). The combined organic phase was washed with water (500 mL), brine solution (500 mL) and dried over Na$_2$SO$_4$. The organic phase was concentrated under vacuum to afford the title compound.

Weight: 19.5 grams (Yield: 89%).

$^1$H-NMR ($\delta$ ppm): 1.48-1.67 (4H, m), 2.01-2.04 (1H, bs), 2.63-2.74 (4H, m), 3.52-3.58 (2H, dd), 6.49 (2H, s), 7.26-7.27 (1H, d; J=2 Hz), 7.63 (1H, s), 7.72-7.75 (1H, t), 7.95 (1H, d; J=2 Hz);

Mass (m/z): 326.1 (M+H)$^+$, 328.2 (M+H)$^+$.

Preparation 14: Preparation of 4-Amino-5-chloro-N-(4-hydroxy-4-piperidinylmethyl)benzofuran-7-carboxamide

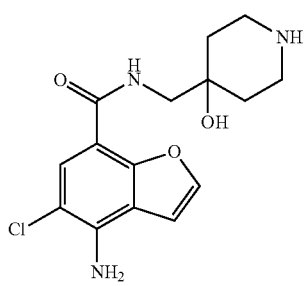

Step (i): Preparation of 4-Amino-5-chloro-N-[4-hydroxy-1-(tert-butoxycarbonyl)-4-piperidinyl methyl]benzofuran-7-carboxamide

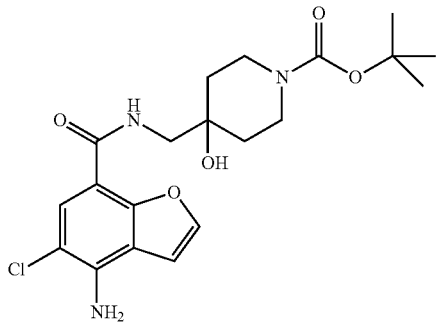 [SMILES: CC(C)(C)OC(=O)N1CCC(O)(CNC(=O)c2cc(Cl)c(N)c3ccoc23)CC1]

A solution of 4-amino-5-chloro benzofuran-7-carboxylic acid (0.050 grams, 0.236 mmole, obtained in the preparation 2) and CDI (0.042 grams, 0.259 mmole) in DCM (3 mL) was stirred for 2 hours at RT. Then added a solution of tert-butyl 4-aminomethyl-4-hydroxy piperidine-1-carboxylate (0.081 grams, 0.354 mmole, obtained in preparation 6) in DCM (2 mL). The reaction mass was stirred overnight (12 hours) at RT under nitrogen atmosphere, while monitoring the progress of the reaction by TLC. The reaction mass was washed with chilled water (10 mL) and brine solution (10 mL) and dried over anhydrous Na$_2$SO$_4$. The organic phase was concentrated on rotavacuum to obtain the crude residue, which was further purified by flash chromatography using EtOAc:n-hexane (70:30) to afford the title compound.

Weight: 0.064 grams (Yield: 64%).

$^1$H-NMR ($\delta$ ppm): 1.14-1.28 (2H, m), 1.36 (9H, s), 1.40-1.46 (2H, m), 3.08-3.11 (2H, m), 3.34-3.36 (2H, d), 3.59-3.62 (2H, m), 4.79 (1H, s), 6.47 (2H, bs), 7.2 (1H, d, J=1.95 Hz), 7.64 (1H, s), 7.66-7.69 (1H, t), 7.95 (1H, d, J=1.83 Hz);

Mass (m/z): 424.2 (M+H)$^+$, 426.3 (M+H)$^+$.

Step (ii): Preparation of 4-Amino-5-chloro-N-(4-hydroxy-4-piperidinylmethyl)benzofuran-7-carboxamide Ethanolic hydrogen chloride (30% w/w, 0.027 gram, 0.755 mmole) was added to a solution of 4-amino-5-chloro-N-[4-hydroxy-1-(tert-butoxycarbonyl)-4-piperidinyl methyl]benzofuran-7-carboxamide (0.064 gram, 0.151 mmole, obtained in the above step) in DCM (10 mL) at 10° C. The reaction mass was stirred overnight at RT. The reaction mass was concentrated and the slurry obtained was dissolved in chilled water (15 mL). The pH was adjusted to ~9.5 using aqueous ammonia and extracted with DCM (3×10 mL). The combined organic phase was washed with water (10 mL) and brine solution (10 mL) and dried over Na$_2$SO$_4$. The organic phase was concentrated under vacuum to afford the title compound.

Weight: 0.040 grams (Yield: 83%).

$^1$H-NMR ($\delta$ ppm): 1.66-1.69 (4H, m), 2.86-3.04 (4H, m), 3.49-3.53 (2H, m), 7.11 (1H, d; J=2.02 Hz), 7.80 (2H, m);

Mass (m/z): 324.2 (M+H)$^+$, 326.2 (M+H)$^+$.

Preparation 15: Preparation of 4-Amino-5-chloro-2-methyl-N-(4-piperidinylmethyl)benzofuran-7-carboxamide

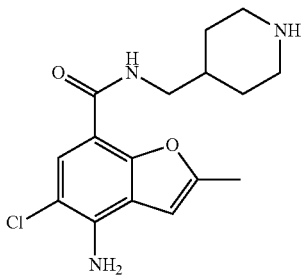 [SMILES: Cc1cc2c(N)c(Cl)cc(C(=O)NCC3CCNCC3)c2o1]

Step (i): Preparation of 4-Amino-5-chloro-2-methyl-N-[1-(t-butoxycarbonyl)-4-piperidinyl methyl]benzofuran-7-carboxamide

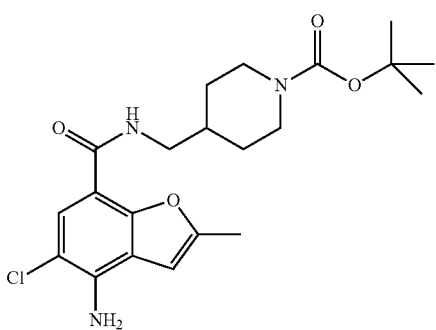

A solution of 4-amino-5-chloro-2-methyl benzofuran-7-carboxylic acid (0.300 gram, 1.330 mmole, obtained from preparation 3) and CDI (0.323 gram, 1.995 mmole) in DCM (6 mL) was stirred for 2 hours at RT and added a solution of tert-butyl 4-aminomethyl piperidine-1-carboxylate (0.341 gram, 1.596 mmole) in DCM (4 mL). The reaction mass was stirred overnight (12 hours) at RT under nitrogen atmosphere and washed with chilled water (20 mL) and brine solution (20 mL) and dried over Na$_2$SO$_4$. The organic phase was concentrated on rotavacuum to obtain the crude residue, which was further purified by flash chromatography using EtOAc:n-hexane (50:50) to afford the title compound.

Weight: 0.560 gram (Yield: 100%).
$^1$H-NMR (δ ppm): 1.19-1.29 (2H, m), 1.45 (9H, s), 1.75-1.78 (2H, m), 1.82-1.87 (1H, m), 2.50 (3H, s), 2.61-2.71 (2H, m), 2.43-2.48 (2H, m), 4.09-4.15 (2H, m), 4.52 (2H, bs), 6.37 (1H, s), 7.29-7.31 (1H, t), 7.95 (1H, s);
Mass (m/z): 422.3 (M+H)$^+$, 424.3 (M+H)$^+$.

Step (ii): Preparation of 4-Amino-5-chloro-2-methyl-N-(4-piperidinylmethyl)benzofuran-7-carboxamide Ethanolic hydrogen chloride (23% w/w, 0.259 gram, 7.11 mmole) was added to a solution of 4-amino-5-chloro-2-methyl-N-[[1-(t-butoxycarbonyl)-4-piperidinymethyl]benzofuran-7-carboxamide (0.60 gram, 1.423 mmole, obtained in the above step) in DCM (20 mL) at 10° C. The reaction mass was stirred overnight at RT and dissolved in chilled water (15 mL). The pH was adjusted to ~9.5 using aqueous ammonia solution and extracted with DCM (3×100 mL). The combined organic phase was washed with water (10 mL) and brine solution (10 mL) and dried over Na$_2$SO$_4$. The organic phase was concentrated under vacuum to afford the title compound.

Weight: 0.450 gram (Yield: 98%).
$^1$H-NMR (δ ppm): 1.02-1.13 (2H, m), 1.60-1.66 (3H, m), 2.42-2.48 (2H, m), 2.54 (3H, s), 2.86-2.96 (3H, m), 3.16-3.19 (2H, m), 4.54 (2H, bs), 6.41 (1H, s), 7.31-7.33 (1H, t), 7.96 (1H, s);
Mass (m/z): 322.4 (M+H)$^+$, 324.4 (M+H)$^+$.

Preparation 16: Preparation of 4-Amino-5-chloro-2-methyl-N-[(3-azabicyclo[3.1.0]hex-6-yl)methyl]benzofuran-7-carboxamide

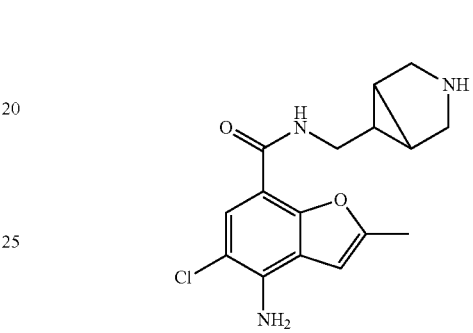

Step (i): Preparation of 4-Amino-5-chloro-2-methyl-N-{[3-(tert-butoxycarbonyl)-3-azabicyclo[3.1.0]hex-6-yl] methyl}benzofuran-7-carboxamide

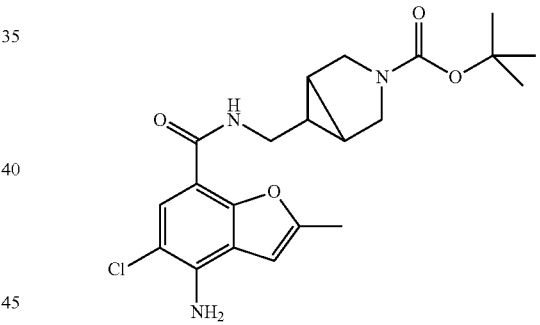

A solution of 4-Amino-5-chloro-2-methyl benzofuran-7-carboxylic acid (0.101 grams, 0.447 mmole, obtained from preparation 3) and CDI (0.080 grams, 0.492 mmole) in dry THF (3 mL) was stirred for 1 hour at RT. Then a solution of tert-butyl 6-aminomethyl-3-azabicyclo[3.1.0]hexane-3-carboxylate (0.095 grams, 0.447 mmole, obtained in the preparation 4) in DCM (2 mL) was added at RT. The reaction mass was stirred overnight (12 hours) at RT under nitrogen atmosphere, while monitoring the progress of the reaction by TLC. The reaction mass was concentrated and diluted with EtOAc (50 mL), washed with chilled water (15 mL) and brine solution (15 mL) and dried over Na$_2$SO$_4$. The organic phase was concentrated on rotavacuum to obtain the crude residue, which was further purified by flash chromatography using EtOAc:n-hexane (30:70) to afford the title compound Weight: 0.151 grams (Yield: 80%).
$^1$H-NMR (δ ppm): 0.97-1.00 (1H, m), 1.42 (9H, s), 1.55-1.58 (4H, m), 2.52 (3H, s), 3.33-3.38 (2H, m), 3.51-3.64 (2H, m), (2H, bs), 6.37 (1H, s), 7.31-7.34 (1H, t), 7.95 (1H, s);
Mass (m/z): 420.2 (M+H)$^+$, 422.3 (M+H)$^+$.

Step (ii): Preparation of 4-Amino-5-chloro-2-methyl-N-[(3-azabicyclo[3.1.0]hex-6-yl)methyl}benzofuran-7-carboxamide Ethanolic hydrogen chloride (23% w/w, 0.065 gram, 1.798 mmole) was added to a stirred solution of 4-amino-5-chloro-2-methyl-N-{[3-(tert-butoxycarbonyl)-3-azabicyclo [3.1.0]hex-6-yl]methyl}benzofuran-7-carboxamide (0.151 gram, 0.359 mmole, obtained in the above step) in ethanol (15 mL) at 10° C. The reaction mass was stirred overnight at RT, while monitoring the progress of the reaction by TLC. The reaction mass was concentrated and the slurry obtained was dissolved in water (15 mL). The pH was adjusted to ~9.5 using aqueous ammonia solution and the product was extracted with DCM (3×10 mL). The combined organic phase was washed with water (10 mL), brine solution (10 mL) and dried over $Na_2SO_4$. The organic phase was concentrated under vacuum to afford the title compound.

Weight: 0.089 gram (Yield: 77%).

$^1$H-NMR (δ ppm): 0.98-1.03 (1H, m), 1.27-1.29 (2H, m), 1.46-1.49 (1H, m), 2.55 (3H, s), 2.91-2.94 (2H, m), 3.03-3.06 (2H, m), 3.47-3.51 (2H, m), 4.55 (2H, bs), 6.41 (1H, s), 7.34-7.35 (1H, t), 8.00 (1H, s);

Mass (m/z): 320.2 (M+H)$^+$, 322.2 (M+H)$^+$.

Preparation 17: Preparation of 4-Amino-5-chloro-2-methyl-N-(4-fluoro-4-piperidinyl methyl)benzofuran-7-carboxamide

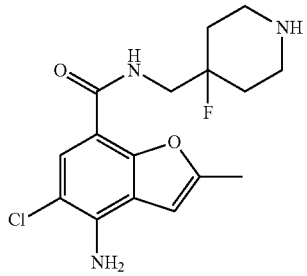 [SMILES: Cc1cc2c(N)c(Cl)cc(C(=O)NCC3(F)CCNCC3)c2o1]

Step (i): Preparation of 4-Amino-5-chloro-2-methyl-N-[4-fluoro-1-(tert-butoxycarbonyl)-4-piperidinyl methyl]benzofuran-7-carboxamide

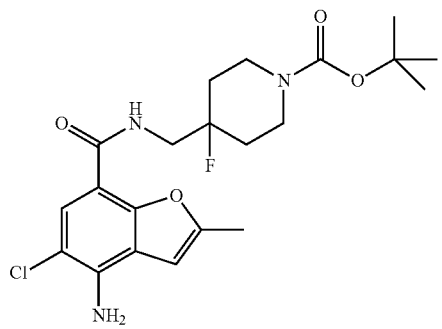 [SMILES: Cc1cc2c(N)c(Cl)cc(C(=O)NCC3(F)CCN(C(=O)OC(C)(C)C)CC3)c2o1]

A solution of 4-amino-5-chloro-2-methyl benzofuran-7-carboxylic acid (0.100 grams, 0.443 mmole, obtained from preparation 3) and CDI (0.079 grams, 0.487 mmole) in DCM (3 mL) was stirred for 2 hours at RT. Then added a solution of with tert-butyl 4-aminomethyl-4-fluoro piperidine-1-carboxylate (0.123 grams, 0.532 mmole, obtained in above step) in DCM (2 mL). The reaction mass was stirred overnight (12 hours) at RT under nitrogen atmosphere, while monitoring the progress of the reaction by TLC. The reaction mass was washed with chilled water (10 mL) and brine solution (10 mL) and dried over $Na_2SO_4$. The organic phase was concentrated on rotavacuum to obtain the crude residue, which was further purified by flash chromatography using EtOAc:n-hexane (30:70) to afford the title compound.

Weight: 0.188 grams (Yield: 97%).

$^1$H-NMR (δ ppm): 0.86-0.93 (2H, m), 1.45 (9H, s), 1.59-1.74 (2H, m), 1.87-1.90 (2H, m), 2.23-2.29 (2H, m), 2.51 (3H, s), 3.11-3.16 (2H, m), 4.54 (2H, bs), 6.37 (1H, s), 7.50-7.52 (1H, t), 7.96 (1H, s);

Mass (m/z): 440.2 (M+H)$^+$, 442.3 (M+H)$^+$.

Step (ii): Preparation of 4-Amino-5-chloro-2-methyl-N-(4-fluoro-4-piperidinyl methyl)benzofuran-7-carboxamide

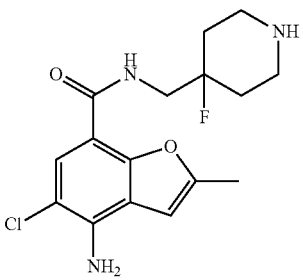 [SMILES: Cc1cc2c(N)c(Cl)cc(C(=O)NCC3(F)CCNCC3)c2o1]

Ethanolic hydrogen chloride (23% w/w, 0.074 grams, 2.047 mmole) was added to a solution of 4-amino-5-chloro-2-methyl-N-[4-fluoro-1-(t-butoxycarbonyl)-4-piperidinyl methyl] benzofuran-7-carboxamide (0.180 grams, 0.409 mmole, obtained in the above step) in ethanol (10 mL) at 10° C.: The reaction mass was stirred overnight at RT, while monitoring the progress of the reaction by TLC. Reaction mass was concentrated and the slurry obtained was dissolved in chilled water (15 mL). The pH was adjusted to ~9.5 using aqueous $NH_3$ solution and the product obtained was extracted with DCM (3×10 mL). The combined organic phase was washed with water (10 mL) and brine solution (10 mL) and dried over $Na_2SO_4$. The organic phase was concentrated under vacuum to afford the title compound.

Weight: 0.140 grams (Yield: 100%).

$^1$H-NMR (δ ppm): 1.09-1.15 (2H, m), 1.64-1.70 (2H, m), 1.98-2.21 (3H, m), 2.43 (3H, s), 2.67-2.79 (2H, m), 3.52-3.58 (2H, m), 6.33 (2H, bs), 6.85 (1H, s), 7.54 (1H, s), 7.73-7.74 (1H, t);

Mass (m/z): 340.2 (M+H)$^+$, 342.2 (M+H)$^+$.

Preparation 18: Preparation of 4-Amino-5-chloro-2-methyl-N-(4-hydroxy-4-piperidinyl methyl)benzofuran-7-carboxamide

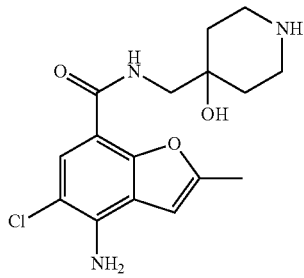 [SMILES: Cc1cc2c(N)c(Cl)cc(C(=O)NCC3(O)CCNCC3)c2o1]

Step (i): Preparation of 4-Amino-5-Chloro-2-methyl-N-[4-hydroxy-1-(tert-butoxy carbonyl)-4-piperidinyl methyl] benzofuran-7-carboxamide

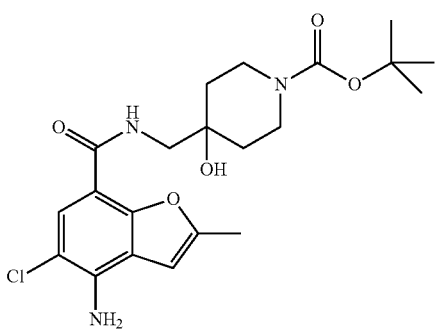 [SMILES: Cc1cc2c(N)c(Cl)cc(C(=O)NCC3(O)CCN(C(=O)OC(C)(C)C)CC3)c2o1]

A solution of 4-amino-5-chloro-2-methyl benzofuran-7-carboxylic acid (0.100 grams, 0.443 mmole, obtained from preparation 3) and CDI (0.093 grams, 0.576 mmole) in DCM (3 mL) was stirred for 2 hours at RT and added a solution of tert-butyl 4-aminomethyl-4-hydroxy piperidine-1-carboxylate (0.112 grams, 0.487 mmole) in DCM (2 mL). The reaction mass was stirred overnight (12 hours) at RT under nitrogen atmosphere and washed with chilled water (10 mL), brine solution (10 mL) and dried over anhydrous $Na_2SO_4$. The organic phase was concentrated on rotavacuum to obtain the crude residue, which was further purified by flash chromatography using EtOAc:n-hexane (80:20) to afford the title compound.

Weight; 0.184 grams (Yield: 95%).

$^1$H-NMR (δ ppm): 1.35 (9H, s), 1.39-1.51 (4H, m), 2.43 (3H, s), 3.08-3.10 (2H, m), 3.33-3.35 (2H, m), 3.60-3.63 (2H, m), 4.80 (1H, s), 6.31 (2H, bs), 6.85 (1H, s), 7.54 (1H, s), 7.67-7.70 (1H, t);

Mass (m/z): 438.4 (M+H)$^+$, 440.1 (M+H)$^+$.

Step (ii): Preparation of 4-Amino-5-chloro-2-methyl-N-(4-hydroxy-4-piperidinyl methyl)benzofuran-7-carboxamide Ethanolic hydrogen chloride (30% w/w, 0.075 gram, 2.05 mmole) was added to a solution of 4-amino-5-chloro-2-methyl-N-[4-hydroxy-1-(tert-butoxycarbonyl)-4-piperidinyl methyl] benzofuran-7-carboxamide (0.180 gram, 0.411 mmole, obtained in the above step) in DCM (5 mL) at 10° C. The reaction mass was stirred for 2 hours at RT, while monitoring the progress of the reaction by TLC. The reaction mass was concentrated and the slurry obtained was dissolved in chilled water (15 mL). The pH was adjusted to ~9.5 using aqueous $NH_3$ solution and the product obtained was extracted with DCM (3×10 mL). The combined organic phase was washed with water (10 mL) and brine solution (10 mL) and dried over $Na_2SO_4$. The organic phase was concentrated under vacuum to afford the title compound.

Weight: 0.134 grams (Yield: 97%).

$^1$H-NMR (δ ppm): 1.60-1.77 (4H, m), 2.44 (3H, s), 2.49 (2H, s), 2.96-3.10 (5H, m), 5.18 (1H, s), 6.35 (2H, bs), 6.88 (1H, s), 7.56 (1H, s), 7.77-7.80 (1H, t);

Mass (m/z): 338.1 (M+H)$^+$, 340.4 (M+H)$^+$.

Preparation 19: Preparation of 4-Amino-5-chloro-N-{[3-azabicyclo[3.1.0]hex-6-yl] methyl}-2,3-dihydrobenzofuran-7-carboxamide hydrochloride

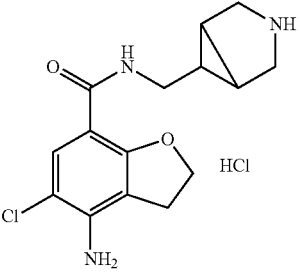 [SMILES: Nc1c(Cl)cc(C(=O)NCC2C3CNCC32)c2c1CCO2 ; Cl]

Step (i): Preparation of 5-Amino-6-Chloro-N-{[1-(tert-butoxycarbonyl)-3-azabicyclo[3.1.0]hex-6-yl] methyl}-2,3-dihydrobenzofuran-7-carboxamide

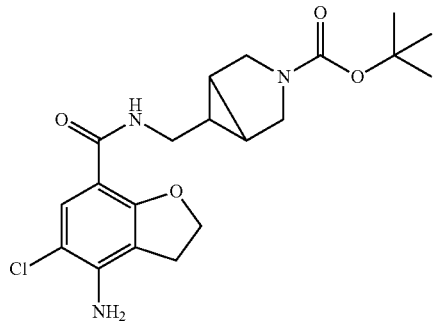 [SMILES: CC(C)(C)OC(=O)N1CC2C(CNC(=O)c3cc(Cl)c(N)c4c3OCC4)C2C1]

To a stirred solution of 4-amino-5-chloro-2,3-dihydrobenzofuran-7-carboxylic acid (1.22 grams, 5.71 mmols, prepared as per the procedure given in Chem. Pharm. Bull. 1998, 46(1), 42-52) in a mixture of DCM (11.4 mL) and DMF (2.0 mL) cooled at 0° C., diisopropylethylamine (1.48 mL, 8.56 mmols) was added. After stirring for 10 minutes, a solution of tert-butyl 6-aminomethyl-3-azabicyclo[3.1.0] hexane-3-carboxylate (1.27 grams, 5.99 mmols, obtained in preparation 4) in DCM (11.4 mL) was added which was followed by TBTU (2.01 grams, 6.28 mmols) addition. After stirring the reaction mixture at RT for 16 hours, the volatiles were removed under reduced pressure and the crude product was purified by silica gel column chromatography to obtain the title compound.

Weight: 2.45 grams $^1$H-NMR (δ ppm): 0.95-0.96 (m, 1H), 1.45-1.50 (2H, m), 3.07 (2H, t, J=8.6 Hz), 3.20-3.30 (1H, m), 3.30-3.40 (2H, m), 3.40-3.50 (1H, m), 3.53 (1H, d, J=10.7 Hz), 3.62 (1H, d, J=10.7 Hz), 4.27 (2H, bs), 4.79 (2H, t, J=8.6 Hz), 7.39 (1H, bs), 7.85 (1H, s);

Mass (m/z): 408.1, 410.2 (M+H)$^+$.

Step (ii): Preparation of 4-Amino-5-chloro-N-{[3-azabicyclo[3.1.0]hex-6-yl]methyl}-2,3-dihydrobenzofuran-7-carboxamide hydrochloride To a stirred solution of 5-amino-6-chloro-N-{[1-(tert-butoxycarbonyl)-3-azabicyclo[3.1.0]hex-6-yl]methyl}-2,3-dihydrobenzofuran-7-carboxamide (452.0 mg, 1.11 mmols, obtained in the above step) in isopropanol (1.1 mL), cooled at 0° C., a solution of dry HCl in isopropanol (3M, 6 mL) was added. The reaction mass was gradually warmed to RT and after stirring for 16 hours, the volatiles were removed under reduced pressure and the crude mass was triturated with ether to obtain the product as white solid.
Weight: 337.3 mg (Yield: 88%).
$^1$H-NMR (δ ppm): 1.16-1.26 (1H, m), 1.65-1.72 (2H, m), 3.02 (2H, t, J=8.7 Hz), 3.10-3.38 (6H, m), 4.71 (2H, t, J=8.7 Hz), 4.83 (2H, bs), 4.79 (2H, t, J=8.6 Hz), 7.50 (1H, s), 7.58 (1H, bs), 8.85 (1H, bs), 9.49 (1H, bs).
Mass (m/z): 308.2, 310.2 (M+H)$^+$.

Preparation 20: Preparation of 2,2-dimethyl-3-methoxy propyl toluene-4-sulfonate

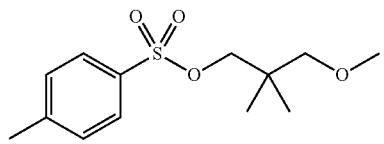

Step (i): Preparation of 2,2-dimethyl-3-methoxy propan-1-ol

A solution of 2,2-dimethyl propane-1,3-diol (10 grams, 0.096 mole) in THF (40 mL) was added to a stirred solution of NaH (60%, 3.84 grams, 0.160 mole) in THF (60 mL) drop wise at 0° C. Then reaction mass was slowly heated to 80° C. and stirred for 1 hour. The reaction mixture was cooled to RT and added methyliodide (15 grams, 0.105 mole). The reaction mass was stirred overnight (20 hours) at RT under nitrogen atmosphere and poured onto chilled water (100 mL) and the product obtained was extracted with diethyl ether (DEE) (3×100 mL). The combined organic phase was washed with water (100 mL) and brine solution (100 mL) and dried over sodium sulfate. The organic phase was concentrated under vacuum to obtain a crude residue, which was further purified by flash chromatography using MeOH: CHCl$_3$ (1.5:98.5) to afford the title compound.
Weight: 6.5 grams (Yield: 57.52%).
$^1$H-NMR (δ ppm): 0.90 (6H, s), 2.66-2.68 (1H, t), 3.23 (2H, s), 3.33 (3H, s), 3.42-3.43 (2H, d);
Mass (m/z): 119.4 (M+H)$^+$.

Step (ii): Preparation of 2,2-dimethyl-3-methoxy propyl toluene-4-sulfonate p-Toluene sulfonyl chloride (3.74 grams, 0.019 mole) was added to a stirred solution of 2,2-dimethyl-3-methoxy pro-pan-1-ol (2.0 grams, 0.160 mole, obtained in the above step) in pyridine (60 mL) portion wise at 0° C. The reaction mass was stirred overnight (20 hours) at RT under nitrogen atmosphere. After completion of the reaction (TLC), the reaction mass was poured onto chilled 1N solution of aqueous HCl (60 mL) and the product was extracted with DEE (3×50 mL). The combined organic phase was washed with water (40 mL), brine solution (40 mL) and dried over Na$_2$SO$_4$. The organic phase was concentrated under vacuum to afford the title compound.
Weight: 4.25 grams (Yield: 92.19%).
$^1$H-NMR (δ ppm): 0.87 (6H, s), 2.44 (3H, s), 3.06 (2H, s), 3.22 (3H, s), 3.78 (2H, s), 7.33-7.35 (2H, d, J=8.00 Hz), 7.77-7.79 (2H, d, J=8.00 Hz);
Mass (m/z): 273.2 (M+H)$^+$.

Preparation 21: Preparation of 2-methoxy-2-methyl propyl toluene-4-sulfonate

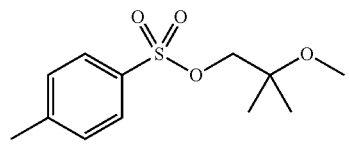

Step (i): Preparation of 2-methoxy-2-methyl propan-1-ol

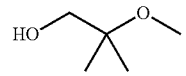

A solution of isobutyleneoxide (1.0 grams, 13.888 mmole) and indium chloride (0.61 grams, 2.757 mmole) in MeOH (20 mL) was stirred at 50° C. for 5 hours while monitoring the progress of the reaction by TLC. After completion of the reaction (TLC), the reaction mass was concentrated under vacuum and the residue was dissolved in DCM (50 mL). The organic phase was washed with saturated sodium bicarbonate solution (10 mL) and dried over Na$_2$SO$_4$. The organic phase was concentrated under vacuum to afford the title compound.
Weight: 0.18 grams (Yield: 12.5%).
$^1$H-NMR (δ ppm): 1.16 (6H, s), 1.94-1.97 (1H, t), 3.23 (3H, s), 3.42-3.44 (2H, d);
Mass (m/z): 105.1 (M+H)$^+$.

Step (ii): Preparation of 2-methoxy-2-methyl propyl toluene-4-sulfonate p-Toluene sulfonyl chloride (0.36 grams, 1.889 mmole) was added to a stirred solution of 2-methoxy-2-methyl propan-1-ol (0.18 grams, 1.73 mmole, obtained in the above step) in pyridine (2 mL) portion wise at 0° C. The reaction mass was stirred for 48 hours at RT under nitrogen atmosphere. After completion of the reaction (TLC), the reaction mass was poured onto chilled 1 N aqueous HCl (10 mL) and the product was extracted with ethyl acetate (3×5 mL). The combined organic phase was washed with water (5 mL), brine solution (5 mL) and dried over Na$_2$SO$_4$. The organic phase was concentrated under vacuum to afford the title compound.
Weight: 0.26 grams (Yield: 12.5%).
$^1$H-NMR (δ ppm): 1.13 (6H, s), 2.45 (3H, s), 3.14 (3H, s), 3.85 (2H, s), 7.33-7.35 (2H, d, J=8.00 Hz), 7.79-7.81 (2H, d, J=8.00 Hz);
Mass (m/z): 259.2 (M+H)$^+$.

Example 1: Preparation of 5-Amino-6-chloro-N-{[3-(tetrahydro-2H-pyran-4-ylmethyl)-3-azabicyclo[3.1.0]hex-6-yl]methyl}chroman-8-carboxamide hydrochloride

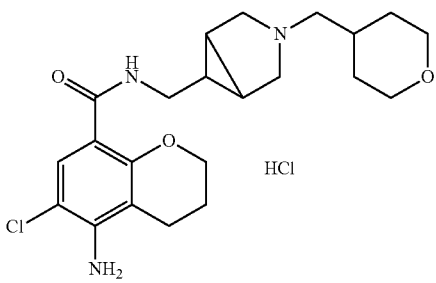 [SMILES: Nc1c(Cl)cc(C(=O)NCC2C3CN(CC4CCOCC4)CC23)c2c1CCCO2 ; Cl]

Step (i): Preparation of 5-Amino-6-chloro-N-{[3-(tetrahydro-2H-pyran-4-ylmethyl)-3-azabicyclo[3.1.0]hex-6-yl]methyl}chroman-8-carboxamide

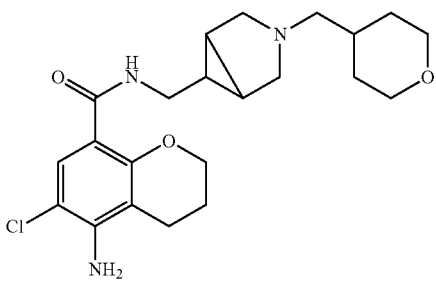 [SMILES: Nc1c(Cl)cc(C(=O)NCC2C3CN(CC4CCOCC4)CC23)c2c1CCCO2]

A solution of 5-amino-6-chloro-N-{[3-azabicyclo[3.1.0]hex-6-yl]methyl} chroman-8-carboxamide (7.4 grams, 0.023 mole, obtained in the preparation 8) and tetrahydro pyran-4-carboxaldehyde (3.14 grams, 0.027 mole) in dichloroethane (DCE) (200 mL) was cooled to 10° C. and treated with sodium triacetoxyborohydride (9.75 gram, 0.046 mole). The reaction mass was stirred overnight at RT. After completion of the reaction (TLC), the reaction mass was poured onto water (100 mL). The pH of the resulting mass was adjusted to ~9.5 with aqueous $NH_3$ solution and separated both layers. The aqueous layer was extracted with DCM (3×50 mL). The combined organic phase was washed with water (50 mL), brine solution (50 mL) and dried over $Na_2SO_4$. The organic phase was concentrated under vacuum to obtain a crude residue, which was further purified by flash chromatography using TEA:MeOH:$CHCl_3$ (0.5:2:97.5) to afford the title compound.

Weight: 7.4 gram (Yield: 77%).

$^1$H-NMR (δ ppm): 1.04-1.20 (2H, m), 1.21-1.29 (3H, m), 1.51-1.58 (3H, m), 1.94-1.98 (2H, m), 2.16-2.22 (4H, m), 2.44-2.49 (2H, m), 2.87-2.89 (2H, d), 3.05-3.08 (2H, t), 3.19-3.25 (2H, t), 3.75-3.79 (2H, m), 4.18-4.21 (2H, m), 5.59 (2H, bs), 7.58 (1H, s), 7.97-8.00 (1H, t);

Mass (m/z): 420.3 (M+H)$^+$, 422.4 (M+H)$^+$.

Step (ii): Preparation of 5-Amino-6-chloro-N-{[3-(tetrahydro-2H-pyran-4-ylmethyl)-3-azabicyclo[3.1.0]hex-6-yl]methyl}chroman-8-carboxamide hydrochloride Methanolic hydrogen chloride (20% w/w, 0.22 gram, 6.02 mmole) was added to a solution of 5-amino-6-chloro-N-{[3-(tetrahydro-2H-pyran-4-ylmethyl)-3-azabicyclo[3.1.0]hex-6-yl]methyl} chroman-8-carboxamide (1.0 gram, 2.38 mmole, obtained in the above step) in diethyl ether (DEE) (40 mL) and MeOH (5 mL) at RT. The reaction mass was heated at 40° C. under stirring and added MeOH (5 mL) to obtain a clear solution. The clear mass obtained was stirred further for 2 hours at 40° C. and allowed to cool to RT. The reaction mass was stirred overnight at RT and resulted solid mass was filtered under vacuum. The solid mass, thus obtained, was washed with chilled DEE (20 mL) and dried under vacuum to afford the title compound.

Weight: 0.86 gram (Yield: 79.6%).

$^1$H-NMR (δ ppm): 1.14-1.17 (2H, m), 1.55-1.65 (2H, m), 1.73-1.78 (2H, m), 1.82-1.94 (2H, m), 2.31-2.48 (2H, m), 2.68-2.82 (1H, m), 2.87-2.92 (1H, m), 2.97-3.11 (2H, m), 3.13-3.15 (2H, m), 3.21-3.26 (4H, m), 3.62-3.65 (2H, m), 3.78-3.90 (2H, m), 4.18-4.19 (2H, m), 5.62 (2H, bs), 7.58 (1H, s), 8.09-8.12 (1H, t), 9.50 (1H, bs);

Mass (m/z): 420.3 (M+H)$^+$, 422.4 (M+H)$^+$.

Example 2: Preparation of 5-Amino-6-chloro-N-{[3-(tetrahydro-2H-pyran-4-ylmethyl)-3-azabicyclo[3.1.0]hex-6-yl]methyl}chroman-8-carboxamide hemifumarate

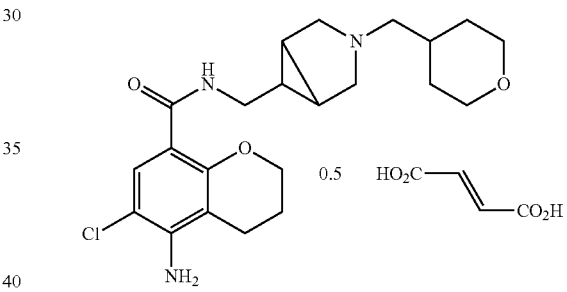

A solution of 5-amino-6-chloro-N-{[3-(tetrahydro-2H-pyran-4-ylmethyl)-3-azabicyclo[3.1.0]hex-6-yl]methyl}chroman-8-carboxamide (2 gram, 4.76 mmole, obtained in the step (i) of Example 1) in DEE (80 mL) and ethanol (20 mL) was heated at 40° C. under stirring for 1 hour. Fumaric acid (0.387 gram, 3.33 mmole) solution in ethanol (4 mL) was added slowly at 40° C. During addition clear solution was obtained. After completion of addition (~10 minutes), the mass was stirred further for 10 minutes at 40° C., during stirring solids formation was observed. The mass was allowed to cool to RT and stirred overnight at same temperature, the resulted solids were filtered under vacuum. The solid mass, thus obtained, was washed with chilled DEE (20 mL) and dried under vacuum to afford the title compound.

Weight: 1.85 gram (Yield: 81.4%).

$^1$H-NMR (δ ppm): 0.98-1.07 (2H, m), 1.28-1.29 (1H, m), 1.52-1.58 (3H, m), 1.94-1.96 (2H, m), 2.21-2.24 (4H, m), 2.44-2.45 (2H, m), 2.91-2.93 (2H, m), 3.05-3.09 (2H, m), 3.19-3.25 (4H, m), 3.75-3.79 (2H, m), 4.18-4.21 (2H, m), 5.59 (2H, s), 6.58 (1H, s), 7.58 (1H, s), 7.97-8.00 (1H, t);

Mass (m/z): 420.4 (M+H)$^+$, 422.3 (M+H)$^+$.

Example 3: Preparation of 5-Amino-6-chloro-N-{[3-(tetrahydro-2H-pyran-4-ylmethyl)-3-azabicyclo[3.1.0]hex-6-yl]methyl}chroman-8-carboxamide L(+)-tartarate

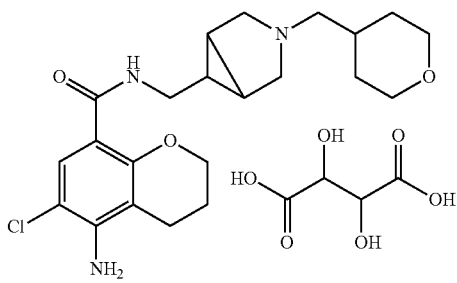

A solution of L(+)-tartaric acid (0.212 gram, 1.42 mmole) in 5 mL MeOH was added to a stirred solution of 5-Amino-6-chloro-N-{[3-(tetrahydro-2H-pyran-4-ylmethyl)-3-azabicyclo[3.1.0]hex-6-yl]methyl}chroman-8-carboxamide (0.6 gram, 1.43 mmole, obtained in step (i) of example 1) in MeOH (15 mL). The clear mass obtained was stirred further for 2 hours at RT. The solvent was evaporated to afford solid mass. The solid mass was triturated with DEE (20 mL) and dried under reduced pressure to obtain the title compound.

Yield: 0.79 gram (97.9%).

$^1$H-NMR (δ ppm): 1.25-1.36 (4H, m), 1.49-1.51 (1H, m), 1.66-1.76 (2H, m), 1.86-1.88 (2H, m), 2.04-2.06 (1H, m), 2.07-2.09 (2H, m), 2.51-2.55 (2H, t), 2.98-3.00 (2H, d), 3.37-3.46 (4H, m), 3.48-3.55 (2H, m), 3.89-3.93 (2H, m), 4.25-4.28 (2H, t), 4.41 (2H, s), 7.71 (1H, s), 8.40-8.43 (1H, t);

Mass (m/z): 420.3 (M+H)$^+$, 422.4 (M+H)$^+$.

Examples 4 to 29

The compounds of Examples 4 to 29 were prepared by following the experimental procedures as described in the Examples 1 to 3 given above, with some noncritical variations.

| Example Number | Chemical name and Structure | Characterization data |
|---|---|---|
| 4. | 5-Amino-6-chloro-N-{[3-(tetrahydro-2H-pyran-4-ylmethyl)-3-azabicyclo[3.1.0]hex-6-yl]methyl}chroman-8-carboxamide | $^1$H-NMR (δ ppm): 1.22-1.30 (4H, m), 1.51-1.54 (4H, m), 1.94-1.98 (2H, m), 2.16-2.18 (4H, m), 2.44-2.48 (2H, m), 2.88-2.90 (2H, m), 3.05-3.08 (2H, m), 3.19-3.25 (2H, m), 3.75-3.82 (2H, m), 4.18-4.21 (2H, m), 5.59 (2H, bs), 7.58 (1H, s), 7.97-8.00 (1H, t); Mass (m/z): 420.3 (M + H)$^+$, 422.4 (M + H)$^+$. |
| 5. | 5-Amino-6-chloro-N-{[3-(tetrahydro-2H-pyran-4-yl)-3-azabicyclo[3.1.0]hex-6-yl]methyl}chroman-8-carboxamide | $^1$H-NMR (δ ppm): 1.29-1.34 (2H, m), 1.37-1.41 (1H, m), 1.66-1.71 (3H, m), 1.94-1.96 (3H, m), 2.44-2.49 (2H, m), 2.51-2.54 (2H, m), 3.05-3.15 (3H, m), 3.20-3.50 (4H, m), 3.58-3.81 (2H, m), 4.19-4.21 (2H, t), 5.59 (2H, s), 7.59 (1H, s), 8.01-8.04 (1H, t); Mass (m/z): 406.3 (M + H)$^+$, 408.1 (M + H)$^+$. |

-continued

| Example Number | Chemical name and Structure | Characterization data |
|---|---|---|
| 6. | 5-Amino-6-chloro-N-{[3-(tetrahydro-2H-pyran-4-yl)-3-azabicyclo[3.1.0]hex-6-yl]methyl}chroman-8-carboxamide L(+)-tartarate 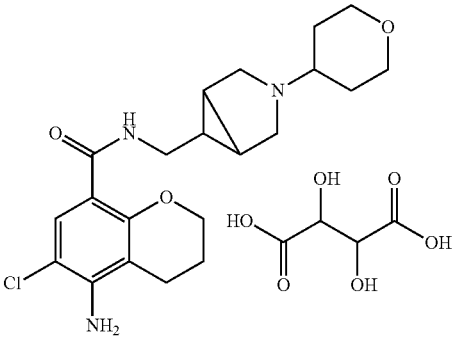 | $^1$H-NMR (δ ppm): 1.21-1.29 (3H, m), 1.36-1.40 (2H, m), 1.67-1.71 (2H, m), 1.81-1.90 (2H, m), 1.96-1.99 (2H, m), 2.07-2.10 (2H, m), 3.31-3.40 (3H, m), 3.42-3.51 (2H, m), 3.54-3.67 (2H, m), 3.98-4.02 (2H, m), 4.27-4.29 (2H, t), 4.45 (2H, s), 7.72 (1H, s); Mass (m/z): 406.3 (M + H)$^+$, 408.1 (M + H)$^+$. |
| 7. | 5-Amino-N-{[3-(tetrahydro-2H-pyran-4-ylmethyl)-3-azabicyclo[3.1.0]hex-6-yl]methyl}chroman-8-carboxamide L(+)-tartarate 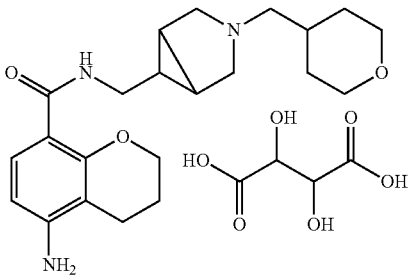 | $^1$H-NMR (δ ppm): 1.26-1.35 (4H, m), 1.38-1.48 (1H, m), 1.63-1.66 (2H, m), 1.85-1.99 (4H, m), 2.02-2.08 (2H, m), 2.46-2.49 (2H, t), 3.03-3.11 (3H, m), 3.36-3.42 (2H, t), 3.64-3.73 (2H, m), 3.89-3.93 (2H, m), 4.23-4.26 (2H, t), 4.50 (2H, s), 6.30-6.32 (1H, d; J = 8.64 Hz), 7.58-7.60 (1H, d, J = 8.62 Hz); Mass (m/z): 386.4 (M + H)$^+$. |
| 8. | (R,S) 5-Amino-6-chloro-N-{[3-(tetrahydro-3-furanylmethyl)-3-azabicyclo[3.1.0]hex-6-yl]methyl}chroman-8-carboxamide 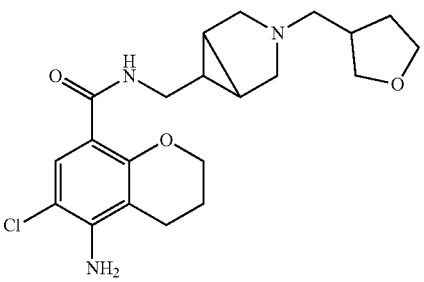 [SMILES: Nc1c(Cl)cc(C(=O)NCC2C3CN(CC4CCOC4)CC23)c2c1CCCO2] | $^1$H-NMR (δ ppm): 1.42-1.45 (2H, m), 1.79-1.89 (2H, m), 1.94-1.97 (2H, m), 2.18-2.22 (2H, m), 2.28-2.38 (2H, m), 2.44-2.49 (2H, m), 2.71-2.81 (1H, m), 2.89-2.94 (2H, m), 3.07-3.09 (2H, t), 3.41-3.49 (1H, m), 3.52-3.56 (2H, m), 3.64-3.72 (2H, m), 4.19-4.21 (2H, t), 5.59 (2H, bs), 7.59 (1H, s), 7.98-8.00 (1H, t); Mass (m/z): 406.4 (M + H)$^+$, 408.3 (M + H)$^+$. |
| 9. | (R,S) 5-Amino-6-chloro-N-{[3-(tetrahydro-3 furanylmethyl)-3-azabicyclo[3.1.0]hex-6-yl]methyl}chroman-8-carboxamide L(+)-tartarate 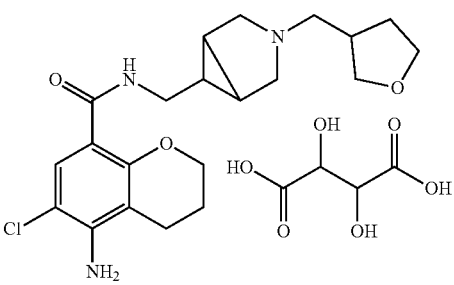 | $^1$H-NMR (δ ppm): 1.62-1.67 (1H, m), 1.73-1.78 (2H, m), 2.07-2.13 (2H, m), 2.14-2.17 (1H, m), 2.52-2.57 (3H, m), 3.01-3.09 (4H, m), 3.40-3.55 (4H, m), 3.58-3.62 (1H, m), 3.64-3.75 (2H, m), 3.82-3.90 (2H, m), 4.27-4.29 (2H, t), 4.42 (2H, s), 7.73 (1H, s); Mass (m/z): 406.4 (M + H)$^+$, 408.6 (M + H)$^+$. |

-continued

| Example Number | Chemical name and Structure | Characterization data |
|---|---|---|
| 10. | 5-Amino-6-chloro-N-{[4-fluoro-1-(tetrahydro-3-furanylmethyl)-4-piperidinyl]methyl}chroman-8-carboxamide | $^1$H-NMR (δ ppm): 1.47-1.50 (1H, m), 1.58-1.69 (4H, m), 1.87-4.97 (4H, m), 2.12-2.24 (4H, m), 2.37-2.46 (3H, m), 2.48-2.66 (2H, m), 3.46-3.58 (3H, m), 3.65-3.70 (2H, m), 4.18-4.21 (2H, t), 5.66 (2H, s), 7.60 (1H, s), 8.01 (1H, t); Mass (m/z): 426.2 (M + H)$^+$, 428.3 (M + H)$^+$. |
| 11. | 5-Amino-6-bromo-N-{[3-(tetrahydro-2H-pyran-4-ylmethyl)-3-azabicyclo[3.1.0]hex-6-yl]methyl}chroman-8-carboxamide | $^1$H-NMR (δ ppm): 1.21-1.27 (2H, m), 1.49-1.62 (4H, m), 1.68-1.78 (1H, m), 1.91-1.93 (2H, m), 2.09-2.21 (3H, m), 2.42-2.50 (2H, m), 2.79-2.87 (2H, m), 2.91-3.04 (1H, m), 3.06-3.12 (2H, m), 3.23-3.27 (3H, m), 3.69-3.76 (2H, m), 4.16-4.18 (2H, t), 5.49 (2H, bs), 7.71 (1H, s), 7.96-7.99 (1H, t); Mass (m/z): 464.1 (M + H)$^+$, 466.1 (M + H)$^+$. |
| 12. | 5-Amino-6-bromo-N-{[3-(tetrahydro-2H-pyran-4-ylmethyl)-3-azabicyclo[3.1.0]hex-6-yl]methyl}chroman-8-carboxamide L(+)-tartarate | $^1$H-NMR (δ ppm): 1.26-1.35 (2H, m), 1.42-1.48 (1H, m), 1.63-1.66 (2H, m), 1.82-1.98 (3H, m), 2.05-2.07 (2H, m), 2.52-2.55 (2H, t), 2.99-3.01 (2H, d), 3.12-3.32 (4H, m), 3.36-3.45 (4H, m), 3.89-3.93 (2H, m), 4.24-4.26 (2H, t), 4.44 (2H, s), 7.87 (1H, s); Mass (m/z): 464.1 (M + H)$^+$, 466.0 (M + H)$^+$. |
| 13. | 4-Amino-5-chloro-N-{[3-(tetrahydro-2H-pyran-4-ylmethyl)-3-azabicyclo[3.1.0]hex-6-yl]methyl}benzofuran-7-carboxamide hydrochloride | $^1$H-NMR (δ ppm): 1.11-1.22 (3H, m), 1.59-1.63 (3H, m), 1.78 (2H, s), 1.87 (1H, s), 2.97-3.00 (2H, t), 3.15-3.29 (5H, m), 3.63-3.67 (2H, m), 3.79-3.82 (2H, m), 6.47 (2H, bs), 7.26-7.27 (1H, m), 7.60 (1H, s), 7.91-7.92 (1H, m), 7.98-8.00 (1H, t), 9.1 (1H, bs); Mass (m/z): 404.1 (M + H)$^+$, 406.1 (M + H)$^+$. |

-continued

| Example Number | Chemical name and Structure | Characterization data |
|---|---|---|
| 14. | 4-Amino-5-chloro-N-{[3-(tetrahydro-2H-pyran-4-yl)-3-azabicyclo[3.1.0]hex-6-yl]methyl}benzofuran-7-carboxamide | $^1$H-NMR (400 MHz, CDCl$_3$): δ 1.40-1.80 (m, 7H), 2.40-2.60 (2H, m), 3.15-3.30 (1H, m), 3.31-3.43 (6H, m), 3.97 (2H, d, J = 11.4 Hz), 4.64 (2H, bs), 6.78 (1H, s), 7.34 (1H, bs), 7.65 (1H, s), 8.04 (1H, s); Mass (m/z): 390.1 (M + H)$^+$, 391.9 (M + H)$^+$. |
| 15. | 4-Amino-5-chloro-N-{[3-(tetrahydro-2H-pyran-4-yl)-3-azabicyclo[3.1.0]hex-6-yl]methyl}benzofuran-7-carboxamide oxalate | $^1$H-NMR (δ ppm): δ 1.20-1.30 (2H, m), 1.50-1.60 (1H, m), 1.60-1.75 (2H, m), 1.75-1.88 (4H, m), 3.10-3.30 (5H, m), 3.50-3.65 (2H, m), 3.82-3.92 (2H, m), 6.46 (2H, bs), 7.26 (1H, s), 7.59 (1H, s), 7.91 (1H, s), 7.95 (1H, bs); Mass (m/z): 390.2 (M + H)$^+$, 392.0 (M + H)$^+$. |
| 16. | 4-Amino-5-chloro-N-{[3-(1-methoxycarbonylpiperidine-4-yl)-3-azabicyclo[3.1.0]hex-6-yl]methyl}benzofuran-7-carboxamide | $^1$H-NMR (400 MHz, CDCl$_3$): δ 1.35-1.50 (3H, m), 1.55-1.65 (2H, m), 1.70-1.83 (2H, m), 2.20-2.30 (1H, m), 2.32-2.45 (2H, m), 2.33-2.98 (2H, m), 3.02-3.20 (2H, m), 3.36-3.45 (2H, m), 3.67 (3H, s), 3.85-4.05 (2H, m), 4.64 (2H, bs), 6.78 (1H, d, J = 1.9 Hz), 7.31 (1H, bs), 7.65 (1H, d, J = 1.9 Hz), 8.04 (1H, s); Mass (m/z): 447.1 (M + H)$^+$, 449.1 (M + H)$^+$. |

-continued

| Example Number | Chemical name and Structure | Characterization data |
|---|---|---|
| 17. | 4-Amino-5-chloro-N-{[3-(1-methoxycarbonylpiperidine-4-yl)-3-azabicyclo[3.1.0]hex-6-yl]methyl}benzofuran-7-carboxamide oxalate 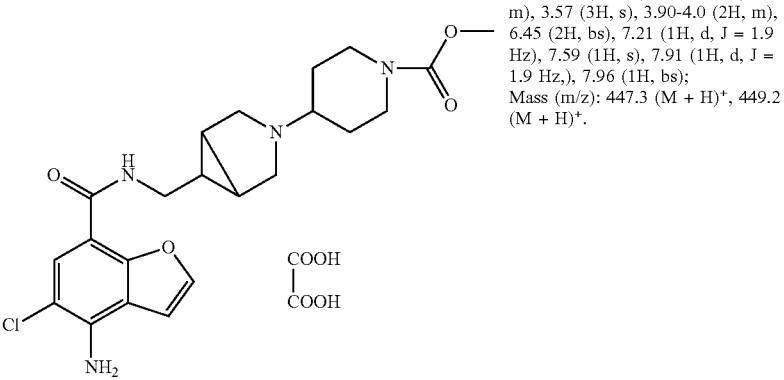 | $^1$H-NMR (δ ppm): δ 1.32-1.45 (3H, m), 1.70-1.80 (2H, m), 1.86-1.96 (2H, m), 2.65-2.85 (2H, m), 3.00-3.25 (5H, m), 3.40-3.55 (2H, m), 3.57 (3H, s), 3.90-4.0 (2H, m), 6.45 (2H, bs), 7.21 (1H, d, J = 1.9 Hz), 7.59 (1H, s), 7.91 (1H, d, J = 1.9 Hz,), 7.96 (1H, bs); Mass (m/z): 447.3 (M + H)$^+$, 449.2 (M + H)$^+$. |
| 18. | 4-Amino-5-chloro-2-methyl-N-{[3-(tetrahydro-2H-pyran-4-ylmethyl)-3-azabicyclo[3.1.0]hex-6-yl]methyl}benzofuran-7-carboxamide hydrochloride 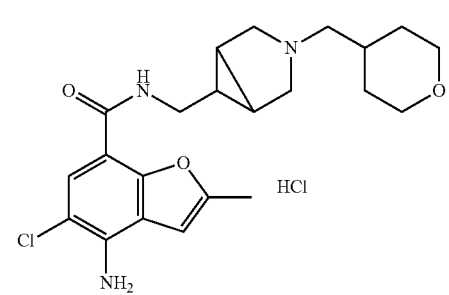 [SMILES: Cc1cc2c(N)c(Cl)cc(C(=O)NCC3C4CN(CC5CCOCC5)CC34)c2o1 ; Cl] | $^1$H-NMR (δ ppm): 1.06-1.19 (2H, m), 1.59-1.65 (4H, m), 1.76-1.79 (2H, m), 1.85-1.86 (1H, m), 2.42 (3H, s), 2.94-2.97 (2H, m), 3.16-3.26 (5H, m), 3.60-3.64 (2H, m), 3.76-3.79 (2H, m), 6.28 (2H, bs), 6.81 (1H, s), 7.48 (1H, s), 7.88-7.91 (1H, t), 9.44 (1H, bs); Mass (m/z): 418.3 (M + H)$^+$, 420.3(M + H)$^+$. |
| 19. | 4-Amino-5-chloro-N-[(3-isopropyl-3-azabicyclo[3.1.0]hex-6-yl)methyl]-2,3-dihydrobenzofuran-7-carboxamide 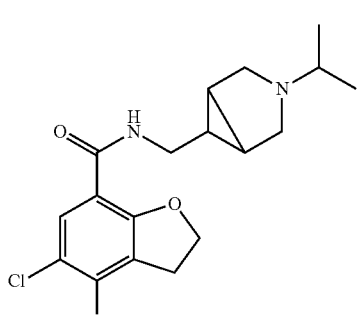 | $^1$H-NMR (400 MHz, CDCl$_3$): δ 1.02 (6H, d, J = 6.2 Hz), 1.32-1.43 (3H, m), 2.37 (2H, d, J = 9.3 Hz), 3.00-3.10 (4H, m), 3.27 (2H, t, J = 6.3 Hz), 4.22 (2H, bs), 4.78 (2H, t, J = 8.7 Hz), 7.36 (1H, bs), 7.86 (1H, s). Mass (m/z): 350.3 (M + H)$^+$, 352.4 (M + H)$^+$. |

-continued

| Example Number | Chemical name and Structure | Characterization data |
|---|---|---|
| 20. | 4-Amino-5-chloro-N-[(3-isopropyl-3-azabicyclo[3.1.0]hex-6-yl)methyl]-2,3-dihydrobenzofuran-7-carboxamide oxalate | $^1$H-NMR (δ ppm): δ 1.14 (6H, s), 1.30-1.40 (1H, m), 1.70-1.78 (2H, m), 3.0 (2H, t, J = 8.6 Hz), 3.11 (2H, t, J = 6.1 Hz), 3.15-3.35 (3H, m), 3.30-3.55 (2H, m), 4.68 (2H, t, J = 8.6 Hz,), 5.85 (2H, bs), 7.43 (1H, s), 7.57 (1H, bs); Mass (m/z): 350.3 (M + H)$^+$, 352.4 (M + H)$^+$. |
| 21. | 4-Amino-5-chloro-N-{[3-(cyclobutylmethyl)-3-azabicyclo[3.1.0]hex-6-yl]methyl}-2,3-dihydrobenzofuran-7-carboxamide | $^1$H-NMR (400 MHz, CDCl$_3$): δ 1.35-1.38 (2H, m), 1.38-1.45 (1H, m), 1.62-1.72 (4H, m), 1.85-1.95 (1H, m), 2.00-2.10 (2H, m), 2.33 (2H, d, J = 8.4 Hz), 2.43-2.48 (2H, m), 3.02 (2H, d, 8.8 Hz), 3.10 (2H, t, J = 8.6 Hz), 3.30 (2H, t, J = 6.0 Hz), 4.27 (2H, bs), 4.82 (2H, t, J = 8.6 Hz), 7.39 (1H, bs), 7.90 (1H, s); Mass (m/z): 376.3 (M + H)$^+$, 378.2 (M + H)$^+$. |
| 22. | 4-Amino-5-chloro-N-{[3-(cyclobutylmethyl)-3-azabicyclo[3.1.0]hex-6-yl]methyl}-2,3-dihydrobenzofuran-7-carboxamide oxalate | $^1$H-NMR (δ ppm): δ 1.38-1.48 (1H, m), 1.65-1.80 (4H, m), 1.80-1.90 (1H, m), 1.97-2.08 (2H, m), 2.47-2.60 (1H, m), 3.00-3.25 (8H, m), 3.35-3.50 (2H, m), 4.72 (2H, t, J = 8.7 Hz), 5.90 (2H, s), 7.47 (1H, s), 7.60 (1H, bs); Mass (m/z): 376.3 (M + H)$^+$, 378.2 (M + H)$^+$. |

| Example Number | Chemical name and Structure | Characterization data |
|---|---|---|
| 23. | 4-Amino-5-chloro-N-{[3-(1-methoxycarbonylpiperidine-4-yl)-3-azabicyclo[3.1.0]hex-6-yl]methyl}-2,3-dihydrobenzofuran-7-carboxamide | ¹H-NMR (400 MHz, CDCl₃): δ 1.32-1.40 (3H, m), 1.57-1.60 (2H, m), 1.68-1.78 (2H, m), 2.17-2.25 (2H, m), 2.34 (2H, d, J = 8.1 Hz), 2.88-2.88 (2H, m), 3.02-3.12 (4H, m), 3.23-3.33 (2H, m), 3.66 (3H, s), 3.82-4.0 (2H, m), 4.24 (2H, bs), 4.78 (2H, t, J = 8.6 Hz), 7.36 (1H, bs), 7.86 (1H, s); Mass (m/z): 449.2 (M + H)⁺, 451.0 (M + H)⁺. |
| 24. | 4-Amino-5-chloro-N-{[3-(1-methoxycarbonylpiperidine-4-yl)-3-azabicyclo[3.1.0]hex-6-yl]methyl}-2,3-dihydrobenzofuran-7-carboxamide L(+)-tartarate | ¹H-NMR (δ ppm): δ 1.18-1.32 (3H, m), 1.42-1.50 (2H, m), 1.72-1.82 (2H, m), 2.40-2.60 (3H, m), 2.78-2.90 (2H, m), 3.00-3.15 (4H, m), 3.30-3.50 (2H, m), 3.56 (3H, s), 3.76-3.88 (2H, m), 4.18 (2H, s), 4.72 (2H, t, J = 8.7 Hz), 5.87 (2H, bs), 7.46 (1H, s), 7.53 (1H, bs); Mass (m/z): 449.2 (M + H)⁺, 451.1 (M + H)⁺. |
| 25. | 4-Amino-5-chloro-N-{[3-(tetrahydropyran-4-ylmethyl)-3-azabicyclo[3.1.0]hex-6-yl]methyl}-2,3-dihydrobenzofuran-7-carboxamide | ¹H-NMR (400 MHz, CDCl₃): δ 1.18-1.32 (2H, m), 1.35-1.46 (3H, m), 1.60-1.70 (3H, m), 2.25-2.35 (4H, m), 3.02 (2H, d, J = 8.5 Hz), 3.10 (2H, t, J = 8.6 Hz), 3.30 (2H, t, J = 6.0 Hz), 3.38 (2H, t, J = 11.2 Hz), 3.93-4.01 (2H, m), 4.27 (2H, bs), 4.83 (2H, t, J = 8.6 Hz), 7.39 (1H, bs), 7.91 (1H, s,). Mass (m/z): 406.3 (M + H)⁺, 408.1 (M + H)⁺. |

-continued

| Example Number | Chemical name and Structure | Characterization data |
|---|---|---|
| 26. | 4-Amino-5-chloro-N-{[3-(tetrahydropyran-4-ylmethyl)-3-azabicyclo[3.1.0]hex-6-yl]methyl}-2,3-dihydrobenzofuran-7-carboxamide L(+)-tartarate 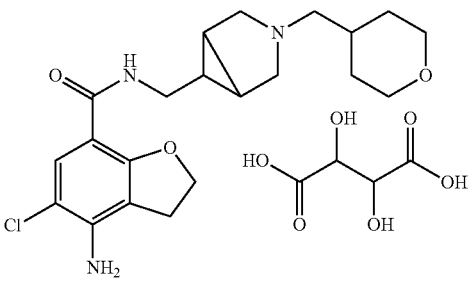 | ¹H-NMR (δ ppm): δ 0.95-1.10 (2H, m), 1.25-1.32 (1H, m), 1.33-1.42 (2H, m), 1.47-1.55 (2H, m), 1.55-1.70 (1H, m), 2.28-2.50 (4H, m), 2.99 (2H, t, J = 8.6 Hz), 3.06 (2H, t, J = 6.3 Hz), 3.30-3.50 (4H, m), 3.76 (2H, dd, J = 2.7, 11.2 Hz), 4.16 (2H, s), 4.68 (2H, t, J = 8.7 Hz), 5.84 (2H, bs), 7.42 (1H, s), 7.47 (1H, bs); Mass (m/z): 406.3 (M + H)⁺, 408.2 (M + H)⁺. |
| 27. | 4-Amino-5-chloro-N-{[3-(tetrahydropyran-4-yl)-3-azabicyclo[3.1.0]hex-6-yl]methyl}-2,3-dihydrobenzofuran-7-carboxamide 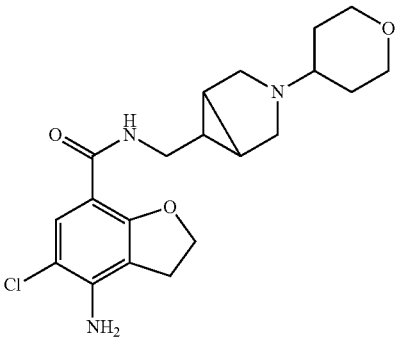 [SMILES: Nc1c(Cl)cc(C(=O)NCC2C3CN(C4CCOCC4)CC23)c2c1CCO2] | ¹H-NMR (400 MHz, CDCl₃): δ 1.30-1.35 (1H, m), 1.38-1.45 (2H, m), 1.50-1.60 (2H, m), 1.70-1.80 (2H, m), 2.25-2.35 (1H, m), 2.40 (2H, d, J = 6.9 Hz), 3.02-3.18 (4H, m), 3.32 (2H, t, J = 5.7 Hz), 3.40 (2H, t, J = 11.2 Hz), 3.92-4.0 (2H, m), 4.27 (2H, bs), 4.82 (2H, t, J = 8.6 Hz), 7.41 (1H, bs), 7.90 (1H, s); Mass (m/z): 392.3 (M + H)⁺, 394.1 (M + H)⁺. |
| 28. | 4-Amino-5-chloro-N-{[3-(tetrahydropyran-4-yl)-3-azabicyclo[3.1.0]hex-6-yl]methyl}-2,3-dihydrobenzofuran-7-carboxamide oxalate 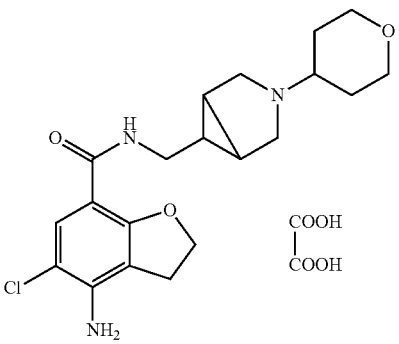 | ¹H-NMR (δ ppm): δ 1.30-1.40 (1H, m), 1.50-1.62 (2H, m), 1.70-1.90 (4H, m), 3.02 (2H, t, J = 8.6 Hz), 3.10-3.35 (9H, m), 3.88 (2H, d, J = 9.1 Hz), 4.72 (2H, t, J = 8.6 Hz), 5.90 (2H, bs), 7.47 (1H, s), 7.61 (1H, bs); Mass (m/z): 392.3 (M + H)⁺, 394.1 (M + H)⁺. |

| Example Number | Chemical name and Structure | Characterization data |
|---|---|---|
| 29. | 4-Amino-5-bromo-N-{[3-(tetrahydropyran-4-yl)-3-azabicyclo[3.1.0]hex-6-yl]methyl}-2,3-dihydrobenzofuran-7-carboxamide oxalate 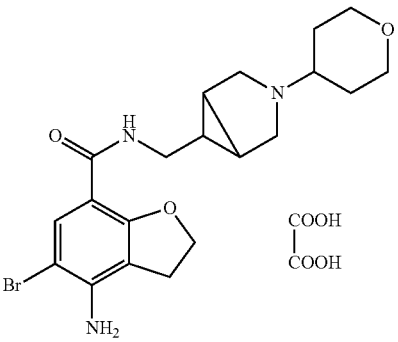 [SMILES: Nc1c(Cl)cc(C(=O)NCC2C3CN(C4CCOCC4)CC23)c2c1CCO2 ; O=C(O)C(=O)O] | $^1$H-NMR (δ ppm): δ 1.30-1.40 (1H, m), 1.42-1.58 (2H, m), 1.65-1.75 (2H, m), 1.80-1.88 (2H, m), 2.98-3.28 (9H, m), 3.35-3.55 (2H, m), 3.83-3.92 (2H, m), 4.70 (2H, t, J = 8.7 Hz), 5.83 (2H, bs), 7.58 (1H, s), 7.61 (1H, bs); Mass (m/z): 438.1 (M + H)$^+$, 436.1 (M + H)$^+$. |

Example 30: Preparation of 5-Amino-6-chloro-N-{[3-(4-hydroxytetrahydro-2H-pyran-4-ylmethyl)-3-azabicyclo[3.1.0]hex-6-yl]methyl}chroman-8-carboxamide L(+)-tartarate

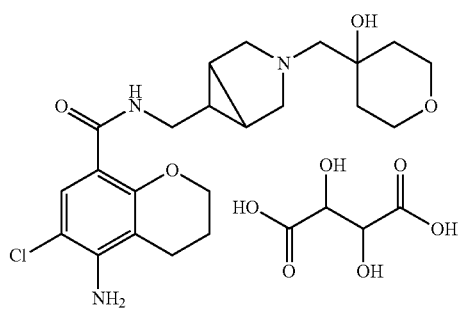

Step (i): Preparation of 5-Amino-6-chloro-N-{[3-(4-hydroxytetrahydro-2H-pyran-4-ylmethyl)-3-azabicyclo[3.1.0]hex-6-yl]methyl}chroman-8-carboxamide

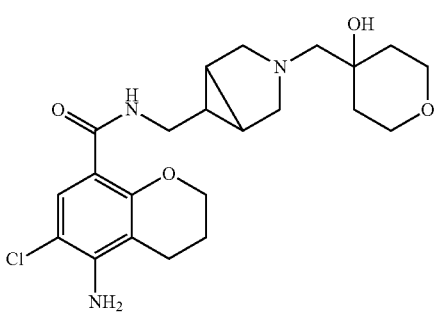 [SMILES: Nc1c(Cl)cc(C(=O)NCC2C3CN(CC4(O)CCOCC4)CC23)c2c1CCCO2]

A solution of 5-amino-6-chloro-N-{[3-azabicyclo[3.1.0]hex-6-yl]methyl}chroman-8-carboxamide (100 mg, 0.307 mmole, obtained in the preparation 8), 1,6-dioxa spiro[2.5] octane (71 mg, 0.622 mmole) and TEA (95 mg, 0.940 mole) in MeOH (10 mL) was stirred overnight at 78° C., while monitoring the progress of the reaction by TLC. After completion of the reaction, the reaction mass was concentrated and the crude residual mass, thus obtained, was further purified by flash chromatography using MeOH:TEA:CHCl$_3$ (5:2:93) to afford the title compound.

Weight: 85 mg (Yield: 62.5%).

$^1$H-NMR (δ ppm): 1.15-1.35 (6H, m), 1.42-1.52 (2H, m), 1.93-2.21 (2H, m), 2.29-2.46 (5H, m), 2.97-3.05 (4H, m), 3.50-3.53 (4H, m), 4.00 (1H, s), 4.17-4.19 (2H, m), 5.57 (2H, bs), 7.56 (1H, s), 7.97-8.01 (1H, t);

Mass (m/z): 436.4 (M+H)$^+$, 438.4 (M+H)$^+$.

Step (ii): Preparation of 5-Amino-6-chloro-N-{[3-(4-hydroxytetrahydro-2H-pyran-4-ylmethyl)-3-azabicyclo[3.1.0]hex-6-yl]methyl}chroman-8-carboxamide L(+)-tartarate A clear solution of L(+)-tartaric acid (27.5 mg, 0.183 mmole) in 2 mL MeOH was added to a stirred solution of 5-Amino-6-chloro-N-{[3-(4-hydroxytetrahydro-2H-pyran-4-ylmethyl)-3-azabicyclo[3.1.0]hex-6-yl]methyl} chroman-8-carboxamide (80 mg, 0.183 mmole, obtained in the above step) in MeOH (20 mL) at RT. The clear mass was stirred further for 2 hours at RT. The solvent was evaporated to afford solid mass. The solid mass was further triturated with DEE (2×5 mL) and dried under reduced pressure to obtain the title compound.

Weight: 96.7 mg (Yield: 89.9%).

$^1$H-NMR (δ ppm): 1.52-1.58 (3H, m), 1.61-1.68 (2H, m), 1.81-1.84 (2H, m), 2.05-2.08 (2H, m), 2.51-2.54 (2H, t), 3.03-3.04 (2H, m), 3.11-3.14 (1H, m), 3.28-3.32 (2H, m), 3.39-3.46 (4H, m), 3.70-3.75 (4H, m), 4.24-4.27 (2H, t), 4.42 (2H, s), 7.71 (1H, s).

Mass (m/z): 436.4 (M+H)$^+$, 438.4 (M+H)$^+$.

Examples 31 to 35

The compounds of Examples 31 to 35 were prepared by following the experimental procedure as described in the Example 30 given above, with some noncritical variations.

| Example Number | Chemical name and Structure | Characterization data |
|---|---|---|
| 31. | 4-Amino-5-chloro-N-{[3-(4-hydroxytetrahydro-2H-pyran-4-ylmethyl)-3-azabicyclo[3.1.0]hex-6-yl]methyl}benzofuran-7-carboxamide | $^1$H-NMR (400 MHz, CDCl$_3$): δ 1.40-1.60 (7H, m), 2.40-2.50 (2H, m), 2.60-2.70 (2H, m), 3.08-3.20 (2H, m), 3.37-3.43 (2H, m), 3.70-3.80 (4H, m), 4.64 (2H, bs), 6.79 (1H, s), 7.31 (1H, bs), 7.66 (1H, s), 8.05 (1H, s); Mass (m/z): 420.0 (M + H)$^+$, 422.0 (M + H)$^+$. |
| 32. | 4-Amino-5-chloro-N-{[3-(4-hydroxytetrahydro-2H-pyran-4-ylmethyl)-3-azabicyclo[3.1.0]hex-6-yl]methyl}benzofuran-7-carboxamide oxalate | $^1$H-NMR (δ ppm): 1.40-1.62 (5H, m), 1.65-1.76 (2H, m), 2.90-3.0 (2H, m), 3.18 (2H, t, J = 5.8 Hz), 3.53-3.63 (4H, m), 6.45 (2H, bs), 7.26 (1H, s), 7.60 (1H, s), 7.92 (2H, bs); Mass (m/z): 420.1 (M + H)$^+$, 422.2 (M + H)$^+$. |
| 33. | 4-Amino-5-chloro-N-{[1-(4-hydroxytetrahydro-2H-pyran-4-ylmethyl)-4-hydroxy-4-piperidinyl]methyl}benzofuran-7-carboxamide L(+)-tartarate | $^1$H-NMR (δ ppm): 1.41-1.55 (4H, 1.73-1.79 (2H, m), 2.66-2.69 (2H, m), 2.74-2.89 (4H, m), 3.15 (2H, s), 3.26-3.38 (4H, m), 3.57-3.62 (4H, m), 4.14 (2H, s), 6.49 (2H, bs), 7.28-7.29 (1H, m), 7.65 (1H, s), 7.70-7.75 (1H, t), 7.94-7.95 (1H, m); Mass (m/z): 438.4 (M + H)$^+$, 440.2 (M + H)$^+$. |

| Example Number | Chemical name and Structure | Characterization data |
|---|---|---|
| 34. | 4-Amino-5-chloro-N-{[3-(4-hydroxy tetrahydropyran-4-ylmethyl)-3-azabicyclo[3.1.0]hex-6-yl]methyl}-2,3-dihydrobenzofuran-7-carboxamide 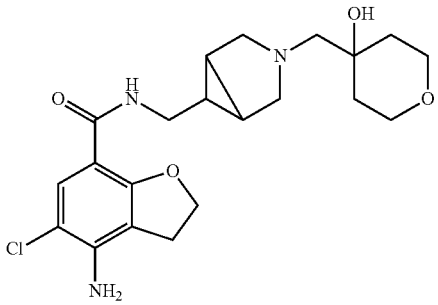 [SMILES: Nc1c(Cl)cc(C(=O)NCC2C3CN(CC4(O)CCOCC4)CC23)c2c1CCO2] | H-NMR (400 MHz, CDCl₃): δ 1.35-1.40 (1H, m), 1.40-1.45 (2H, m), 1.52-1.68 (4H, m), 2.42 (2H, s), 2.62 (2H, d, J = 8.3 Hz) 3.03-3.12 (4H, m), 3.28 (2H, t, J = 6.2 Hz), 3.70-3.80 (4H, m), 4.25 (2H, bs), 4.80 (2H, t, J = 8.7 Hz), 7.37 (1H, bs), 7.86 (1H, s). Mass (m/z): 422.3 (M + H)⁺, 424.1 (M + H)⁺. |
| 35. | 4-Amino-5-chloro-N-{[3-(4-hydroxytetrahydropyran-4-ylmethyl)-3-azabicyclo[3.1.0]hex-6-yl]methyl}-2,3-dihydrobenzofuran-7-carboxamide oxalate 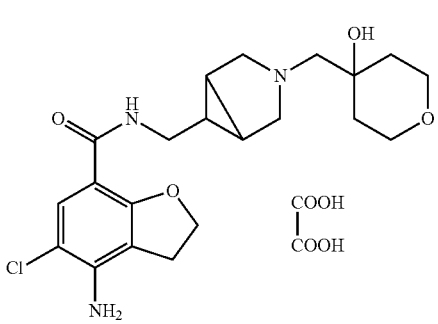 [SMILES: Nc1c(Cl)cc(C(=O)NCC2C3CN(CC4(O)CCOCC4)CC23)c2c1CCO2 ; O=C(O)C(=O)O] | ¹H-NMR (δ ppm): 1.35-1.65 (7H, m), 2.50 (2H, s), 2.80-2.90 (2H, m), 3.03 (2H, t, J = 8.7 ;Hz), 3.12 (2H, t, J = 6.1 Hz), 3.55-3.68 (6H, m), 4.72 (2H, t, J = 8.7 Hz), 5.89 (2H, s), 7.47 (1H, s), 7.57 (1H, bs); Mass (m/z): 422.3 (M + H)⁺, 424.1 (M + H)⁺. |

Example 36: Preparation of 5-Amino-6-chloro-N-{[3-(4-fluorotetrahydro-2H-pyran-4-yl methyl)-3-azabicyclo[3.1.0]hex-6-yl] methyl}chroman-8-carboxamide L(+)-tartarate Step (i) Preparation of 5-Amino-6-chloro-N-{[3-(4-fluorotetrahydro-2H-pyran-4-yl methyl)-3-azabicyclo[3.1.0]hex-6-yl] methyl}chroman-8-carboxamide

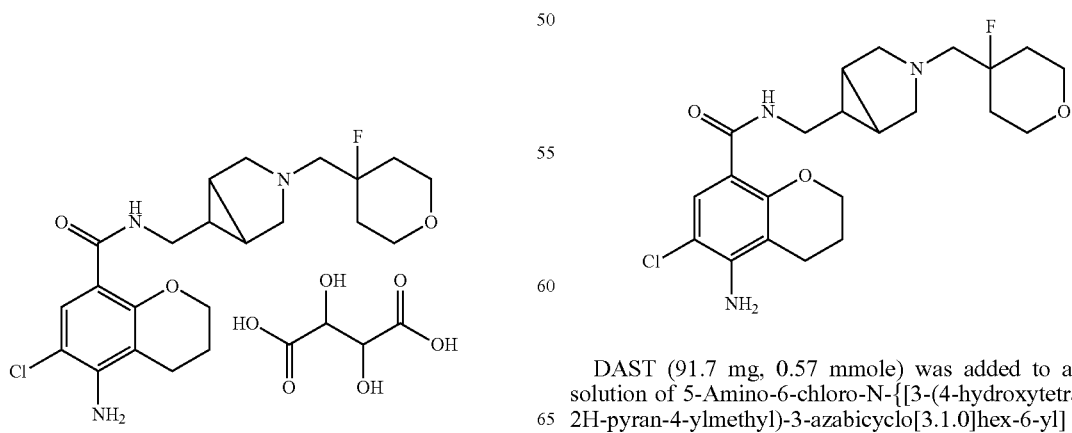

DAST (91.7 mg, 0.57 mmole) was added to a stirred solution of 5-Amino-6-chloro-N-{[3-(4-hydroxytetrahydro-2H-pyran-4-ylmethyl)-3-azabicyclo[3.1.0]hex-6-yl] methyl}chroman-8-carboxamide (100 mg, 0.228 mmole, obtained in the step (i) of Example 30, in DCM (10 mL) at −40° C. Then reaction mass temperature was slowly raised to RT and stirred for overnight at same temperature. The progress of the reaction was monitored by TLC. After completion of the reaction, the mass was quenched in chilled water (10 mL). The mass pH was adjusted to pH ~9.5 using aqueous NH$_3$, the compound was extracted with DCM (3×5 mL). The combined organic phase was washed with water (5 mL), brine solution (5 mL) and dried over Na$_2$SO$_4$. The organic phase was concentrated on rotavacuum to obtain the crude residue, which was further purified by flash chromatography using TEA:MeOH:CHCl$_3$ (0.5:2:97.5) to afford the title compound.

Weight: 64 mg (Yield: 64%).

$^1$H-NMR (δ ppm): 1.12-1.21 (2H, m), 1.28-1.31 (2H, m), 1.43-1.54 (1H, m), 1.55-1.65 (2H, m), 1.82-1.95 (2H, m), 2.13-2.22 (2H, m), 2.23-2.35 (2H, d), 2.42-2.49 (1H, m), 2.53-2.59 (1H, m), 2.95-2.98 (2H, m), 3.08-3.12 (2H, t), 3.42-3.56 (2H, m), 3.58-3.60 (2H, m), 4.18-4.21 (2H, t), 5.59 (2H, bs), 7.58 (1H, s), 7.98-8.01 (1H, t);

Mass (m/z): 438.5 (M+H)$^+$, 440.4 (M+H)$^+$.

Step (ii): Preparation of 5-Amino-6-chloro-N-{[3-(4-fluorotetrahydro-2H-pyran-4-ylmethyl)-3-azabicyclo[3.1.0]hex-6-yl]methyl}chroman-8-carboxamide L(+)-tartarate A clear solution of L(+)-tartaric acid (20.3 mg, 0.135 mole) in 1 mL MeOH was added to a stirred solution of 5-Amino-6-chloro-N-{[3-(4-fluorotetrahydro-2H-pyran-4-ylmethyl)-3-azabicyclo[3.1.0]hex-6-yl]methyl}chroman-8-carboxamide (60 mg, 0.137 mmole, obtained in the above step) in MeOH (5 mL). The clear mass was stirred further for 2 hours at RT. The solvent was evaporated to afford solid mass. The solid mass was further triturated with DEE (2×5 mL) and dried under reduced pressure to obtain the title compound.

Weight: 70.2 mg (Yield: 87.1%).

$^1$H-NMR (δ ppm): 1.42-1.52 (1H, m), 1.62-1.64 (2H, m), 1.69-1.73 (1H, m), 1.78-1.81 (3H, m), 2.06-2.21 (2H, m), 2.54-2.57 (2H, t), 2.98-3.10 (4H, m), 3.25-3.31 (4H, m), 3.64-3.70 (2H, m), 3.76-3.79 (2H, m), 4.27-4.30 (2H, t), 4.48 (2H, s), 7.73 (1H, s);

Mass (m/z): 438.5 (M+H)$^+$, 440.4 (M+H)$^+$.

Example 37: Preparation of 5-Amino-6-chloro-N-{[3-(2-hydroxy-2-methyl propyl)-3-azabicyclo[3.1.0]hex-6-yl]methyl}chroman-8-carboxamide L(+)-tartarate

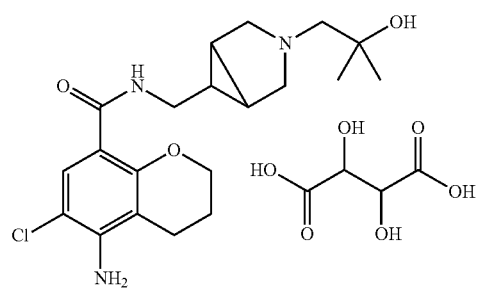

Step (i): Preparation of 5-Amino-6-chloro-N-{[3-(2-hydroxy-2-methyl propyl)-3-azabicyclo[3.1.0]hex-6-yl]methyl}chroman-8-carboxamide

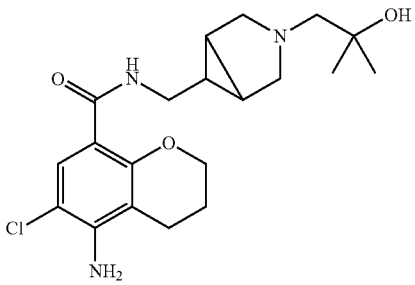 [SMILES: CC(C)(O)CN1CC2C(CNC(=O)c3cc(Cl)c(N)c4c3OCCC4)C2C1]

A solution of 5-amino-6-chloro-N-{[3-azabicyclo[3.1.0]hex-6-yl]methyl}chroman-8-carboxamide (0.30 gram, 0.947 mmole, obtained in the preparation 8), isobutyleneoxide (0.38 grams, 5.33 mmole) and TEA (0.54 grams, 5.33 mmole) in MeOH (15 mL) was stirred overnight at 75° C. The progress of the reaction was monitored by TLC. After completion of the reaction (TLC), the reaction mass was concentrated on rotavacuum to obtain the crude residue, which was further purified by flash chromatography using TEA:MeOH:CHCl$_3$ (0.25:0.75:99) to afford the title compound.

Weight: 0.69 grams (Yield: 67%).

$^1$H-NMR (δ ppm): 1.00 (6H, s), 1.09-1.18 (2H, m), 1.21-1.34 (2H, m), 1.94-1.96 (2H, m), 2.25-2.28 (1H, m), 2.31-2.38 (1H, m), 2.44-2.49 (2H, m), 3.00-3.08 (2H, m), 3.13-3.18 (2H, m), 3.38-3.49 (1H, m), 3.96 (1H, bs), 4.19-4.21 (2H, t), 5.59 (2H, bs), 7.59 (1H, s), 7.94-7.98 (1H, t);

Mass (m/z): 394.1 (M+H)$^+$, 396.2 (M+H)$^+$.

Step (ii): Preparation of 5-Amino-6-chloro-N-{[3-(2-hydroxy-2-methyl propyl)-3-azabicyclo[3.1.0]hex-6-yl]methyl}chroman-8-carboxamide L(+)-tartarate A clear solution of L(+)-tartaric acid (0.155 gram, 1.03 mole) in 2 mL MeOH was added to a stirred solution of 5-amino-6-chloro-N-{[3-(2-hydroxy-2-methyl propyl)-3-azabicyclo[3.1.0]hex-6-yl]methyl}chroman-8-carboxamide (0.42 gram, 1.07 mmole, obtained in the above step) in MeOH (2 mL) at RT. The clear mass was stirred further for 2 hours at RT. The solvent was evaporated to afford solid mass. The solid mass was further triturated with DEE (2×3 mL) and dried under vacuum to obtain the title compound.

Weight: 0.524 gram (Yield: 89%).

$^1$H-NMR (δ ppm): 1.26 (6H, s), 1.49-1.58 (2H, m), 1.78-1.88 (2H, m), 2.08-2.10 (2H, m), 2.54-2.57 (2H, t), 3.00-3.13 (4H, m), 3.31-3.48 (3H, m), 4.27-4.29 (2H, t), 4.42 (2H, s), 7.73 (1H, s);

Mass (m/z): 394.0 (M+H)$^+$, 396.0 (M+H)$^+$.

Example 38: Preparation of 4-Amino-5-chloro-N-{[4-fluoro-1-(2-hydroxy-2-methyl propyl)-4-piperidinyl]methyl}benzofuran-7-carboxamide

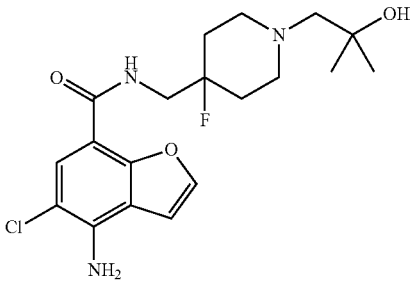 [SMILES: CC(C)(O)CN1CCC(F)(CNC(=O)c2cc(Cl)c(N)c3ccoc23)CC1]

To a clear solution of 4-amino-5-chloro-N-[4-fluoro-(4-piperidinyl)methyl]benzofuran-7-carboxamide (19.4 gram, 0.0595 mole, obtained in the preparation 13) in MeOH (600 mL), was added TEA (24.94 mL, 0.178 mole) and isobutyleneoxide (26.7 mL, 0.297 mole, d=0.808) at RT. Reaction mixture was heated to reflux for 7 hours under nitrogen atmosphere and then cooled to RT. The reaction mass was concentrated on rotavacuum to obtain the crude residue (28.9 gm), which was further purified by flash chromatography using methanolic $NH_3$:MeOH:$CHCl_3$ (2:3:95) to afford the title compound in two fractions.

Weight: 20.6 grams (First fraction 18.4 grams and Second fraction 2.2 grams) (Yield: 87%).

$^1$H-NMR (δ ppm): 1.05 (6H, s), 1.62-1.77 (4H, m), 2.18 (2H, s), 2.34-2.39 (2H, m), 2.69-2.72 (2H, m), 3.52-3.59 (2H, dd), 4.04 (1H, s), 6.49 (2H, bs), 7.26 (1H, d; J=2 Hz), 7.63 (1H, s), 7.74-7.77 (1H, t), 7.95 (1H, d; J=1.6 Hz);

Mass (m/z): 398.2 (M+H)$^+$, 400.4 (M+H)$^+$.

Example 39: Preparation of 4-Amino-5-chloro-N-{[4-fluoro-1-(2-hydroxy-2-methyl propyl)-4-piperidinyl]methyl}benzofuran-7-carboxamide hydrochloride

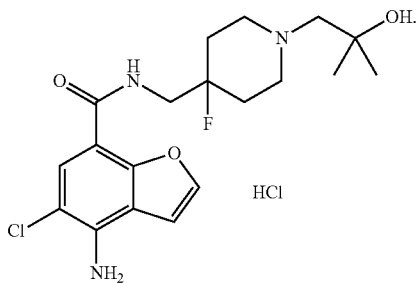 [SMILES: CC(C)(O)CN1CCC(F)(CNC(=O)c2cc(Cl)c(N)c3ccoc23)CC1 ; Cl]

To a clear solution of 4-amino-5-chloro-N-{[4-fluoro-1-(2-hydroxy-2-methyl propyl)-4-piperidinyl]methyl}benzofuran-7-carboxamide (19.5 grams, 0.0490 mole, obtained in the Example 38) in DCM (390 mL) was added ethanolic HCl (19.2%, 12.06 mL, 0.0637 mole) drop wise at RT. The clear mass was stirred further for 1 hour at RT under nitrogen atmosphere and the solvent was removed under vacuum to afford solid mass. The solid mass was triturated with DEE (1×400 mL), ether layer decanted and dried under vacuum to obtain the title compound as HCl salt (21.30 gram). This salt (21.012 gram) was taken in a separate flask to which ethanol (105 mL, 5 volume/weight) was added at RT and heated to reflux. At reflux temperature, DM water (12 mL) was added drop wise to get clear solution. Heating was discontinued and the content was allowed to cool at its own under stirring. At 45° C. solid formation was observed. It was cooled further to RT and then to 10° C. The solid obtained was filtered and dried under high vacuum.

Weight: 16.96 gram (Yield: 80%).

$^1$H-NMR (δ ppm): 1.25 (6H, s), 1.94-2.39 (4H, m), 3.11-3.21 (4H, m), 3.56-3.74 (4H, m), 5.28 (1H, s), 6.52 (2H, s), 7.32 (1H, s), 7.65 (1H, s), 7.90-7.94 (2H, bs), 9.70-9.91 (1H, d);

Mass (m/z): 398.4 (M+H)$^+$, 400.3 (M+H)$^+$.

Example 40: Preparation of 5-Amino-6-chloro-N-{[1-(2-hydroxy-2-methyl propyl)-4-piperidinyl]methyl}chroman-8-carboxamide

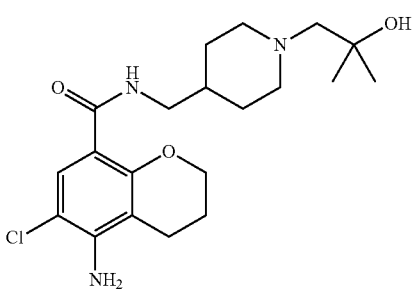 [SMILES: CC(C)(O)CN1CCC(CNC(=O)c2cc(Cl)c(N)c3c2OCCC3)CC1]

A solution of N-[(piperidin-4-yl) methyl]-5-amino-6-chloro chroman-8-carboxamide (0.40 gram, 1.236 mmole, obtained in the preparation 7), isobutyleneoxide (0.17 grams, 2.36 mmole) and TEA (0.24 grams, 2.37 mmole) in MeOH (15 mL) was stirred overnight at 75° C. The progress of the reaction was monitored by TLC. After completion of the reaction (TLC), the reaction mass was concentrated on rota vacuum to obtain the crude residue, which was further purified by flash chromatography using TEA:MeOH:$CHCl_3$ (0.25:0.75:99) to afford the title compound.

Weight; 0.38 grams (Yield: 79.16%).

$^1$H-NMR (δ ppm): 1.12-1.22 (8H, m), 1.40-1.54 (2H, m), 1.65-1.73 (2H, m), 1.93-1.97 (2H, m), 2.03-2.13 (2H, m), 2.44-2.49 (2H, t), 2.89-3.01 (3H, m), 3.13-3.21 (2H, m), 3.97 (1H, bs), 4.17-4.20 (2H, t), 5.58 (2H, s), 7.56 (1H, s), 7.92-8.00 (1H, m);

Mass (m/z): 396.3 (M+H)$^+$, 398.3 (M+H)$^+$.

Example 41: Preparation of 5-Amino-6-chloro-N-{[1-(2-hydroxy-2-methyl propyl)-4-piperidinyl]methyl}chroman-8-carboxamide L(+)-tartarate

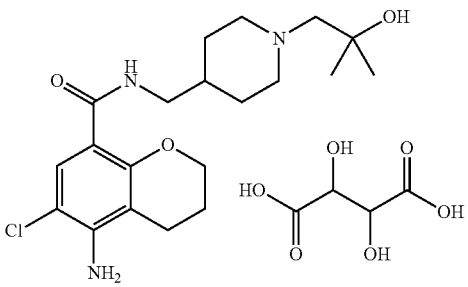

A solution of L(+)-tartaric acid (0.04 gram, 0.266 mmole) in MeOH (5 mL) was added to a stirred solution of 5-amino-6-chloro-N-{[1-(2-hydroxy-2-methylpropyl)-4-piperidinyl]methyl}chroman-8-carboxamide (0.12 gram, 0.303 mmole, obtained in the Example 40) in MeOH (10 mL). The clear mass, thus obtained, was stirred further for 2 hours at RT. The solvent was evaporated to afford solid mass. The solid mass was triturated with DEE (10 mL) and dried under reduced pressure to obtain the title compound.

Weight: 0.15 gram (Yield: 93.75%).

$^1$H-NMR (δ ppm): 1.29-1.34 (8H, m), 1.65-1.71 (2H, m), 1.92-1.95 (2H, m), 2.06-2.11 (2H, m), 2.54-2.57 (2H, t), 3.14-3.22 (2H, m), 3.33-3.36 (3H, m), 3.58-3.82 (2H, m), 4.26-4.29 (2H, t), 4.48 (2H, s) 7.72 (1H, s);

Mass (m/z): 396.2 (M+H)$^+$, 398.3 (M+H)$^+$.

Example 42: Preparation of 4-Amino-5-chloro-N-{[3-(2-hydroxy-2-methylpropyl)-3-azabicyclo[3.1.0]hex-6-yl]methyl}-2,3-dihydrobenzofuran-7-carboxamide oxalate

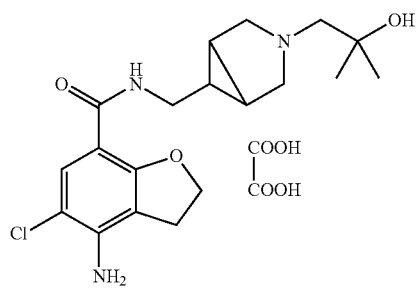

Step (i): Preparation of 4-Amino-5-chloro-N-{[3-(2-hydroxy-2-methylpropyl)-3-azabicyclo[3.1.0]hex-6-yl]methyl}-2,3-dihydrobenzofuran-7-carboxamide To a stirred solution of 4-amino-5-chloro-N-{[3-azabicyclo[3.1.0]hex-6-yl]methyl}-2,3-dihydrobenzofuran-7-carboxamide hydrochloride (160.0 mg, 0.46 mmol; obtained in the preparation 19), in MeOH (4.6 mL), TEA (0.4 mL, 2.76 mmole) followed by isobutyleneoxide (0.2 mL, 2.3 mmole) were added. The reaction mixture was stirred for 16 hours at 65° C. and concentrated on rotavacuum to obtain the crude residue, which was purified by silica gel column chromatography to afford the title compound as gummy liquid.

Weight: 160 mg (Yield: 91%)

$^1$H-NMR (δ ppm): 1.13 (6H, s), 1.40-1.46 (1H, m), 1.55-1.70 (2H, m), 2.41 (2H, s), 2.58 (2H, d, J=8.5 Hz), 3.07 (2H, t, J=8.6 Hz), 3.13 (2H, d, J=8.8 Hz), 3.28 (2H, t, J 5.9 Hz), 4.24 (2H, bs), 4.80 (2H, t, J=8.6 Hz), 7.37 (1H, bs), 7.87 (1H, s);

Mass (m/z): 380.2, 382.2 (M+H)$^+$.

Step (ii): Preparation of 4-Amino-5-chloro-N-{[3-(2-hydroxy-2-methylpropyl)-3-azabicyclo[3.1.0]hex-6-yl]methyl} 2,3-dihydrobenzofuran-7-carboxamide oxalate To a stirred solution of 4-Amino-5-chloro-N-{[3-(2-hydroxy-2-methylpropyl)-3-azabicyclo[3.1.0]hex-6-yl]methyl}-2,3-dihydrobenzofuran-7-carboxamide (160.0 mg, 0.42 mmole, obtained in the above step) in isopropanol (6.0 mL) at RT, oxalic acid (37.0 mg, 0.42 mmole) was added. The reaction mass was stirred for 4 hours before the volatiles were removed under reduced pressure. The crude mass was triturated with solvent ether several times to obtain the above titled compound as white solid.

Weight: 160.3 mg (Yield: 89%)

$^1$H-NMR (δ ppm): 1.11 (6H, s), 1.50-1.60 (1H, m), 1.60-1.72 (2H, m), 2.85 (2H, s), 3.02 (2H, t, J=8.6 Hz), 3.12 (2H, t, J=6.1 Hz), 3.20-3.50 (4H, m), 4.71 (2H, t, J=8.6 Hz), 5.88 (2H, bs), 7.46 (1H, s), 7.56 (1H, bs);

Mass (m/z): 380.1, 382.3 (M+H)$^+$.

Examples 43 to 54

The compounds of Examples 43 to 54 were prepared by following the experimental procedure as described in the Examples 36 to 42 given above, with some noncritical variations.

| Example Number | Chemical name and Structure | Characterization data |
|---|---|---|
| 43. | 5-Amino-6-chloro-N-{[4-fluoro-1-(2-hydroxy-2-methylpropyl)-4-piperidinyl]methyl}chroman-8-carboxamide | $^1$H-NMR (δ ppm): 1.05 (6H, s), 1.58-1.73 (4H, m), 1.94-1.97 (2H, m), 2.18 (2H, s), 2.33-2.38 (2H, t), 2.44-2.49 (2H, m), 2.67-2.70 (2H, m), 3.34-3.52 (2H, m), 4.03 (1H, s), 4.19-4.21 (2H, t), 5.64 (2H, s), 7.60 (1H, s), 7.98-8.01 (1H, t); Mass (m/z): 414.2 (M + H)$^+$, 416.2 (M + H)$^+$. |

| Example Number | Chemical name and Structure | Characterization data |
|---|---|---|
| 44. | 5-Amino-6-chloro-N-{[4-fluoro-1-(2-hydroxy-2-methylpropyl)-4-piperidinyl]methyl}chroman-8-carboxamide L(+)-tartarate 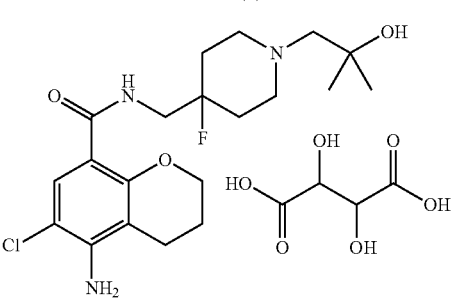 | $^1$H-NMR (δ ppm): 1.32 (6H, s), 2.03-2.14 (6H, m), 2.54-2.58 (2H, t), 3.04 (2H, s), 3.19-3.27 (2H, m), 3.45-3.48 (2H, m), 3.66-3.71 (2H, m), 4.27-4.30 (2H, t), 4.41 (2H, s), 7.75 (1H, s); Mass (m/z): 414.3 (M + H)$^+$, 416.3 (M + H)$^+$. |
| 45. | 5-Amino-6-bromo-N-{[1-(2-hydroxy-2-methylpropyl)-4-piperidinyl]methyl}chroman-8-carboxamide 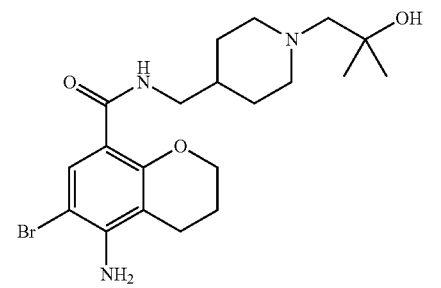 | $^1$H-NMR (δ ppm): 1.02 (6H, s), 1.10-1.19 (2H, m), 1.30-1.38 (1H, m), 1.49-1.51 (2H, m), 1.91-1.97 (2H, m), 2.00-2.11 (2H, t), 2.42-2.46 (2H, m), 2.69 (2H, s), 2.81-2.87 (2H, m), 3.08-3.11 (2H, t) 3.95 (1H, s), 4.15-4.17 (2H, t), 5.47 (2H, bs), 7.69 (1H, s), 7.87-7.89 (1H, t); Mass (m/z): 440.1 (M + H)$^+$, 442.1 (M + H)$^+$. |
| 46. | 5-Amino-6-bromo-N-{[1-(2-hydroxy-2-methylpropyl)-4-piperidinyl]methyl}chroman-8-carboxamide L(+)-tartarate 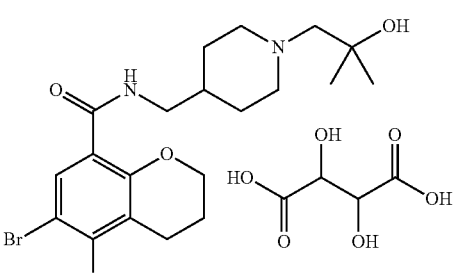 | $^1$H-NMR (δ ppm): 1.31 (6H, s), 1.62-1.71 (2H, m), 1.82-1.98 (3H, m), 2.06-2.12 (2H, m), 2.55-2.58 (2H, t), 2.86 (1H, s), 3.00 (1H, s), 3.03-3.18 (4H, m), 3.53-3.72 (2H, m), 4.27-4.29 (2H, t), 4.41 (2H, s), 7.88 (1H, s), 8.34-8.36 (1H, t); Mass (m/z): 440.2 (M + H)$^+$, 442.2 (M + H)$^+$. |
| 47. | 5-Amino-6-bromo-N-{[4-fluoro-1-(2-hydroxy-2-methylpropyl)-4-piperidinyl]methyl}chroman-8-carboxamide 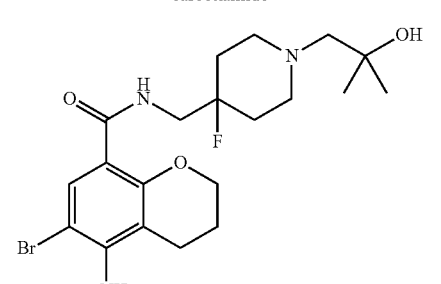 | $^1$H-NMR (δ ppm): 1.05 (6H, s), 1.63-1.68 (4H, m), 1.95-1.97 (2H, m), 2.18 (2H, s), 2.33-2.36 (2H, m), 2.45-2.49 (2H, m), 2.68-2.75 (2H, m), 3.45-3.52 (2H, m), 4.04 (1H, bs), 4.19-4.21 (2H, t), 5.57 (2H, bs), 7.76 (1H, s), 7.98-8.00 (1H, t); Mass (m/z): 458.2 (M + H)$^+$, 460.2 (M + H)$^+$. |

-continued

| Example Number | Chemical name and Structure | Characterization data |
|---|---|---|
| 48. | 5-Amino-6-bromo-N-{[4-fluoro-1-(2-hydroxy-2-methylpropyl)-4-piperidinyl]methyl}chroman-8-carboxamide L(+)-tartarate | $^1$H-NMR (δ ppm): 1.32 (6H, s), 2.03-2.17 (6H, m), 2.55-2.58 (2H, t), 3.05 (2H, s), 3.13-3.25 (2H, m), 3.47-3.48 (2H, m), 3.66-3.71 (2H, m), 4.27-4.30 (2H, t), 4.42 (2H, s), 7.91 (1H, s); Mass (m/z): 458.2 (M + H)$^+$, 460.2 (M + H)$^+$. |
| 49. | 4-Amino-5-chloro-N-{[1-(2-hydroxy-2-methylpropyl)-4-piperidinyl]methyl}benzofuran-7-carboxamide L(+)-tartarate | $^1$H-NMR (δ ppm): 1.12 (6H, s), 1.37-1.39 (2H, m), 1.66-1.69 (3H, m), 2.49-2.54 (2H, m), 3.15-3.19 (4H, m), 3.20-3.23 (3H, m), 4.0 (2H, s), 6.43 (2H, bs), 7.25-7.26 (1H, d, J = 1.98 Hz), 7.58 (1H, s), 7.80-78.3 (1H, t), 7.91-7.92 (1H, d; J = 1.96 Hz); Mass (m/z): 380.2 (M + H)$^+$, 382.3 (M + H)$^+$. |
| 50. | 4-Amino-5-chloro-N-{[4-fluoro-1-(2-hydroxy-2-methylpropyl)-4-piperidinyl]methyl}benzofuran-7-carboxamide L(+)-tartarate | $^1$H-NMR (δ ppm): 1.06 (6H, s), 1.72-1.76 (4H, m), 2.35 (2H, s), 2.50-2.51 (2H, m), 2.83-2.89 (2H, m), 3.13 (1H, s), 3.52-3.58 (2H, m), 4.16 (2H, s), 6.47 (2H, bs), 7.24 (1H, d; J = 2.02 Hz), 7.61 (1H, s), 7.75-7.78 (1H, t), 7.92-7.93 (1H, d; J = 2.00 Hz); Mass (m/z): 398.2 (M + H)$^+$, 400.4 (M + H)$^+$. |
| 51. | 4-Amino-5-chloro-N-{[3-(2-hydroxy-2-methylpropyl)-3-azabicyclo[3.1.0]hex-6-yl]methyl}benzofuran-7-carboxamide L(+)-tartarate | $^1$H-NMR (δ ppm): 1.03 (6H, s), 1.40 (2H, s), 2.41-2.45 (2H, m), 2.56-2.59 (2H, m), 3.09-3.15 (4H, m), 3.34-3.39 (2H, m), 4.18 (2H, s), 6.43 (2H, bs), 7.25 (1H, m), 7.60 (1H, s), 7.84-7.85 (1H, t), 7.92-7.93 (1H, m); Mass (m/z): 378.2 (M + H)$^+$, 380.2 (M + H)$^+$. |

| Example Number | Chemical name and Structure | Characterization data |
|---|---|---|
| 52. | 4-Amino-5-chloro-2-methyl-N-{[1-(2-hydroxy-2-methylpropyl)-4-piperidinyl]methyl}benzofuran-7-carboxamide L(+)-tartarate | $^1$H-NMR (δ ppm): 1.33 (6H, s), 1.70-1.76 (2H, m), 1.96-1.99 (3H, m), 2.50 (3H, s), 3.10-3.16 (4H, m), 3.44-3.45 (2H, m), 3.64-3.72 (2H, m), 4.39 (2H, s), 6.67 (1H, m), 7.66 (1H, s); Mass (m/z): 394.2 (M + H)$^+$, 396.1 (M + H)$^+$. |
| 53. | 4-Amino-5-chloro-2-methyl-N-{[4-fluoro-1-(2-hydroxy-2-methylpropyl)-4-piperidinyl]methyl}benzofuran-7-carboxamide L(+)-tartarate | $^1$H-NMR (δ ppm): 1.09 (6H, s), 1.75-1.88 (4H, m), 2.40 (2H, s), 2.43 (3H, s), 2.53-2.56 (2H, m), 2.87-2.91 (2H, m), 3.15 (1H, s), 3.54-3.60 (2H, m), 4.20 (2H, s), 6.33 (2H, bs), 6.85 (1H, s), 7.54 (1H, s), 7.75-7.78 (1H, t); Mass (m/z): 412.2 (M + H)$^+$, 414.1 (M + H)$^+$. |
| 54. | 4-Amino-5-chloro-2-methyl-N-{[3-(2-hydroxy-2-methylpropyl)-3-azabicyclo[3.1.0]hex-6-yl]methyl}benzofuran-7-carboxamide | $^1$H-NMR (δ ppm): 1.00 (6H, s), 1.32-1.38 (3H, m), 2.25 (2H, s), 2.33-2.35 (2H, m), 2.44 (3H, s), 3.02-3.04 (2H, m), 3.13-3.16 (2H, m), 3.96 (1H, s), 6.27 (2H, bs), 6.83 (1H, s), 7.50 (1H, s), 7.77-7.80 (1H, t); Mass (m/z): 392.2 (M + H)$^+$, 394.2 (M + H)$^+$. |

Example 55: Preparation of 5-Amino-6-chloro-N-{[1-(2-fluoro-2-methyl propyl)-4-piperidinyl]methyl}chroman-8-carboxamide

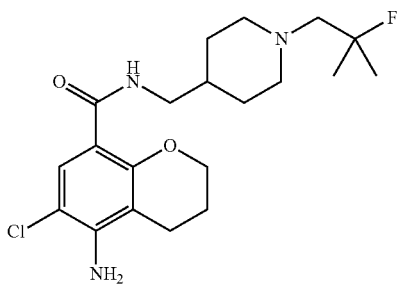 [SMILES: CC(C)(F)CN1CCC(CNC(=O)c2cc(Cl)c(N)c3c2OCCC3)CC1]

DAST (0.15 grams, 0.924 mmole) was added to a stirred solution of 5-amino-6-chloro-N-{[1-(2-hydroxy-2-methyl propyl)-4-piperidinyl]methyl}chroman-8-carboxamide (0.30 gram, 0.947 mmole, obtained in the Example 40) in DCM (10 mL) at −30° C. Then reaction mass temperature was slowly raised to RT and stirred for overnight at same temperature. The progress of the reaction was monitored by TLC. The mass was quenched in chilled water (10 mL). The mass pH was adjusted to pH ~9.5 using aqueous $NH_3$, the compound was extracted with DCM (3×5 mL). The combined organic phase was washed with water (5 mL), brine solution (5 mL) and dried over $Na_2SO_4$. The organic phase was concentrated under vacuum to obtain the crude residue, which was further purified by flash chromatography using TEA:MeOH:$CHCl_3$ (0.5:2:97.5) to afford the title compound.

Weight: 0.052 gram (Yield: 52%).

$^1$H-NMR (δ ppm): 1.27-1.33 (6H, m), 1.35-1.46 (4H, m), 1.82-1.92 (2H, m), 2.06-2.12 (3H, m), 2.54-2.57 (2H, t), 3.18-3.26 (6H, m), 4.26-4.29 (2H, t), 4.59 (2H, bs), 7.72 (1H, s), 8.33-8.37 (1H, t); Mass (m/z): 398.3 (M+H)$^+$, 400.3 (M+H)$^+$.

Examples 56 to 57

The compounds of Examples 56 to 57 were prepared by following the experimental procedure as described in the Example 55 given above, with some noncritical variations.

| Example Number | Chemical name and Structure | Characterization data |
|---|---|---|
| 56. | 5-Amino-6-chloro-N-{[1-(2-fluoro-2-methylpropyl)-4-fluoro-4-piperidinyl]methyl}chroman-8-carboxamide | $^1$H-NMR (δ ppm): 1.25-1.31 (6H, m), 1.58-1.69 (4H, m), 1.94-1.97 (2H, m), 2.33-2.36 (2H, m), 2.39 (2H, s), 2.45-2.49 (2H, m), 2.62-2.67 (2H, m, 3.46-3.53 (2H, m), 4.19-4.21 (2H, t), 5.65 (2H, bs), 7.60 (1H, s), 7.99-8.02 (1H, t); Mass (m/z): 416.3 (M + H)$^+$, 418.2 (M + H)$^+$. |
| 57. | 5-Amino-6-chloro-N-{[1-(2-fluoro-2-methylpropyl)-4-fluoro-4-piperidinyl]methyl}chroman-8-carboxamide L(+)-tartarate | $^1$H-NMR (δ ppm): 1.40-1.45 (6H, m), 1.86-1.99 (4H, m), 2.07-2.13 (2H, m), 2.54-2.58 (2H, t), 2.85-2.97 (4H, m), 3.08-3.13 (2H, m), 3.58-3.62 (2H, m), 4.32-4.35 (2H, t), 4.47 (2H, s), 7.75 (1H, s); Mass (m/z): 416.2 (M + H)$^+$, 418.3 (M + H)$^+$. |

Example 58: Preparation of 5-Amino-6-chloro-N-{[3-(3-hydroxy-2,2-dimethyl propyl)-3-azabicyclo[3.1.0]hex-6-yl]methyl}chroman-8-carboxamide L(+)-tartarate

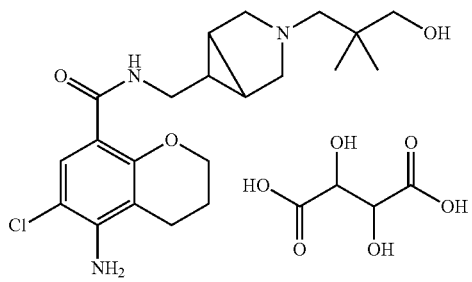

Step (i): Preparation of 5-Amino-6-chloro-N-{[3-(3-hydroxy-2,2-dimethylpropyl)-3-azabicyclo[3.1.0]hex-6-yl]methyl}chroman-8-carboxamide

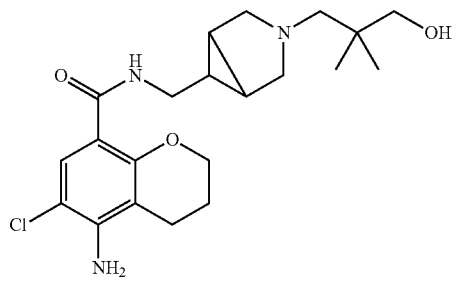 [SMILES: CC(C)(CO)CN1CC2C(CNC(=O)c3cc(Cl)c(N)c4c3OCCC4)C2C1]

A solution of 5-Amino-6-chloro-N-{[3-azabicyclo[3.1.0]hex-6-yl] methyl} chroman-8-carboxamide (0.30 gram, 0.947 mmole, obtained in the preparation 8), 3-bromo-2,2-dimethyl propan-1-ol (0.047 grams, 0.376 mmole), $K_2CO_3$ (0.086 grams, 0.623 mmole) and potassium iodide (0.086 grams, 0.623 mmole) in acetonitrile (15 mL) was stirred overnight at 85° C. The reaction mass was concentrated and the obtained slurry was quenched in water (30 mL) and the compound was extracted with DCM (3×15 mL). The combined organic phase was washed with water (15 mL), brine solution (15 mL) and dried over $Na_2SO_4$. The organic phase was concentrated on rotavacuum to obtain the crude residue, which was further purified by flash chromatography using TEA:MeOH:CHCl3 (1:3:96) to afford the title compound.

Weight: 0.07 grams (Yield: 62%).

$^1$H-NMR (δ ppm): 0.72 (6H, s), 1.22-1.32 (4H, s), 1.94-1.98 (2H, m), 2.23-2.25 (1H, m), 2.40-2.49 (4H, m), 2.94-2.98 (2H, m), 3.06-3.12 (4H, m), 4.18-4.21 (2H, t), 4.39-4.52 (1H, m), 5.57 (2H, bs), 7.59 (1H, s), 7.97-8.00 (1H, t); Mass (m/z): 408.2 $(M+H)^+$, 410.2 $(M+H)^+$.

Step (ii): Preparation of 5-Amino-6-chloro-N-{[3-(3-hydroxy-2,2-dimethyl propyl)-3-azabicyclo[3.1.0]hex-6-yl]methyl}chroman-8-carboxamide L(+)-tartarate A clear solution of L(+)-tartaric acid (0.155 gram, 1.03 mole) in 2 mL MeOH was added to a stirred solution of 5-Amino-6-chloro-N-{[3-(3-hydroxy-2,2-dimethyl propyl)-3-azabicyclo[3.1.0]hex-6-yl]methyl}chroman-8-carboxamide (0.42 gram, 1.07 mmole, obtained in the above step) in MeOH (2 mL) at RT. The clear mass was stirred further for 2 hours at RT. The solvent was evaporated to afford solid mass. The solid mass was further triturated with DEE (2×3 mL) and dried under vacuum to obtain the title compound.

Weight: 0.524 gram (Yield: 89%).

$^1$H-NMR (δ ppm): 0.93 (6H, s), 1.18-1.38 (2H, m), 1.82-1.84 (2H, m), 2.06-2.12 (3H, m), 2.54-2.57 (3H, m), 3.06-3.15 (3H, m), 3.33-3.54 (4H, m), 4.27-4.29 (2H, t), 4.41 (2H, s), 7.73 (1H, s); Mass (m/z): 408.2 $(M+H)^+$, 410.2 $(M+H)^+$.

Examples 59

The compound of Example 59 was prepared by following the experimental procedure as described in the Example 58 given above, with some noncritical variations.

| Example Number | Chemical name and Structure | Characterization data |
|---|---|---|
| 59. | 4-Amino-5-chloro-2-methyl-N-{[1-(3-hydroxy-2,2-dimethylpropyl)-4-piperidinyl]methyl}benzofuran-7-carboxamide | $^1$H-NMR (δ ppm): 1.22 (6H, s), 1.32-1.57 (3H, m), 2.01-2.18 (3H, m), 2.43 (3H, s), 2.72-2.88 (2H, m), 3.14-2.18 (4H, m), 3.85 (2H, s), 4.64-4.66 (2H, t), 6.25 (2H, bs), 6.82 (1H, s), 7.48 (1H, s), 7.68-7.70 (1H, t); Mass (m/z): 408.2 $(M + H)^+$, 410.3 $(M + H)^+$. |

Example 60: Preparation of 5-Amino-6-chloro-N-{[3-(3-methoxy-2,2-dimethyl propyl)-3-azabicyclo [3.1.0]hex-6-yl]methyl}chroman-8-carboxamide

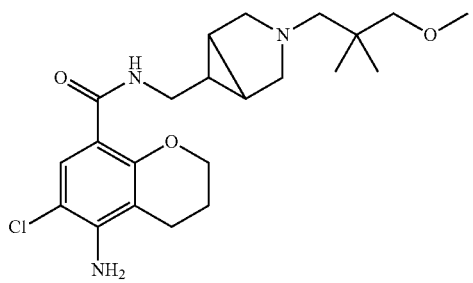 [SMILES: COCC(C)(C)CN1CC2C(CNC(=O)c3cc(Cl)c(N)c4c3OCCC4)C2C1]

A solution of 5-amino-6-chloro-N-{[3-azabicyclo[3.1.0]hex-6-yl]methyl}chroman-8-carboxamide (0.15 gram, 0.466 mmole, obtained in the preparation 8), 3-methoxy-2,2-dimethyl propyl toluene-4-sulfonate (0.25 grams, 0.919 mmole), cesium carbonate (0.30 grams, 0.920 mmole) and potassium iodide (0.15 grams, 0.903 mmole) in DMF (5 mL) was stirred for 24 hours at 120° C. The reaction mass was cooled to RT and quenched onto chilled water (10 mL). The product was extracted with EtOAc (3×5 mL), the organic extracts were washed with water (5 mL), brine solution (5 mL) and dried over sodium sulfate. The organic phase was concentrated on rotavacuum to obtain the crude residue, which was further purified by flash chromatography using TEA:MeOH:chloroform (CHCl$_3$) (0.5:2:97.5) to afford the title compound.

Weight: 0.011 grams (Yield: 5.59%).

$^1$H-NMR (δ ppm): 0.74 (6H, s), 1.22-1.28 (2H, m), 1.94-1.96 (2H, m), 2.20 (2H, s), 2.39-2.49 (3H, m), 2.71 (1H, s), 2.87-2.90 (3H, m), 2.96 (2H, s), 3.06-3.10 (2H, t), 3.32 (3H, s), 4.18-4.21 (2H, m), 5.59 (2H, s), 7.58 (1H, s), 7.97-8.00 (1H, t);

Mass (m/z): 422.3 (M+H)$^+$, 424.3 (M+H)$^+$.

Example 61: Preparation of 5-Amino-6-chloro-N-{[4-fluoro-1-(3-methoxy propyl)-4-piperidinyl] methyl}chroman-8-carboxamide

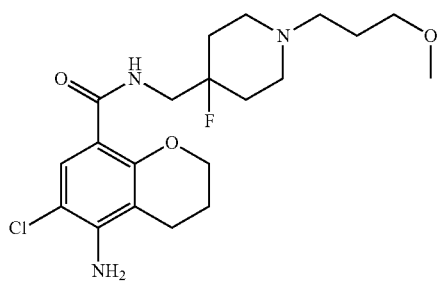 [SMILES: COCCCN1CCC(F)(CNC(=O)c2cc(Cl)c(N)c3c2OCCC3)CC1]

A solution of 5-amino-6-chloro-N-[(4-fluoro-4-piperidinyl)methyl]chroman-8-carboxamide (0.05 grams, 0.141 mmole, obtained in the preparation 9), 1-bromo-3-methoxypropane (0.03 grams, 196 mmole) and K$_2$CO$_3$ (0.065 grams, 0.471 mmole) in acetonitrile (5 mL) was stirred for 6 hours at 85° C., while monitoring the progress of the reaction by TLC. The reaction mass was quenched into chilled water (5 mL). The compound was extracted with EtOAc (3×5 mL), the extract was washed with water (5 mL), brine solution (5 mL) and dried over Na$_2$SO$_4$. The organic phase was concentrated on rotavacuum to obtain the crude residue, which was further purified by flash chromatography using TEA:MeOH:CHCl3 (0.5:2:97.5) to afford the title compound.

Weight: 0.03 gram (Yield: 55%).

$^1$H-NMR (δ ppm): 1.15-1.26 (7H, m), 1.58-1.63 (3H, m), 1.85-1.93 (4H, m), 2.25-2.27 (1H, m), 2.38-2.42 (2H, t), 2.58-2.69 (1H, m), 3.16-3.20 (2H, m), 3.29 (3H, s), 4.05-4.07 (2H, t), 5.72 (2H, bs), 7.12-7.23 (1H, t), 7.42 (1H, s);

Mass (m/z): 414.3 (M+H)$^+$, 416.3 (M+H)$^+$.

Example 62: Preparation of 4-Amino-5-chloro-N-{[3-(3-methoxypropyl)-3-azabicyclo [3.1.0]hex-6-yl] methyl}-2,3-dihydrobenzofuran-7-carboxamide oxalate

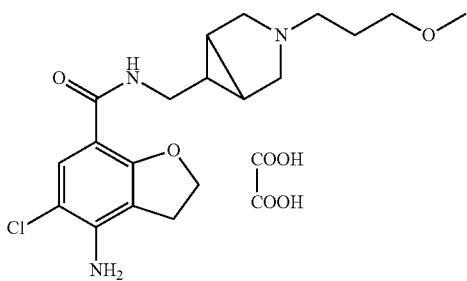 [SMILES: COCCCN1CC2C(CNC(=O)c3cc(Cl)c(N)c4c3OCC4)C2C1 ; O=C(O)C(=O)O]

Step (i): Preparation of 4-Amino-5-chloro-N-{[3-(3-methoxypropyl)-3-azabicyclo[3.1.0]hex-6-yl] methyl}-2,3-dihydrobenzofuran-7-carboxamide

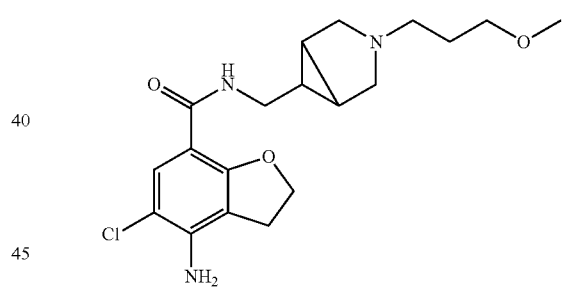

To a stirred solution of 4-amino-5-chloro-N-{[3-azabicyclo[3.1.0]hex-6-yl]methyl}-2,3-dihydrobenzofuran-7-carboxamide hydrochloride (80.0 mg, 0.23 mmole, obtained in the preparation 19) in dry DMF (1.0 mL) at RT, K$_2$CO$_3$ (80.0 mg, 0.58 mmole) followed by 1-bromo-3-methoxypropane (0.03 mL, 0.276 mmole) was added. The reaction mass was gradually heated to 80° C. and was stirred for 16 hours at this temperature. The reaction mass after cooling to RT was diluted with water and EtOAc. The two layers were separated; the organic layer was dried over anhydrous Na$_2$SO$_4$ and the solvent was removed under reduced pressure. The crude product obtained was purified by silica gel column chromatography to obtain the title compound.

Weight: 55.0 mg (Yield: 62%).

$^1$H-NMR (δ ppm): 1.35-1.45 (1H, m), 1.55-1.65 (4H, m), 1.70-1.81 (2H, m), 2.25-2.42 (2H, m), 2.45-2.60 (2H, m), 3.07 (2H, t, J=8.6 Hz), 3.28 (2H, t, J=6.0 Hz), 3.31 (3H, s), 3.38 (2H, t, J=6.2 Hz), 4.23 (2H, bs), 4.79 (2H, t, J=8.6 Hz), 7.38 (1H, bs), 7.86 (1H, s);

Mass (m/z): 380.1, 382.2 (M+H)$^+$.

Step (ii): Preparation of 4-Amino-5-chloro-N-{[3-(3-methoxypropyl)-3-azabicyclo[3.1.0]hex-6-yl]methyl}-2,3-dihydrobenzofuran-7-carboxamide oxalate To a stirred solution of 4-amino-5-chloro-N-{[3-(3-methoxypropyl)-3-azabicyclo [3.1.0]hex-6-yl]methyl}-2,3-dihydrobenzofuran-7-carboxamide (55.0 mg, 0.144 mmole, obtained in the above step) in isopropanol (2.0 mL) at RT, oxalic acid (12.0 mg, 0.144 mmole) was added. The reaction mass was stirred for 16 hours before the volatiles were removed under reduced pressure. The crude mass was triturated with ether to obtain the title compound.

Weight: 53.5 mg (Yield: 78%).
$^1$H-NMR (δ ppm): 1.30-1.45 (1H, m), 1.65-1.86 (4H, m), 2.95-3.10 (4H, m), 3.15-3.20 (2H, m), 3.19 (3H, s), 3.25-3.40 (2H, m), 3.50-3.70 (2H, m), 4.70 (2H, t, J=8.4 Hz), 5.89 (2H, bs), 7.45 (1H, s), 7.58 (1H, bs);
Mass (m/z): 380.2, 382.3 (M+H)$^+$.

Examples 63 to 65

The compounds of Examples 63 to 65 were prepared by following the experimental procedure as described in the Example 61 to 62 given above, with some noncritical variations.

| Example Number | Chemical name and Structure | Characterization data |
|---|---|---|
| 63. | 4-Amino-5-chloro-N-{[3-(3-methoxypropyl)-3-azabicyclo[3.1.0]hex-6-yl]methyl}benzofuran-7-carboxamide hydrochloride 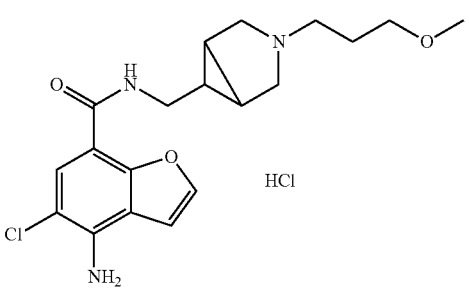 [SMILES: COCCCN1CC2C(CNC(=O)c3cc(Cl)c(N)c4ccoc34)C2C1 ; Cl] | $^1$H-NMR (δ ppm): 1.55-1.61 (1H, m), 1.78-1.86 (4H, m), 1.91-1.97 (2H, m), 3.04-3.10 (6H, m), 3.21 (3H, s), 3.57-3.61 (2H, m), 6.48 (2H, bs), 7.28 (1H, d, J = 1.82 Hz), 7.61 (1H, s), 7.92-7.93 (1H, d, J = 1.74 Hz), 7.97-8.00 (1H, t), 9.85 (1H, bs); Mass (m/z): 378.1 (M + H)$^+$, 380.1 (M + H)$^+$. |
| 64. | 4-Amino-5-chloro-2-methyl-N-{[3-(3-methoxypropyl)-3-azabicyclo[3.1.0]hex-6-yl]methyl}benzofuran-7-carboxamide hydrochloride 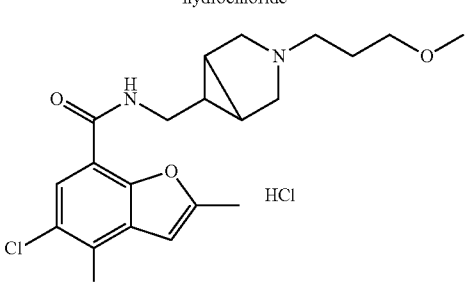 | $^1$H-NMR (δ ppm): 1.56-1.57 (1H, m), 1.78-1.88 (4H, m), 2.46 (3H, s), 3.07-3.11 (2H, m), 3.21 (3H, s), 3.22-3.28 (4H, m), 3.32-3.35 (2H, m), 3.57-3.61 (2H, m), 6.30 (2H, bs), 6.85 (1H, s), 7.51 (1H, s), 7.91-7.94 (1H, t), 9.87 (1H, bs); Mass (m/z): 392.2 (M + H)$^+$, 394.1 (M + H)$^+$. |
| 65. | 4-Amino-5-bromo-N-{[3-(3-methoxypropyl)-3-azabicyclo[3.1.0]hex-6-yl]methyl}-2,3-dihydrobenzofuran-7-carboxamide oxalate 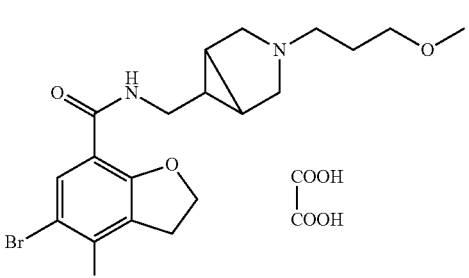 | $^1$H-NMR (δ ppm): 1.28-1.38 (1H, m), 1.50-1.62 (2H, m), 1.62-1.75 (2H, m), 2.70-2.90 (4H, m), 3.03 (2H, t, J = 8.7 Hz), 3.11 (2H, t, J = 6.1 Hz), 3.18 (3H, s), 3.20-3.29 (2H, m), 3.29 (2H, t, J = 6.0 Hz), 4.70 (2H, t, J = 8.7 Hz), 5.81 (2H, bs), 7.54 (1H, bs), 7.61 (1H, s); Mass (m/z): 424.0 (M + H)$^+$, 426.0 (M + H)$^+$. |

Example 66: Preparation of 5-Amino-6-chloro-N-{[1-(2-fluoroethyl)-4-piperidinyl]methyl}chroman-8-carboxamide

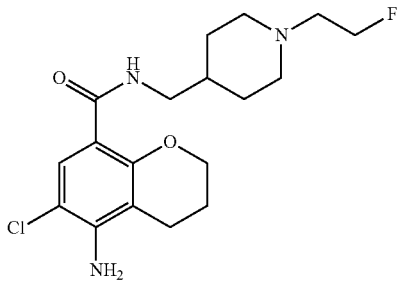 [SMILES: Nc1c(Cl)cc(C(=O)NCC2CCN(CCF)CC2)c2c1CCCO2]

Step (i): Preparation of 5-Amino-6-chloro-N-{[1-(2-hydroxy ethyl)-4-piperidinyl]methyl}chroman-8-carboxamide

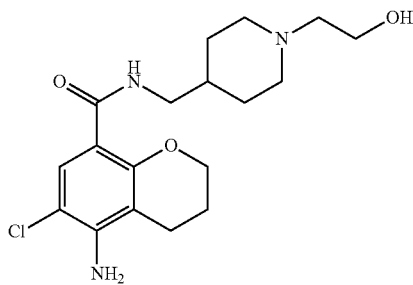 [SMILES: Nc1c(Cl)cc(C(=O)NCC2CCN(CCO)CC2)c2c1CCCO2]

A solution of 5-amino-6-chloro-N-(4-piperidinylmethyl)chroman-8-carboxamide (0.1 grams, 0.313 mmole, obtained in the preparation 7), bromoethanol (0.047 grams, 0.376 mmole) and potassium carbonate (0.086 grams, 0.623 mmole) in acetonitrile (15 mL) was stirred overnight at 85° C. After completion of the reaction (TLC), the reaction mass was concentrated, the slurry obtained was quenched in water (30 mL) and the compound was extracted with DCM (3×15 mL). The combined organic phase was washed with water (15 mL), brine solution (15 mL) and dried over $Na_2SO_4$. The organic phase was concentrated under vacuum to obtain the crude residue, which was further purified by flash chromatography using TEA:MeOH:$CHCl_3$ (1:3:96) to afford the title compound.

Weight: 0.07 grams (Yield: 62%).

$^1$H-NMR (δ ppm): 1.52-1.58 (2H, m), 1.88-1.96 (4H, m), 2.06-2.11 (2H, m), 2.54-2.57 (2H, t), 2.71-2.86 (3H, m), 3.08-3.18 (2H, m), 3.47-3.50 (2H, m), 3.82-3.84 (2H, t), 4.26-4.29 (2H, t), 7.72 (1H, s);

Mass (m/z): 368.3 (M+H)$^+$, 370.3 (M+H)$^+$.

Step (ii): Preparation of 5-Amino-6-chloro-N-{[1-(2-fluoro ethyl)-4-piperidinyl]methyl}chroman-8-carboxamide DAST (0.072 grams, 0.448 mmole) was added to a stirred solution of 5-amino-6-chloro-N-{[1-(2-hydroxyethyl)-4-piperidinyl]methyl}chroman-8-carboxamide (0.07 grams, 0.179 mmole, obtained in the above step) in DCM (5 mL) at −30° C. The reaction mass temperature was slowly raised to RT and stirred overnight at same temperature. The reaction mass was quenched in chilled water (10 mL). The pH was adjusted to ~9.5 using aqueous $NH_3$ and the compound was extracted with DCM (3×5 mL). The combined organic phase was washed with water (5 mL), brine solution (5 mL) and dried over $Na_2SO_4$. The organic phase was concentrated on rotavacuum to obtain the crude residue, which was further purified by flash chromatography using TEA:MeOH:$CHCl_3$ (0.5:2:97.5) to afford the title compound.

Weight: 0.014 grams (Yield: 20%).

$^1$H-NMR (δ ppm): 2.04-2.15 (3H, m), 2.51-2.54 (2H, t), 2.71-2.78 (2H, m), 3.02-3.05 (2H, m), 3.31-3.34 (2H, t), 3.64-3.72 (4H, m), 4.25-4.28 (4H, m), 4.54-4.56 (1H, t), 4.66-4.68 (1H, t), 7.87-7.91 (1H, t), 8.02 (1H, s);

Mass (m/z): 370.3 (M+H)$^+$, 372.3 (M+H)$^+$.

Biological Assays

Example 67: Determination of $EC_{50}$ Values for 5-$HT_4$ Receptor

A stable CHO cell line expressing recombinant human 5-$HT_4$ receptor and pCRE-Luc reporter system was used for cell-based assay. The assay offers a non-radioactive based approach to determine binding of a compound to GPCRs. In this specific assay, the level of intracellular cyclic AMP, which is modulated by activation, or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compounds were added in OptiMEM medium to the cells. The incubation was continued at 37° C. in $CO_2$ incubator for 4 hours. Medium was removed and cells were washed with phosphate buffered saline. The cells were lysed and luciferase activity was measured in a Luminometer. Luminescence units were plotted against the compound concentrations using Graphpad software. $EC_{50}$ values of the compounds were defined as the concentration required in stimulating the luciferase activity by 50%.

Using this protocol, compounds described herein were found to exhibit binding affinity towards 5-$HT_4$ receptor. For instance, examples 1, 3, 4, 8, 9, 36, 40, 46, 52, 55, 58, 59, and 60 as described herein, exhibited 5-$HT_4$ receptor agonistic binding in-vitro $EC_{50}$ values of less than or equal to 1 nM; examples 6, 10, 12, 18, 22, 26, 30, 35, 37, 43, 44, 49, 60, 62, 64 and 66 as described herein, exhibited 5-$HT_4$ receptor agonistic binding in-vitro $EC_{50}$ values between 1.1 nM to 5 nM; examples 13, 17, 20, 24, 28, 32, 38, 39, 42, 50, 54, 57 and 63 as described herein, exhibited 5-$HT_4$ receptor agonistic binding in-vitro $EC_{50}$ values between 5.1 nM to 10 nM; examples 7, 15, 29, 41, 51, 53 and 65 as described herein, exhibited 5-$HT_4$ receptor agonistic binding in-vitro $EC_{50}$ values between 10.1 nM to 20 nM.

Example 68: Rodent Pharmacokinetic Study

Male wistar rats (225±25 grams) were used as experimental animals. Three to five animals were housed in each cage. Two days prior to dosing day, male wistar rats (225-250 grams) were anesthetized with isoflurane for surgical placement of jugular vein catheter. Animals were fasted overnight before oral dosing (p.o) and food pellets were allowed 2 hours post dosing, whereas during intravenous dosing food and water were provided as ad libitum. Three rats were dosed with test compounds (3 mg/kg) orally and intravenously (1 mg/kg).

At each time point blood was collected through jugular vein and immediately replenish with an equivalent volume of normal saline from freely moving rats. Collected blood was transferred into a labeled eppendr off containing 10 μL of heparin as anticoagulant. Typically blood samples were collected as following time points: Pre dose, 0.08 (only i.v.), 0.25, 0.5, 1, 2, 4, 6, 8, and 24 hours post dose-(n=3). Blood was centrifuged at 4000 rpm for 10 minutes. Plasma was prepared and stored frozen at −20° C. until analysis. The concentrations of the test compounds were quantified in plasma by qualified LC-MS/MS method using suitable extraction technique. The test compounds were quantified in the calibration range around 2-2000 ng/mL in plasma. Study samples were analyzed using calibration samples in the batch and quality control samples spread across the batch.

Pharmacokinetic parameters $C_{max}$, $T_{max}$, $AUC_t$, $T_{1/2}$ and Bioavailability were calculated by non-compartmental model using standard non-compartmental model by using WinNonLin 5.0.1 or Phoenix WinNonlin 6.2 version Software package.

flurane anesthesia. The animals were sacrificed to collect brain tissue. Plasma was separated and brain samples were homogenized and stored frozen at −20° C. until analysis. The concentrations of the test compounds in plasma and brain were determined using LC-MS/MS method.

The test compounds were quantified in plasma and brain homogenate by qualified LC-MS/MS method using suitable extraction technique. The test compounds were quantified in the calibration range of 1-500 ng/mL in plasma and brain homogenate. Study samples were analyzed using calibration samples in the batch and quality control samples spread across the batch. Extent of brain-plasma ratio was calculated ($C_b/C_p$).

| Example Number | Dose (mg/kg) | Vehicle | Route of administration | Single dose Brain Penetration ($C_b/C_p$) |
|---|---|---|---|---|
| 3. | 3 | Reagent grade Water | oral (gavage) | 1.03 ± 0.02 |
|  | 1 | Water for injection | intravenous (bolus) |  |

| Example Number | Dose (mg/kg) | Vehicle | Route of administration | $C_{max}$ (ng/mL) | $T_{max}$ (h) | $AUC_{0-t}$ (ng · hr/mL) | $T_{1/2}$ (h) | Bio-availability (%) |
|---|---|---|---|---|---|---|---|---|
| 3. | 3 | Reagent grade Water | oral (gavage) | 131 ± 35 | 0.42 ± 0.14 | 324 ± 105 | 1.6 ± 0.1 | 68 ± 22 |
|  | 1 | Water for injection | intravenous (bolus) | — | — | 158 ± 7 | 1.9 ± 0.6 |  |
| 44. | 3 | Reagent grade Water | oral (gavage) | 110 ± 25 | 0.33 ± 0.14 | 176 ± 10 | 1.3 ± 0.3 | 25 ± 1 |
|  | 1 | Water for injection | intravenous (bolus) | — | — | 232 ± 14 | 1.5 ± 0.6 |  |
| 48. | 3 | Reagent grade Water | oral (gavage) | 167 ± 20 | 0.31 ± 0.13 | 224 ± 33 | 1.0 ± 0.1 | 35 ± 5 |
|  | 1 | Water for injection | intravenous (bolus) | — | — | 211 ± 41 | 1.5 ± 0.4 |  |
| 50. | 3 | Reagent grade Water | oral (gavage) | 230 ± 56 | 0.25 ± 0.00 | 346 ± 71 | 1.5 ± 0.2 | 63 ± 13 |
|  | 1 | Water for injection | intravenous (bolus) | — | — | 182 ± 37 | 1.2 ± 0.3 |  |
| 53. | 3 | Reagent grade Water | oral (gavage) | 182 ± 26 | 0.33 ± 0.14 | 250 ± 87 | 1.6 ± 0.6 | 27 ± 20 |
|  | 1 | Water for injection | intravenous (bolus) | — | — | 147 ± 17 | 0.8 ± 0.1 |  |

Example 69: Rodent Brain Penetration Study

Male Wistar rats (225±25 grams) were used as experimental animals. Three animals were housed in each cage. Animals were given water and food ad libitum throughout the experiment and maintained on a 12 hours light/dark cycle.

Brain penetration was determined in discrete manner in rats. One day prior to dosing day, male wistar rats (225-250 grams) were acclimatized. After acclimatization the rats were grouped according to their weight. In each group, 3 animals were kept in individual cage and allowed free access to food and water. At each time point (0.50, 1 and 2 hours) n=3 animals were used.

The test compounds were suitably preformulated and administered orally at (free base equivalent) 3 mg/kg. Blood samples were removed via, cardiac puncture by using iso- -continued

| Example Number | Dose (mg/kg) | Vehicle | Route of administration | Single dose Brain Penetration ($C_b/C_p$) |
|---|---|---|---|---|
| 44. | 3 | Reagent grade Water | oral (gavage) | 0.78 ± 0.06 |
|  | 1 | Water for injection | intravenous (bolus) |  |
| 48. | 3 | Reagent grade Water | oral (gavage) | 1.00 ± 0.16 |
|  | 1 | Water for injection | intravenous (bolus) |  |

-continued

| Example Number | Dose (mg/kg) | Vehicle | Route of administration | Single dose Brain Penetration ($C_b/C_p$) |
|---|---|---|---|---|
| 50. | 3 | Reagent grade Water | oral (gavage) | 1.48 ± 0.26 |
|  | 1 | Water for injection | intravenous (bolus) |  |
| 53. | 3 | Reagent grade Water | oral (gavage) | 2.53 ± 0.63 |
|  | 1 | Water for injection | intravenous (bolus) |  |

Example 70: Estimation of Mice Brain Cortical sAPPα Levels

Experimental Procedure

Male C57BL/6J mice (20-30 grams) were randomly divided (n=7/group) into different treatment groups. Control group of mice were subcutaneously (s.c.) administered with sterile water for injection. Mice from treatment groups received a single s.c. injection of test compound (dose volume of 10 mL/kg) or prucalopride (10 mg/kg) dissolved in sterile water for injection. Mice were sacrificed by cervical dislocation at 60 minutes or 90 minutes after administration of test compound, Example 50 or prucalopride, respectively. Brains were quickly isolated and the cortex was dissected at –20° C. The cortex was immediately kept on a dry ice and weighed before being stored at –80° C. until quantification of sAPPα using Enzyme-linked immunosorbent assay (ELISA).

Sample Preparation:
1. Cortical tissues were thawed and Tris Buffer Saline (TBS) containing protease inhibitors was added in a proportion of 0.8 mL for each 200 mg of tissue.
2. Obtained samples were homogenized using glass-Teflon homogenizer at 10 strokes. The resulting homogenates were centrifuged at 15,000 rpm at 4° C. for 90 minutes.
3. The supernatant was discarded and to the precipitate, 4 times volume (0.8 mL/200 mg tissues) of TBS was added. Again homogenized followed by centrifugation at 15,000 rpm at 4° C. for 30 minutes.
4. From the above centrifuged mixture the supernatant was discarded and 10 times volume of 6M Guanidine-HCl in 50 mM Tris buffer pH: 7.6 (500 µL/50 mg tissues) was added. The resulting solution was sonicated for 5 seconds, 4 times.
5. Resulting mixture was incubated at the room temperature for 30 minutes, followed by centrifugation at 15,000 rpm, 4° C. for 30 minutes. From this 5 µL of supernatant solution was taken and diluted with 155 µL of EIA buffer (dilution factor 32).

Measurement of sAPPα by ELISA Kit:
To investigate the role of an acute treatment of test compound on sAPPα levels, the expression of this protein was measured in homogenates obtained from the cortex of treated and untreated mice employing ELISA assay. The entire procedure was followed as described in the ELISA kit manual (Mouse/Rat sAPPα ELISA, Catalog Number: JP27415, Innovation Beyond Limits International, Hamburg, Germany).

Statistical Analysis:
Statistical analyses were performed using the Graph Pad Prism (Version 4). Data are Mean±SD of sAPPα levels expressed as percentage of control values (mice which received water for injection). Values were compared between the different groups by using unpaired test. The significance level was set at *p<0.05; p<0.01; *p<0.001.

REFERENCES

Journal of Pharmacology and Experimental Therapeutics, 2003, 305, 864-871; Current Pharmaceutical Design 2006, 12, 671-676; and Journal of Pharmacology and Experimental Therapeutics 2006, 317, 786-790.

Result of the Test Compound (FIG. 1):
At 60 minutes post treatment, the test compound produced significant increase in the mice brain cortical sAPPα levels i.e. increase of 44% was observed when tested at doses 1 mg/kg, s.c. dose (FIG. 1). The positive control, 5-HT$_4$ receptor agonist, prucalopride significantly increased the level of sAPPα in adult mice cortex at 10.0 mg/kg s.c. These results are in line with results of reported literature (British Journal of Pharmacology, 2007, 150, 883-892).

Example 71: To Evaluate the Effect of Compounds of Present Invention on Modulation of Acetylcholine from the Ventral Hippocampus of Male Wistar Rats Experimental Procedure:
Male Wistar rats (240-300 grams) were stereotaxically implanted with a microdialysis guide cannula in ventral hippocampus (AP: –5.2 mm, ML: +5.0 mm, DV: –3.8 mm). Co-ordinates were taken according to Paxinos and Watson (2004) with reference points taken from bregma and vertical from the skull. The rats were allowed to recover individually for four to five days in a round bottom Plexiglas bowl with free access to feed and water.

One day prior to the microdialysis experiment, rats were connected to a dual quartz lined two-channel liquid swivel (Instech, UK) on a counter balance lever arm, which allowed unrestricted movements of the animal. Sixteen hour before start of study, a pre-equilibrated microdialysis probe (4 mm dialysis membrane) was inserted into the ventral hippocampus through the guide cannula.

On the day of study, probe was perfused at a constant flow rate of 1.5 µL/minutes with artificial cerebrospinal fluid (aCSF; NaCl 147 mM, KCl 3.0 mM, MgCl$_2$ 1.0 mM, CaCl$_2$.2H$_2$O 1.3 mM, NaH$_2$PO4.2H$_2$O 0.2 mM and Na$_2$HPO$_4$.7H$_2$O 1.0 mM, pH 7.2). A stabilization period of 2 h was maintained and five basal samples were collected at 20 minutes intervals. Test compound, Example 50 or vehicle was administered and dialysate samples were collected at 20 minutes interval for an additional period of 4 hours. Dialysates were stored below –70° C. until quantitation of acetylcholine.

Quantitation of Acetylcholine:
Acetylcholine in dialysate was quantified in the calibration range of 0.103 nmol-103.491 nmol using LC-MS/MS method.

Statistical Analysis:
All microdialysis data were plotted as percent change from mean dialysate basal concentrations with 100% defined as the average of five pre-dose values. The AUC was calculated by trapezoidal rule using WinNonlin (5.0.1 version, Pharsight Corp. CA). The statistical significance between the mean AUC values of treatment groups with vehicle was calculated using one-way ANOVA followed by Dunnett's test. For each treatment group, the percent increase in acetylcholine levels was compared to the vehicle group using two-way analysis of variance (time and treatment), followed by Bonferroni's multiple comparison test. Statistical significance was considered at a p value less than 0.05.

In-correct probe placement was considered as criteria to reject the data from animal.

REFERENCE

Figure 2:
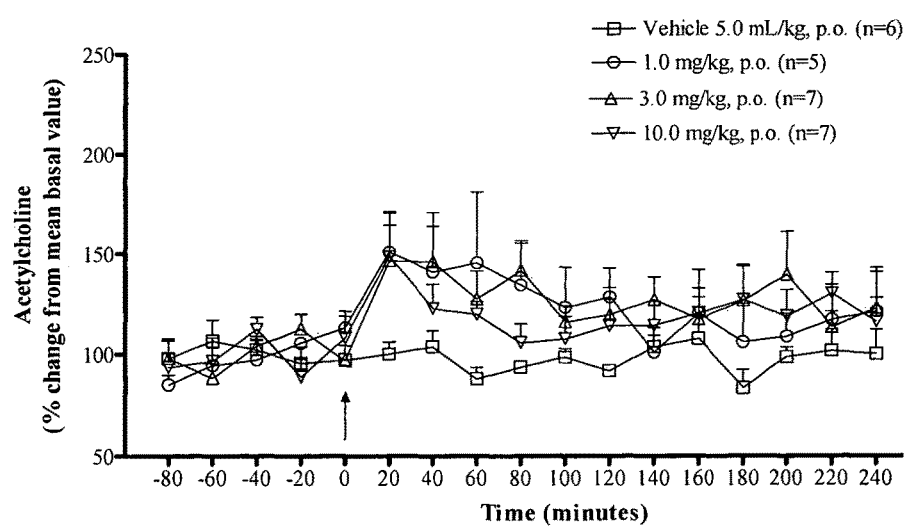
FIG. 2: Effect of test compound on modulation of acetylcholine from the ventral hippocampus of male Wistar rats
Figure 3:
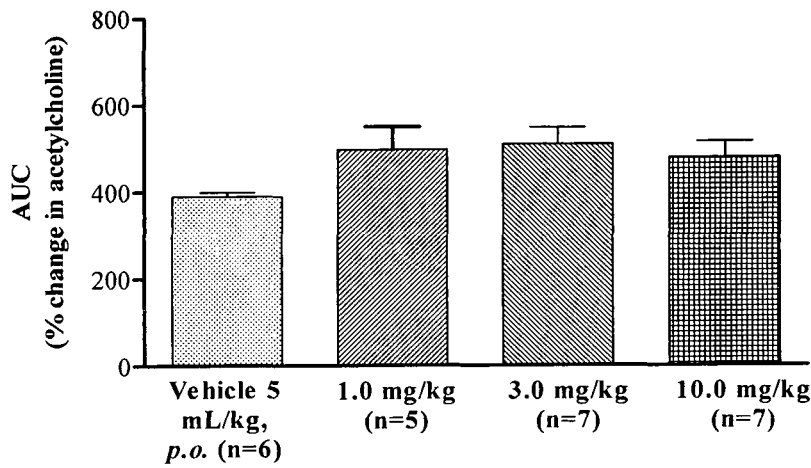
FIG. 3: Evaluation of the effect of test compound on modulation of acetylcholine from the ventral hippocampus of male Wistar rats

Neuropharmacology, 2007, 53, 563-573.
Results for the Test Compound:

The test compound (1.0 mg/kg, p.o.) produced 51% increase in acetylcholine levels from ventral hippocampus of male Wistar rats (FIG. 2). Treatment with 3.0 and 10.0 mg/kg, p.o. of test compound produced similar magnitude of increase in hippocampal acetylcholine levels. Area under the curve values calculated to evaluate the overall effect of treatment showed 31% increase after treatment with test compound (1.0 mg/kg, p.o.) (FIG. 3).

Example 72: To Evaluate the Effect of Compounds of Present Invention on Modulation of Acetylcholine from the Frontal Cortex of Male Wistar Rats Experimental Procedure:

Male Wistar rats (240-300 grams) were stereotaxically implanted with a microdialysis guide cannula in frontal cortex (AP: +3.2 mm, ML: −3.2 mm, DV: −1.5 mm). Co-ordinates were taken according to Paxinos and Watson (2004) with reference points taken from bregma and vertical from the skull. The rats were allowed to recover individually for four to five days in a round bottom Plexiglas bowl with free access to feed and water.

One day prior to the microdialysis experiment, rats were connected to a dual quartz lined two-channel liquid swivel (Instech, UK) on a counter balance lever arm, which allowed unrestricted movements of the animal. Sixteen hour before start of study, a pre-equilibrated microdialysis probe (3 mm dialysis membrane) was inserted into the frontal cortex through the guide cannula.

On the day of study, probe was perfused at a constant flow rate of 1.5 µL/minutes with artificial cerebrospinal fluid (aCSF; NaCl 147 mM, KCl 3.0 mM, $MgCl_2$ 1.0 mM, $CaCl_2$.$2H_2O$ 1.3 mM, $NaH_2PO4.2H_2O$ 0.2 mM and $Na_2HPO_4.7H_2O$ 1.0 mM, pH 7.2). A stabilization period of 2 hours was maintained and five basal samples were collected at 20 minutes intervals. The test compound, Example 50 or vehicle was administered and dialysate samples were collected at 20 minutes interval for an additional period of 4 hours. Dialysates were stored below −70° C. until quantitation of acetylcholine.

Quantitation of Acetylcholine:

Acetylcholine in dialysate was quantified in the calibration range of 0.103 nmol-103.491 nmol using LC-MS/MS method.

Statistical Analysis:

All microdialysis data were plotted as percent change from mean dialysate basal concentrations with 100% defined as the average of five pre-dose values. The AUC was calculated by trapezoidal rule using WinNonlin (5.0.1 version, Pharsight Corp. CA). The statistical significance between the mean AUC values of treatment groups with vehicle was calculated using one-way ANOVA followed by Dunnett's test. For each treatment group, the percent increase in acetylcholine levels was compared to the vehicle group using two-way analysis of variance (time and treatment), followed by Bonferroni's multiple comparison test. Statistical significance was considered at a p value less than 0.05.

In-correct probe placement was considered as criteria to reject the data from animal.

REFERENCE

Current Drug Targets—CNS & Neurological Disorders, 2004, 3, 39-51.

Figure 4:
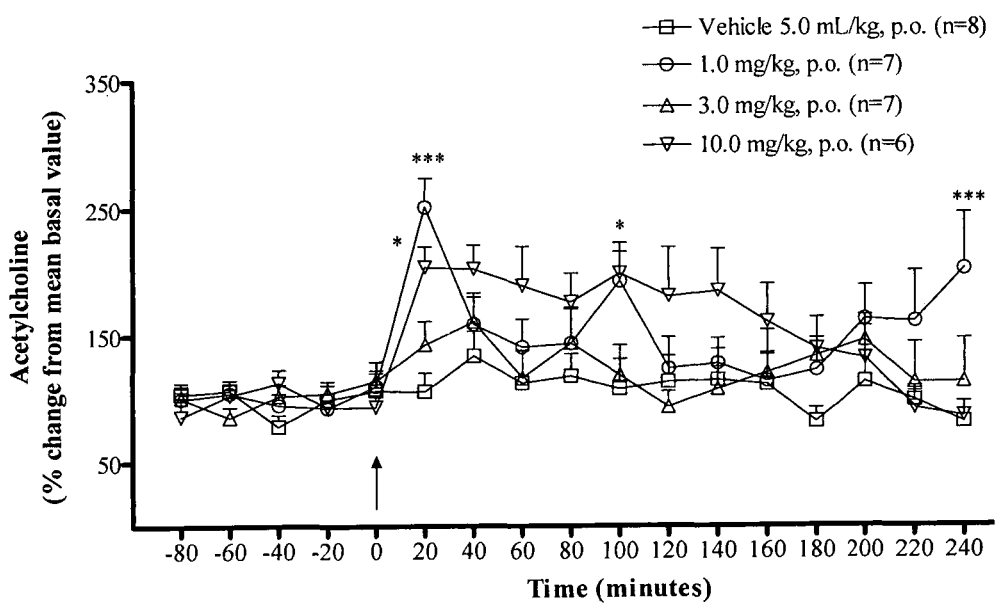
FIG. 4: Effect of test compound on modulation of acetylcholine from the frontal cortex of male Wistar rats
Figure 5:
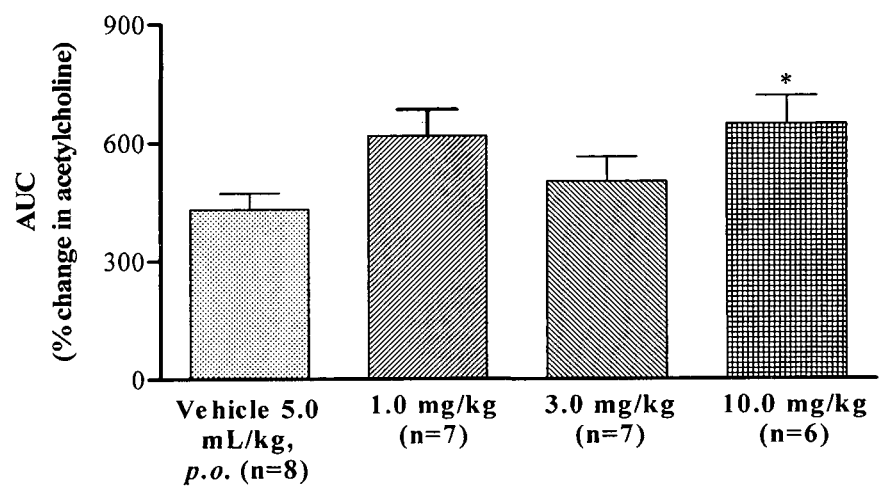
FIG. 5: Evaluation of the effect of test compound on modulation of acetylcholine from the ventral hippocampus of male Wistar rats

Result of the Test Compound:

The test compound produced dose-dependent increase in acetylcholine levels of frontal cortex in male Wistar rats (FIG. 4). Acetylcholine levels reached to the extent of 204% of pre-dose levels at 10.0 mg/kg, p.o. Area under the curve (AUC) values calculated to evaluate the overall effect of treatment showed significant increase in AUC after treatment with test compound at 10.0 mg/kg, p.o. (FIG. 5).

Example 73: Object Recognition Task Model

The cognition enhancing properties of compounds of this invention were estimated by using this model.

Male Wistar rats (230-280 grams) were used as experimental animals. Four animals were housed in each cage. Animals were kept on 20% food deprivation before one day and given water ad libitum throughout the experiment and maintained on a 12 hours light/dark cycle. Also the rats were habituated to individual arenas for 1 hour in the absence of any objects.

One group of 12 rats received vehicle (1 mL/Kg) orally and another set of animals received compound of the formula (I) either orally or i.p., before one hour of the familiar (T1) and choice trial (T2).

The experiment was carried out in a 50×50×50 cm open field made up of acrylic. In the familiarization phase, (T1), the rats were placed individually in the open field for 3 minutes, in which two identical objects (plastic bottles, 12.5 cm height×5.5 cm diameter) covered in yellow masking tape alone (a1 and a2) were positioned in two adjacent corners, 10 cms from the walls. After 24 hours of the (T1) trial for long-term memory test, the same rats were placed in the same arena as they were placed in T1 trial. Choice phase (T2) rats were allowed to explore the open field for 3 minutes in presence of one familiar object (a3) and one novel object (b) (Amber color glass bottle, 12 cm high and 5 cm in diameter). Familiar objects presented similar textures, colors and sizes. During the T1 and T2 trial, explorations of each object (defined as sniffing, licking, chewing or having moving vibrissae whilst directing the nose towards the object at a distance of less than 1 cm) were recorded separately by stopwatch. Sitting on an object was not regarded as exploratory activity, however, it was rarely observed.

T1 is the total time spent exploring the familiar objects (a1+a2).

T2 is the total time spent exploring the familiar object and novel object (a3+b).

The object recognition test was performed as described by Behaviour Brain Research, 31 (1988), 47-59.

| Example Number | Dose | Exploration time mean ± S.E.M (sec) | | Inference |
|---|---|---|---|---|
| | | Familiar object | Novel object | |
| 3. | 0.003 mg/kg, p.o. | 9.9 ± 2.06 | 17.58 ± 2.24 | Active |
| 44. | 3 mg/kg, p.o. | 5.44 ± 1.02 | 14.64 ± 2.19 | Active |
| 48. | 3 mg/kg, p.o. | 7.02 ± 0.76 | 13.80 ± 1.74 | Active |
| 50. | 0.1 mg/kg, p.o. | 9.89 ± 1.49 | 18.58 ± 2.44 | Active |
| 53. | 0.3 mg/kg, p.o. | 8.24 ± 1.32 | 15.98 ± 1.75 | Active |

Example 74: Radial Arm Maze

The cognition enhancing properties of test compounds of this invention were estimated by using this model.

Radial arm maze consists of a central hub of 45 cm diameter. Each arm was of dimension 42.5×15×24 cm. The maze was elevated to a height of 1 m above the ground. The animals were placed on a restricted diet until they reached approximately 85% of their free feeding weight. During this diet restriction period animals were habituated to the novel feed (pellets). Once the rats reached approximately 85% of their free feeding weight, rats were habituated to the maze on the $1^{st}$ and $2^{nd}$ day. The animals that did not eat the pellets were rejected from the study. Animals were randomized on day 2. On the subsequent days the treatment was given as per the allotment. Each animal was introduced into the maze individually for a period of 10 minutes. The arms were baited only once and the animal had to learn the rule that repeated arm entries would not be rewarded. The trial ended once the rat had visited 16 arms or 10 minutes were over or all the pellets were eaten. The arm entries were recorded using the software. Once the trial was over the rat was removed and the maze was cleaned using soap water.

| Example Number | Reversal of Scopolamine Induced amnesia - Effective dose range |
|---|---|
| 3. | 0.03 mg/kg, p.o. |
| 50. | 1 mg/kg, p.o. |

Example 75: Automated hERG Patch Clamp Assay

To study the cardiac safety of test compounds using automated hERG patch clamp assay, hERG-HEK293 cells were grown to 70% confluency and were harvested using accumax. The cells were then suspended in complete media and were incubated at 37° C. and 5% $CO_2$ for 30 minutes before using these cells for the whole cell patch clamp assay. Whole cell patch clamp recordings were conducted on Nanion's Patchliner using I-V protocol of voltage step from holding potential of −80 mV to +40 mV for 500 ms and then to test potential for 500 ms and back to holding potential of −80 mV. Pulses were elicited every 10 seconds. Each test compound concentration was incubated for 5 minutes. Data analysis was done by plotting the raw data using Igor Pro software and $IC_{50}$ values were calculated. Cells with resistance >1 Gohms and tail currents of >200 pA were taken into consideration for data analysis. Quinidine was used as positive control.

| Example number | hERG ($IC_{50}$) |
|---|---|
| 37 | >10 μM |
| 44 | >10 μM |
| 50 | >10 μM |
| 53 | >10 μM |

We claim:
1. A compound of the general formula (I),

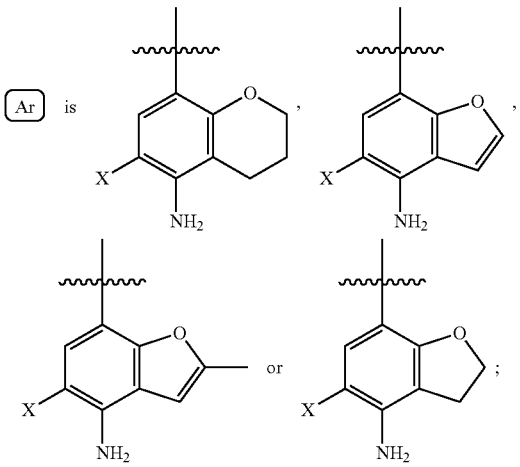

or a stereoisomer, a pharmaceutically acceptable salt thereof,
wherein,

Ar is

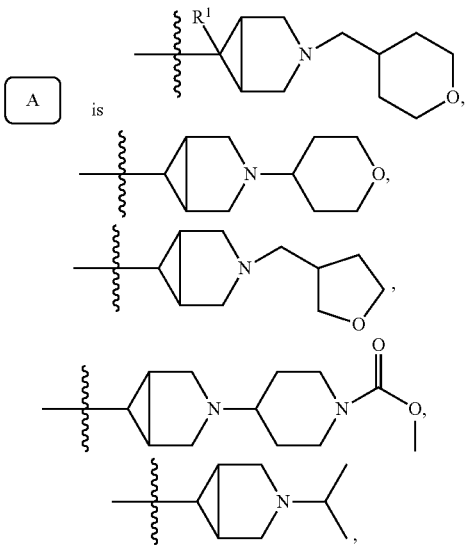

X is halogen or hydrogen;

A is

-continued

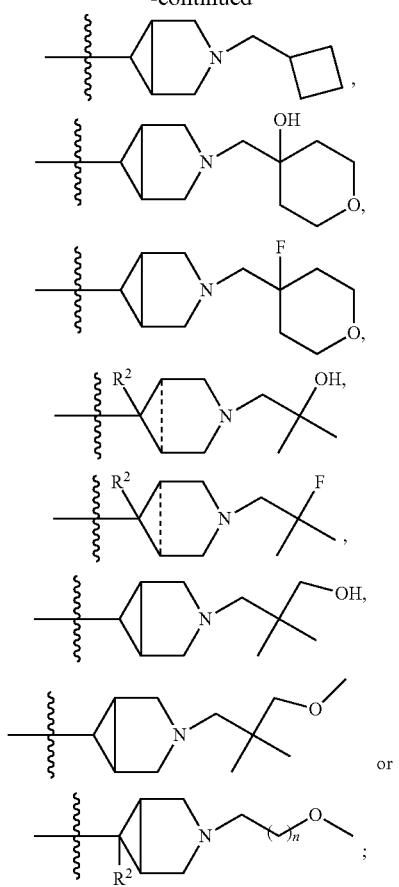

"∿∿∿" is point of attachment;
"--------" is bond or no bond;
$R_1$ is hydrogen, fluorine or hydroxyl;
$R_2$ is hydrogen or fluorine; provided that $R_2$ is fluorine when "--------" is no bond; and
"n" is 1 or 2.

2. The compound according to claim 1, wherein:

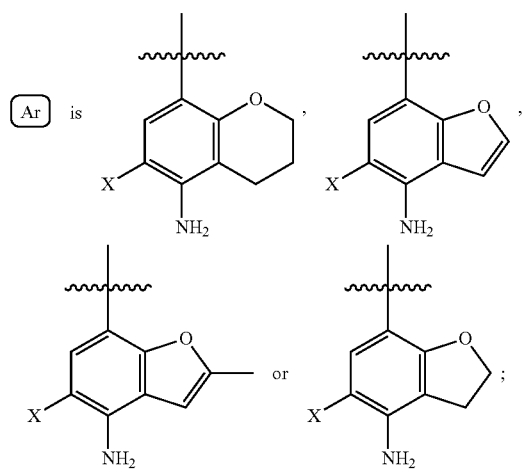

X is chlorine, bromine or hydrogen;

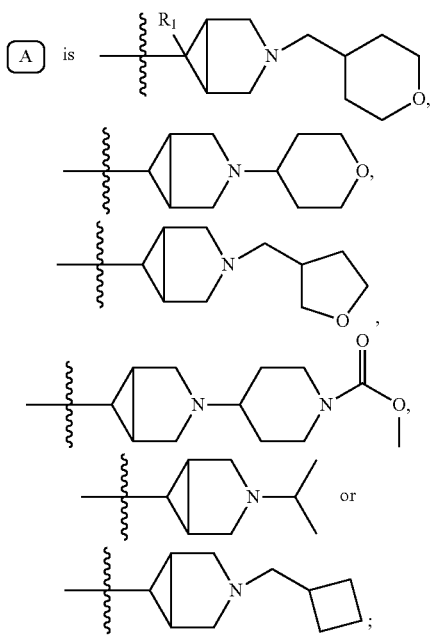

"∿∿∿" is point of attachment; and
$R_1$ is hydrogen.

3. The compound according to claim 1, wherein the compound is selected from,
(a) a compound of formula (Ib-1):

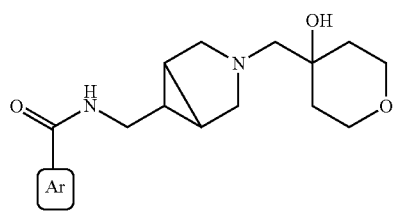

or a stereoisomer, a pharmaceutically acceptable salt thereof,
wherein,

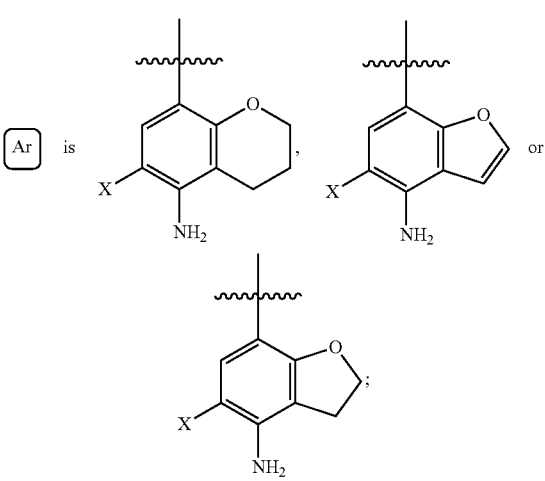

"∿∿∿" is point of attachment;
X is chlorine;

(b) a compound of formula (Ib-2):

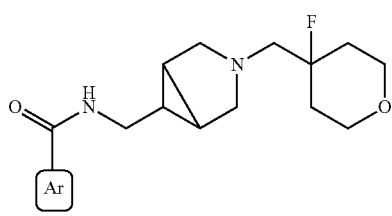

(Ib-2)

or a stereoisomer, a pharmaceutically acceptable salt thereof,
wherein,

Ar is

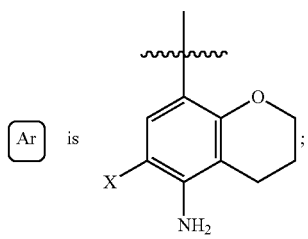

X is chlorine;
"⸺" is point of attachment;
(c) a compound of formula (Id-1):

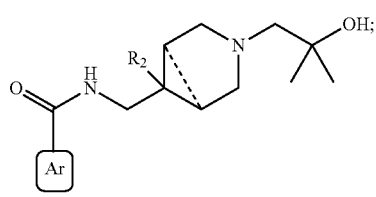

(Id-1)

or a stereoisomer, a pharmaceutically acceptable salt thereof,
wherein,
"--------" is a bond or no bond;

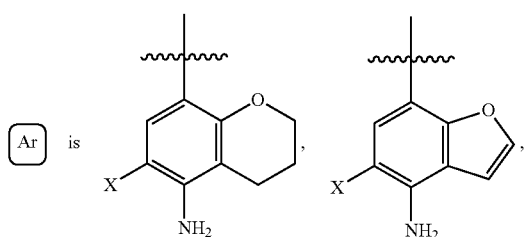

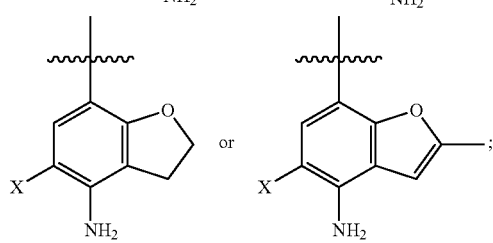

X is chlorine or bromine;
"⸺" is point of attachment;
$R_2$ is hydrogen or fluorine; provided that $R_2$ is fluorine when "--------" is no bond;
(d) a compound of formula (Id-2):

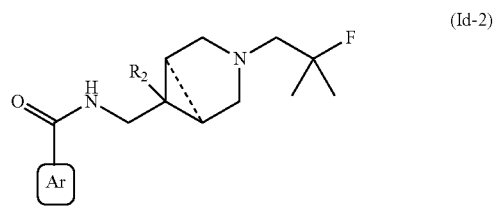

(Id-2)

or a stereoisomer, a pharmaceutically acceptable salt thereof,
wherein,
"--------" is a bond or no bond;

Ar is

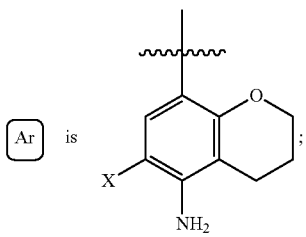

X is chlorine;
"⸺" is point of attachment;
$R_2$ is hydrogen or fluorine; provided that $R_2$ is fluorine when "--------" is no bond;
(e) a compound of formula (Ie-1):

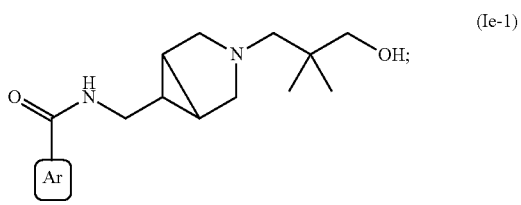

(Ie-1)

or a stereoisomer, a pharmaceutically acceptable salt thereof,
wherein,

Ar is

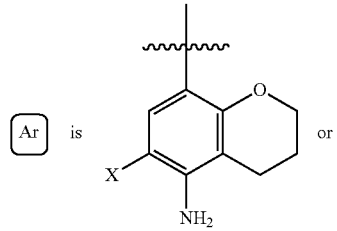

or

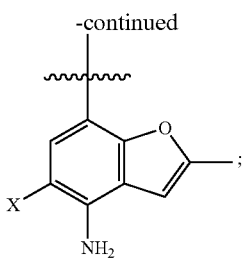

X is chlorine;
"~~~" is point of attachment;
(f) a compound of formula (Ie-2):

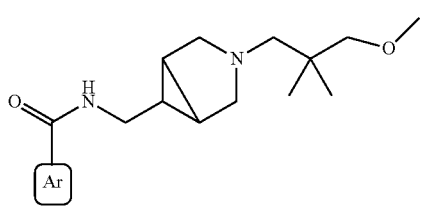

or a stereoisomer, a pharmaceutically acceptable salt thereof,

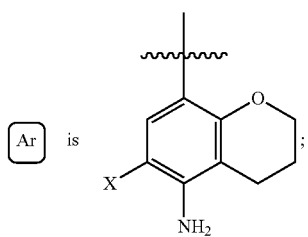

Ar is

X is chlorine;
"~~~" is point of attachment; and
(g) a compound of formula (If-1):

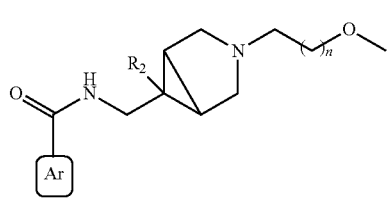

or a stereoisomer, a pharmaceutically acceptable salt thereof,
wherein,

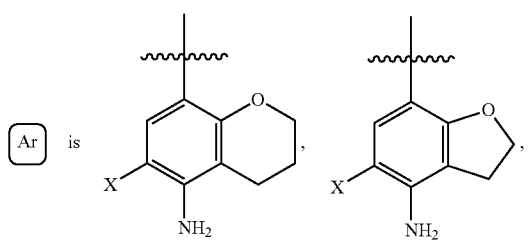

Ar is

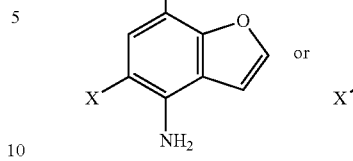

X is chlorine or bromine;
$R_2$ is hydrogen or fluorine;
"n" is 1 or 2.

4. The compound according to claim 1, which is selected from the group consisting of:
- 5-Amino-6-chloro-N-{[3-(tetrahydro-2H-pyran-4-ylmethyl)-3-azabicyclo[3.1.0]hex-6-yl]methyl}chroman-8-carboxamide hydrochloride;
- 5-Amino-6-chloro-N-{[3-(tetrahydro-2H-pyran-4-ylmethyl)-3-azabicyclo[3.1.0]hex-6-yl]methyl}chroman-8-carboxamide hemifumarate;
- 5-Amino-6-chloro-N-{[3-(tetrahydro-2H-pyran-4-ylmethyl)-3-azabicyclo[3.1.0]hex-6-yl]methyl}chroman-8-carboxamide L(+)-tartarate;
- 5-Amino-6-chloro-N-{[3-(tetrahydro-2H-pyran-4-ylmethyl)-3-azabicyclo[3.1.0]hex-6-yl]methyl}chroman-8-carboxamide;
- 5-Amino-6-chloro-N-{[3-(tetrahydro-2H-pyran-4-yl)-3-azabicyclo[3.1.0]hex-6-yl]methyl}chroman-8-carboxamide;
- 5-Amino-6-chloro-N-{[3-(tetrahydro-2H-pyran-4-yl)-3-azabicyclo[3.1.0]hex-6-yl]methyl}chroman-8-carboxamide L(+)-tartarate;
- 5-Amino-N-{[3-(tetrahydro-2H-pyran-4-ylmethyl)-3-azabicyclo[3.1.0]hex-6-yl]methyl}chroman-8-carboxamide L(+)-tartarate;
- 5-Amino-N-{[3-(tetrahydro-2H-pyran-4-ylmethyl)-3-azabicyclo[3.1.0]hex-6-yl]methyl}chroman-8-carboxamide;
- (R,S) 5-Amino-6-chloro-N-{[3-(tetrahydro-3-furanylmethyl)-3-azabicyclo[3.1.0]hex-6-yl]methyl}chroman-8-carboxamide;
- (R,S) 5-Amino-6-chloro-N-{[3-(tetrahydro-3-furanylmethyl)-3-azabicyclo[3.1.0]hex-6-yl]methyl}chroman-8-carboxamide L(+)-tartarate;
- 5-Amino-6-bromo-N-{[3-(tetrahydro-2H-pyran-4-ylmethyl)-3-azabicyclo[3.1.0]hex-6-yl]methyl}chroman-8-carboxamide;
- 5-Amino-6-bromo-N-{[3-(tetrahydro-2H-pyran-4-ylmethyl)-3-azabicyclo[3.1.0]hex-6-yl]methyl}chroman-8-carboxamide L(+)-tartarate;
- 4-Amino-5-chloro-N-{[3-(tetrahydro-2H-pyran-4-ylmethyl)-3-azabicyclo[3.1.0]hex-6-yl]methyl}benzofuran-7-carboxamide;
- 4-Amino-5-chloro-N-{[3-(tetrahydro-2H-pyran-4-ylmethyl)-3-azabicyclo[3.1.0]hex-6-yl]methyl}benzofuran-7-carboxamide hydrochloride;
- 4-Amino-5-chloro-N-{[3-(tetrahydro-2H-pyran-4-yl)-3-azabicyclo[3.1.0]hex-6-yl]methyl}benzofuran-7-carboxamide;
- 4-Amino-5-chloro-N-{[3-(tetrahydro-2H-pyran-4-yl)-3-azabicyclo[3.1.0]hex-6-yl]methyl}benzofuran-7-carboxamide oxalate;
- 4-Amino-5-chloro-N-{[3-(1-methoxycarbonylpiperidine-4-yl)-3-azabicyclo[3.1.0]hex-6-yl]methyl}benzofuran-7-carboxamide;

4-Amino-5-chloro-N-{[3-(1-methoxycarbonylpiperidine-4-yl)-3-azabicyclo[3.1.0]hex-6-yl]methyl}benzofuran-7-carboxamide oxalate;
4-Amino-5-chloro-2-methyl-N-{[3-(tetrahydro-2H-pyran-4-ylmethyl)-3-azabicyclo[3.1.0]hex-6-yl]methyl}benzofuran-7-carboxamide;
4-Amino-5-chloro-2-methyl-N-{[3-(tetrahydro-2H-pyran-4-ylmethyl)-3-azabicyclo[3.1.0]hex-6-yl]methyl}benzofuran-7-carboxamide hydrochloride;
4-Amino-5-chloro-N-[3-isopropyl-3-azabicyclo[3.1.0]hex-6-yl)methyl]-2,3-dihydrobenzofuran-7-carboxamide;
4-Amino-5-chloro-N-[3-isopropyl-3-azabicyclo[3.1.0]hex-6-yl)methyl]-2,3-dihydrobenzofuran-7-carboxamide oxalate;
4-Amino-5-chloro-N-{[3-(cyclobutylmethyl)-3-azabicyclo[3.1.0]hex-6-yl]methyl}-2,3-dihydrobenzofuran-7-carboxamide;
4-Amino-5-chloro-N-{[3-(cyclobutylmethyl)-3-azabicyclo[3.1.0]hex-6-yl]methyl}-2,3-dihydrobenzofuran-7-carboxamide oxalate;
4-Amino-5-chloro-N-{[3-(1-methoxycarbonylpiperidine-4-yl)-3-azabicyclo[3.1.0]hex-6-yl]methyl}-2,3-dihydrobenzofuran-7-carboxamide;
4-Amino-5-chloro-N-{[3-(1-methoxycarbonylpiperidine-4-yl)-3-azabicyclo[3.1.0]hex-6-yl]methyl}-2,3-dihydrobenzofuran-7-carboxamide L(+)-tartarate;
4-Amino-5-chloro-N-{[3-(tetrahydropyran-4-ylmethyl)-3-azabicyclo[3.1.0]hex-6-yl]methyl}-2,3-dihydrobenzofuran-7-carboxamide;
4-Amino-5-chloro-N-{[3-(tetrahydropyran-4-ylmethyl)-3-azabicyclo[3.1.0]hex-6-yl]methyl}-2,3-dihydrobenzofuran-7-carboxamide L(+)-tartarate;
4-Amino-5-chloro-N-{[3-(tetrahydropyran-4-yl)-3-azabicyclo[3.1.0]hex-6-yl]methyl}-2,3-dihydrobenzofuran-7-carboxamide;
4-Amino-5-chloro-N-{[3-(tetrahydropyran-4-yl)-3-azabicyclo[3.1.0]hex-6-yl]methyl}-2,3-dihydrobenzofuran-7-carboxamide oxalate;
4-Amino-5-bromo-N-{[3-(tetrahydropyran-4-yl)-3-azabicyclo[3.1.0]hex-6-yl]methyl}-2,3-dihydrobenzofuran-7-carboxamide;
4-Amino-5-bromo-N-{[3-(tetrahydropyran-4-yl)-3-azabicyclo[3.1.0]hex-6-yl]methyl}-2,3-dihydrobenzofuran-7-carboxamide oxalate;
5-Amino-6-chloro-N-{[3-(4-hydroxytetrahydro-2H-pyran-4-ylmethyl)-3-azabicyclo[3.1.0]hex-6-yl]methyl}chroman-8-carboxamide;
5-Amino-6-chloro-N-{[3-(4-hydroxytetrahydro-2H-pyran-4-ylmethyl)-3-azabicyclo[3.1.0]hex-6-yl]methyl}chroman-8-carboxamide L(+)-tartarate;
4-Amino-5-chloro-N-{[3-(4-hydroxytetrahydro-2H-pyran-4-ylmethyl)-3-azabicyclo[3.1.0]hex-6-yl]methyl}benzofuran-7-carboxamide;
4-Amino-5-chloro-N-{[3-(4-hydroxytetrahydro-2H-pyran-4-ylmethyl)-3-azabicyclo[3.1.0]hex-6-yl]methyl}benzofuran-7-carboxamide oxalate;
4-Amino-5-chloro-N-{[3-(4-hydroxytetrahydropyran-4-ylmethyl)-3-azabicyclo[3.1.0]hex-6-yl]methyl}-2,3-dihydrobenzofuran-7-carboxamide;
4-Amino-5-chloro-N-{[3-(4-hydroxytetrahydropyran-4-ylmethyl)-3-azabicyclo[3.1.0]hex-6-yl]methyl}-2,3-dihydrobenzofuran-7-carboxamide oxalate;
5-Amino-6-chloro-N-{[3-(4-fluorotetrahydro-2H-pyran-4-ylmethyl)-3-azabicyclo[3.1.0]hex-6-yl]methyl}chroman-8-carboxamide;
5-Amino-6-chloro-N-{[3-(4-fluorotetrahydro-2H-pyran-4-ylmethyl)-3-azabicyclo[3.1.0]hex-6-yl]methyl}chroman-8-carboxamide L(+)-tartarate;
5-Amino-6-chloro-N-{[3-(2-hydroxy-2-methyl propyl)-3-azabicyclo[3.1.0]hex-6-yl] methyl}chroman-8-carboxamide;
5-Amino-6-chloro-N-{[3-(2-hydroxy-2-methyl propyl)-3-azabicyclo[3.1.0]hex-6-yl] methyl}chroman-8-carboxamide L(+)-tartarate;
4-Amino-5-chloro-N-{[4-fluoro-1-(2-hydroxy-2-methyl propyl)-4-piperidinyl]methyl}benzofuran-7-carboxamide;
4-Amino-5-chloro-N-{[4-fluoro-1-(2-hydroxy-2-methyl propyl)-4-piperidinyl]methyl}benzofuran-7-carboxamide hydrochloride;
4-Amino-5-chloro-N-{[3-(2-hydroxy-2-methylpropyl)-3-azabicyclo[3.1.0]hex-6-yl]methyl}-2,3-dihydrobenzofuran-7-carboxamide;
4-Amino-5-chloro-N-{[3-(2-hydroxy-2-methylpropyl)-3-azabicyclo[3.1.0]hex-6-yl]methyl}-2,3-dihydrobenzofuran-7-carboxamide oxalate;
5-Amino-6-chloro-N-{[4-fluoro-1-(2-hydroxy-2-methyl propyl)-4-piperidinyl]methyl}chroman-8-carboxamide;
5-Amino-6-chloro-N-{[4-fluoro-1-(2-hydroxy-2-methyl propyl)-4-piperidinyl]methyl}chroman-8-carboxamide L(+)-tartarate;
5-Amino-6-bromo-N-{[4-fluoro-1-(2-hydroxy-2-methyl propyl)-4-piperidinyl]methyl}chroman-8-carboxamide;
5-Amino-6-bromo-N-{[4-fluoro-1-(2-hydroxy-2-methyl propyl)-4-piperidinyl]methyl}chroman-8-carboxamide L(+)-tartarate;
4-Amino-5-chloro-N-{[4-fluoro-1-(2-hydroxy-2-methyl propyl)-4-piperidinyl]methyl}benzofuran-7-carboxamide L(+)-tartarate;
4-Amino-5-chloro-N-{[3-(2-hydroxy-2-methyl propyl)-3-azabicyclo[3.1.0]hex-6-yl]methyl}benzofuran-7-carboxamide;
4-Amino-5-chloro-N-{[3-(2-hydroxy-2-methyl propyl)-3-azabicyclo[3.1.0]hex-6-yl]methyl}benzofuran-7-carboxamide L(+)-tartarate;
4-Amino-5-chloro-2-methyl-N-{[4-fluoro-1-(2-hydroxy-2-methyl propyl)-4-piperidinyl]methyl}benzofuran-7-carboxamide;
4-Amino-5-chloro-2-methyl-N-{[4-fluoro-1-(2-hydroxy-2-methyl propyl)-4-piperidinyl]methyl}benzofuran-7-carboxamide L(+)-tartarate;
4-Amino-5-chloro-2-methyl-N-{[3-(2-hydroxy-2-methyl propyl)-3-azabicyclo[3.1.0]hex-6-yl] methyl}benzofuran-7-carboxamide;
5-Amino-6-chloro-N-{[1-(2-fluoro-2-methyl propyl)-4-fluoro-4-piperidinyl] methyl}chroman-8-carboxamide;
5-Amino-6-chloro-N-{[1-(2-fluoro-2-methyl propyl)-4-fluoro-4-piperidinyl]methyl}chroman-8-carboxamide L(+)-tartarate;
5-Amino-6-chloro-N-{[3-(3-hydroxy-2,2-dimethyl propyl)-3-azabicyclo[3.1.0]hex-6-yl] methyl}chroman-8-carboxamide;
5-Amino-6-chloro-N-{[3-(3-hydroxy-2,2-dimethyl propyl)-3-azabicyclo[3.1.0]hex-6-yl] methyl}chroman-8-carboxamide L(+)-tartarate;
5-Amino-6-chloro-N-{[3-(3-methoxy-2,2-dimethyl propyl)-3-azabicyclo[3.1.0]hex-6-yl] methyl}chroman-8-carboxamide;

4-Amino-5-chloro-N-{[3-(3-methoxypropyl)-3-azabicyclo[3.1.0]hex-6-yl] methyl}-2,3-dihydrobenzofuran-7-carboxamide;

4-Amino-5-chloro-N-{[3-(3-methoxypropyl)-3-azabicyclo[3.1.0]hex-6-yl] methyl}-2,3-dihydrobenzofuran-7-carboxamide oxalate;

4-Amino-5-chloro-N-{[3-(3-methoxy propyl)-3-azabicyclo[3.1.0]hex-6-yl]methyl}benzofuran-7-carboxamide;

4-Amino-5-chloro-N-{[3-(3-methoxy propyl)-3-azabicyclo[3.1.0]hex-6-yl]methyl}benzofuran-7-carboxamide hydrochloride;

4-Amino-5-chloro-2-methyl-N-{[3-(3-methoxy propyl)-3-azabicyclo[3.1.0]hex-6-yl]methyl}benzofuran-7-carboxamide;

4-Amino-5-chloro-2-methyl-N-{[3-(3-methoxy propyl)-3-azabicyclo[3.1.0]hex-6-yl]methyl}benzofuran-7-carboxamide hydrochloride; and 4-Amino-5-bromo-N-{[3-(3-methoxypropyl)-3-azabicyclo[3.1.0]hex-6-yl]methyl}-2,3-dihydrobenzofuran-7-carboxamide oxalate.

5. A pharmaceutical composition comprising the compound according to claim 1, and pharmaceutically acceptable excipients or carriers.

6. The pharmaceutical composition according to claim 5, for the treatment of clinical conditions mediated through 5-$HT_4$ receptor selected from Alzheimer's disease, schizophrenia, attention deficit hyperactivity disorder, Huntington's disease, Parkinson's disease, depression or psychiatric disorders.

7. A method for treating Alzheimer's disease, schizophrenia, attention deficit hyperactivity disorder, Huntington's disease, Parkinson's disease, depression or psychiatric disorders, comprising the step of administering to a patient in need thereof an effective amount of a compound or a pharmaceutically acceptable salt thereof according to claim 1.

8. A method for the treatment of diseases related to 5-$HT_4$ receptor, comprising the step of administering to a patient in need thereof an effective amount of the compound or a pharmaceutically acceptable salt thereof according to claim 1.

9. A method for the treatment of clinical conditions selected from Alzheimer's disease, schizophrenia, attention deficit hyperactivity disorder, Huntington's disease, Parkinson's disease, depression, and psychiatric disorders, comprising the step of administering to a patient in need thereof an effective amount of the compound or a pharmaceutically acceptable salt thereof according to claim 4.

* * * * *